United States Patent
Ronsin et al.

(10) Patent No.: US 9,079,821 B2
(45) Date of Patent: Jul. 14, 2015

(54) QUINONE BASED NITRIC OXIDE DONATING COMPOUNDS

(71) Applicant: NICOX S.A., Sophia Antipolis-Valbonne (FR)

(72) Inventors: Gael Ronsin, Milan (IT); Laura Storoni, Cesano Maderno (IT); Francesca Benedini, San Donato Milanese (IT)

(73) Assignee: NICOX SCIENCE IRELAND, Dublin (IE)

( * ) Notice: Subject to any disclaimer, the term of this patent is extended or adjusted under 35 U.S.C. 154(b) by 0 days.

(21) Appl. No.: 14/161,520

(22) Filed: Jan. 22, 2014

(65) Prior Publication Data
US 2014/0135389 A1    May 15, 2014

Related U.S. Application Data

(62) Division of application No. 14/126,363, filed as application No. PCT/EP2012/070953 on Oct. 23, 2012.

(30) Foreign Application Priority Data

Oct. 24, 2011   (EP) .................................. 11186301

(51) Int. Cl.
| | |
|---|---|
| *C07C 203/04* | (2006.01) |
| *C07C 323/22* | (2006.01) |
| *C07D 307/20* | (2006.01) |
| *A61K 45/06* | (2006.01) |
| *A61K 31/341* | (2006.01) |
| *A61K 31/21* | (2006.01) |

(52) U.S. Cl.
CPC ............... *C07C 203/04* (2013.01); *A61K 31/21* (2013.01); *A61K 31/341* (2013.01); *A61K 45/06* (2013.01); *C07C 323/22* (2013.01); *C07D 307/20* (2013.01); *C07C 2101/16* (2013.01)

(58) Field of Classification Search
CPC   C07C 2101/16; C07C 203/04; C07C 323/22; C07D 307/20; A61K 45/06; A61K 31/341; A61K 31/21; A61K 2300/00
USPC .......... 514/471, 509, 676, 677; 552/307, 310, 552/299; 549/478; 558/483
See application file for complete search history.

(56) References Cited

FOREIGN PATENT DOCUMENTS

| | | | | |
|---|---|---|---|---|
| GB | 2 349 385 | A | 11/2000 | |
| GB | 2349385 | A * | 11/2000 | ............ C07C 203/04 |

OTHER PUBLICATIONS

Mack et al, Int. J Biochem. Cell Biol. 2006, 38(8), 1237-43.*
Fabiane C. De Abreu, et al., "Nitrooxyquinones: synthesis, X-ray diffraction and electrochemical studies," Tetrahedron Letters, Nov. 4, 2002, pp. 8153-8157, vol. 43, No. 45, Elsevier Science Ltd., Amsterdam, NL.
International Search Report, European Patent Application No. PCT/EP2012/070953 dated Jan. 31, 2013.
Murakami, et al., Superoxide radical scavenging acitivity of idebenone in vitro studied by ESR spin trapping method and direct ESR measurement at liquid nitrogen temperature, Archives of Gerontology and Geriatrics, Nov. 1, 1990, pp. 199-214, vol. 11, No. 3, Elsevier Sci. Pub. B.V., Amsterdam, NL.

* cited by examiner

*Primary Examiner* — Ganapathy Krishnan
(74) *Attorney, Agent, or Firm* — Arent Fox LLP

(57) ABSTRACT

The present invention relates to nitric oxide donor compounds having a quinone based structure, to processes for their preparation and to their use in the treatment of pathological conditions where a deficit of NO plays an important role in their pathogenesis.

1 Claim, No Drawings

QUINONE BASED NITRIC OXIDE DONATING COMPOUNDS

CROSS-REFERENCE TO RELATED APPLICATIONS

This is a Divisional Application of U.S. patent application Ser. No. 14/126,363, filed Dec. 13, 2013; which is a National Phase Entry of International Patent Application No. PCT/EP2012/070953, filed Oct. 23, 2012; which claims priority of European Patent Application No. 11186301.5, filed Oct. 24, 2011. The disclosures of the prior applications are hereby incorporated in their entirety by reference.

The present invention relates to nitric oxide donor compounds, to processes for their preparation and to their use in the treatment of vascular diseases and in particular in the treatment of pathological conditions where a deficit of NO plays an important role in their pathogenesis.

It is known that NO plays multiple physiological roles in regulating numerous and diverse organ functions, defects in the NO pathway lead to the development of many different pathological conditions. These disorders include hypertension, atherosclerosis, coronary artery diseases, cardiac failure, pulmonary hypertension, stroke, impotence, vascular complications in diabetes mellitus, gastrointestinal ulcers, asthma, and other central and peripheral nervous system disorders.

Organic nitrates (esters of nitric acid) are proven medicinal substances for the treatment of dysfunctions of the circulatory system preferably cardiovascular and coronary dysfunctions. They display their effect both by relieving the heart via a reduction in the preload and after load and by improving the oxygen supply to the heart via coronary dilatation.

However, it has been found that the classical organic nitrates used in therapy, such as glycerol trinitrate, isosorbide dinitrate or isosorbide 5-mononitrate, display, on continuous intake of high doses and within a short time, a distinct attenuation of the effect, the so-called nitrate tolerance or tachyphylaxis.

Nitrate tolerance develops despite an elevation in the drug plasma concentration reflecting a decrease in vascular sensitivity to previously therapeutic levels. This can be prevented or reduced by inclusion of a nitrate free period in the dosing schedule.

Nitrate-tolerant individuals are more susceptible to enhanced vasoconstriction whenever the plasma nitrate concentration is allowed to fall, the so-called rebound effect. This is reflected by increased sensitivity to a number of circulating vasoconstrictor substances such as catecholamines and angiotensin II. Clinically the rebound effect may be more important than is currently recognized. Evidence suggests that even intermittent nitrate patch therapy results in increased vasoconstrictor sensitivity during the patch-off period. [Munzel T, Mollnau H, Hartmann M, et al. Effects of a nitrate-free interval on tolerance, vasoconstrictor sensitivity and vascular superoxide production. J Am Coll Cardiol. 2000; 36:628-634].

Organic nitrates also cause unpleasant important side effects that include headache, hypotension, flush and nausea. Headache is the most prominent side effect and is caused by cerebral vasodilatation.

The nitrate tolerance and the other side effects have restricted the clinical use and effectiveness of nitrates.

Therefore nitric oxide donor compounds which can produce extended release of NO and do not give rise to any nitrate tolerance are needed.

It is known that one way of reducing the tolerance of the nitrated organic compounds consists of introducing a thiol group in the molecule, for example by use of sulphur containing amino acids. Accordingly EP 0 362 575 and EP 0 451 760 claim compounds which contain sulphydryl groups and prevent nitrate tolerance or diminish a nitrate tolerance which has already occurred.

Patent application WO-A-92/04337 describes organic nitrated derivatives of the thiazolidine ring with vasodilating activity and a reduced tolerance.

U.S. Pat. No. 5,591,758 describes an enormous amount of different nitrated organic vasodilating compounds of highly variable structures and showing reduced tolerance.

Patent EP 1 120 419 describes isosorbide mononitrates wherein the free hydroxyl group is esterified with either carboxylic acids or with thioacids wherein said ester groups are in trans position with respect to the nitrate group.

Published studies disclose that concomitant treatment with antioxidants preserves the sensitivity of the vasculature to organic nitrates in different experimental models. However the use of antioxidants in clinical practice is limited by the fact that oral administration of antioxidants leads to low bioavailability of the antioxidants and consequently lack of efficacy.

The present invention provides nitric oxide donors having a better pharmacological activity in term of a significant inferior tolerance and a longer duration of action than that of nitric oxide donors described in the art.

The present invention also includes the use of nitric oxide donors for the prevention and/or treatment of pulmonary hypertension, the treatment and/or prevention of dysfunctions of the circulatory system involving vasculopathies preferably pulmonary arterial hypertension, Sickle cell disease, systemic sclerosis, scleroderma, muscular dystrophies such as Duchenne's muscular dystrophy and Becker's muscular dystrophy, cardiac allograft vasculopathy, pathological conditions where oxidative stress plays an important role in their pathogenesis, and/or tissue damage due to ischemia and/or due to ischemia-reperfusion, ophthalmic diseases, glaucoma and ocular hypertension.

The present invention relates to compounds of formula (I)

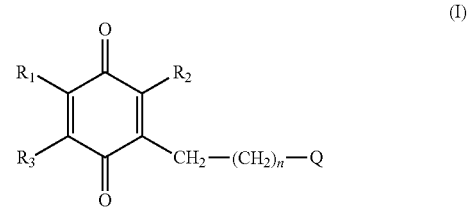

or stereoisomers thereof, wherein $R_1$ is selected from H, methyl, methoxy;

$R_3$ is selected from H, methyl, methoxy or $R_1$ and $R_3$ together form —CH=CH—CH=CH—;

$R_2$ is H, methyl;

n is an integer from 0 to 10; preferably n is an integer from 0 to 6;

Q is selected from the group consisting of:

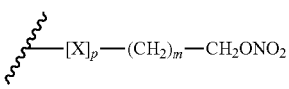

(II)

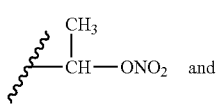
and (III)

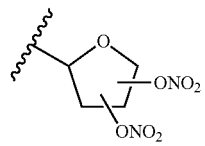

(IV)

wherein
m is an integer from 0 to 6; preferably m is an integer from 0 to 3;
p is an integer from 0 to 1;
X is O, S or is —CHONO$_2$, with the proviso that when X is —CHONO$_2$ then m is 0.

In one embodiment of the invention, the compound has the formula (Ia)

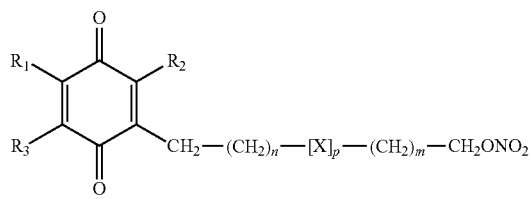

(Ia)

wherein
R$_1$ is selected from H, methyl, methoxy;
R$_3$ is selected from H, methyl, methoxy
or R$_1$ and R$_3$ together form —CH=CH—CH=CH—;
R$_2$ is H, methyl;
n is an integer from 0 to 10; preferably n is an integer from 0 to 6;
m is an integer from 0 to 6; preferably m is an integer from 0 to 3;
p is an integer from 0 to 1;
X is O, S or is —CHONO$_2$, with the proviso that when X is —CHONO$_2$ then m is 0.

In another embodiment of the invention, the compound has the formula (Ia)

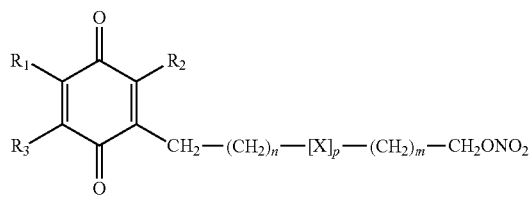

(Ia)

wherein
R$_1$ is selected from H, methyl, methoxy;
R$_3$ is selected from H, methyl, methoxy
or R$_1$ and R$_3$ together form —CH=CH—CH=CH—;
R$_2$ is H, methyl;
n is an integer from 0 to 10; preferably n is an integer from 0 to 6;
m is an integer from 0 to 6; preferably m is an integer from 0 to 3;
p is 0.

In another embodiment of the invention, the compound has the formula (Ia)

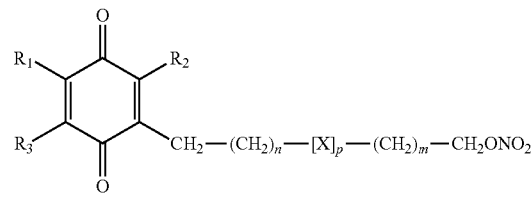

(Ia)

wherein
R$_1$ is selected from H, methyl, methoxy;
R$_3$ is selected from H, methyl, methoxy
or R$_1$ and R$_3$ together form —CH=CH—CH=CH—;
R$_2$ is H, methyl;
n is an integer from 0 to 10; preferably n is an integer from 0 to 6;
m is an integer from 0 to 6; preferably m is an integer from 0 to 3;
p is 1;
X is O.

In another embodiment of the invention, the compound has the formula (Ib) or (Ic)

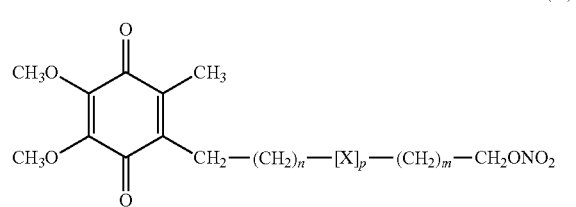

(Ib)

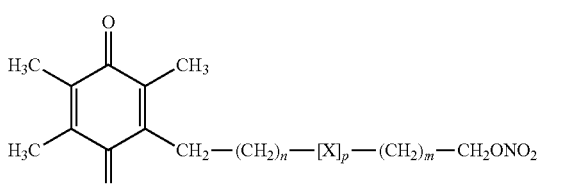

(Ic)

wherein:
n is an integer from 0 to 10; preferably n is an integer from 0 to 6;
m is an integer from 0 to 6; preferably m is an integer from 0 to 3;
p is an integer from 0 to 1;
X is O, S or is —CHONO$_2$, with the proviso that when X is —CHONO$_2$ then m is 0;

In another embodiment of the invention, the compound has the formula (Ib) or (Ic)

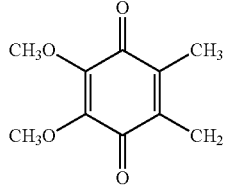
(Ib)

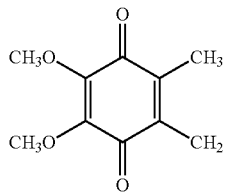
(Ic)

wherein
n is an integer from 0 to 10; preferably n is an integer from 0 to 6;
m is an integer from 0 to 6; preferably m is an integer from 0 to 3;
p is 0.

In another embodiment of the invention, the compound has the formula (Ib) or (Ic)

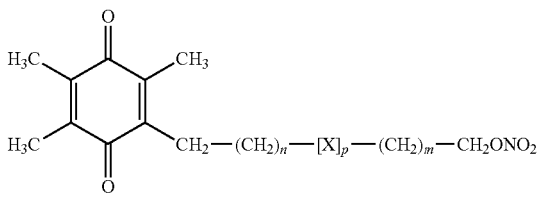
(Ib)

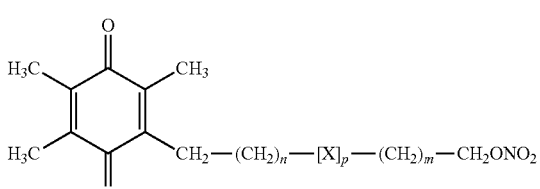
(Ic)

wherein
n is an integer from 0 to 10; preferably n is an integer from 0 to 6;
m is an integer from 0 to 6; preferably m is an integer from 0 to 3;
p is 1 and X is O or S.

In another embodiment of the invention, the compound has the formula (Id) or (Ie)

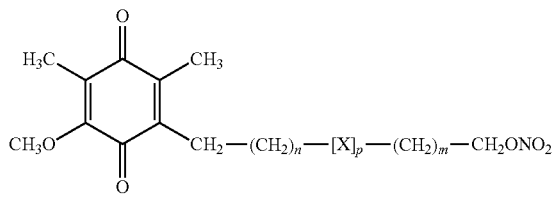
(Id)

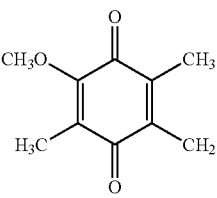
(Ie)

wherein:
n is an integer from 0 to 10; preferably n is an integer from 0 to 6;
m is an integer from 0 to 6; preferably m is an integer from 0 to 3;
p is an integer from 0 to 1;
X is O, S or is —CHONO$_2$, with the proviso that when X is —CHONO$_2$ then m is 0;

In another embodiment of the invention, the compound has the formula (Id) or (Ie)

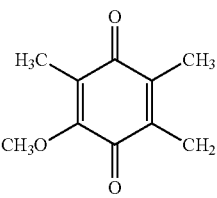
(Id)

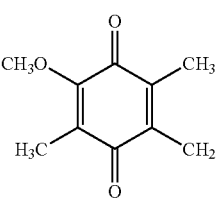
(Ie)

wherein
n is an integer from 0 to 10; preferably n is an integer from 0 to 6;
m is an integer from 0 to 6; preferably m is an integer from 0 to 3;
p is 0.

In another embodiment of the invention, the compound has the formula (Id) or (Ie)

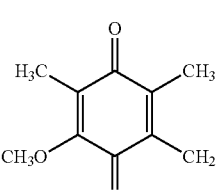
(Id)

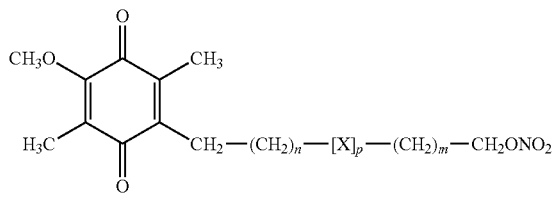

(Ie)

wherein n is an integer from 0 to 10; preferably n is an integer from 0 to 6;

m is an integer from 0 to 6; preferably m is an integer from 0 to 3;

p is 1 and X is O or S.

In another embodiment of the invention, the compound has the formula (If)

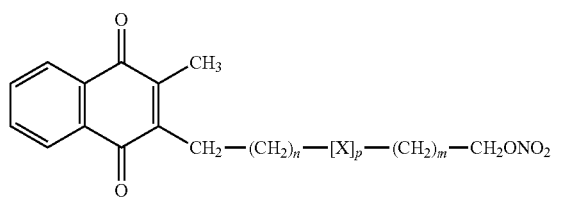

(If)

wherein n is an integer from 0 to 10; preferably n is an integer from 0 to 6;

m is an integer from 0 to 6; preferably m is an integer from 0 to 3;

p is 0.

In another embodiment of the invention, the compound has the formula (If)

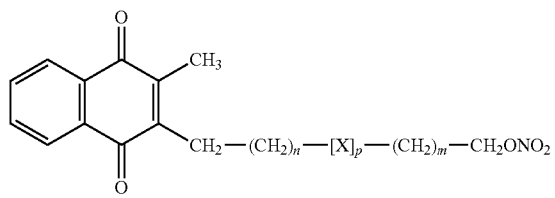

(If)

wherein n is an integer from 0 to 10; preferably n is an integer from 0 to 6;

m is an integer from 0 to 6; preferably m is an integer from 0 to 3;

p is 1;

X is O, S or is —CHONO$_2$, with the proviso that when X is —CHONO$_2$ then m is 0.

In another embodiment of the invention, the compound or stereoisomers thereof has the formula (Ig) or (Ih)

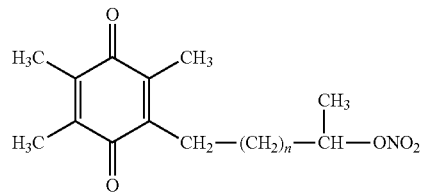

(Ig)

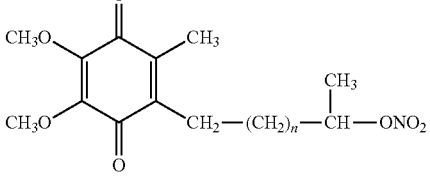

(Ih)

wherein:

n is an integer from 0 to 10; preferably n is an integer from 0 to 6.

In another embodiment of the invention, the compound or stereoisomers thereof has the formula (Ii), (Il) or (Im)

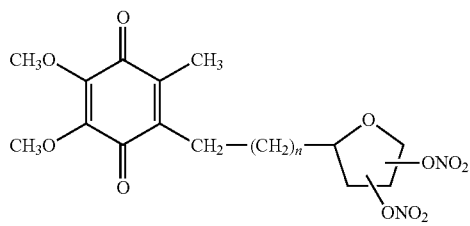

(Ii)

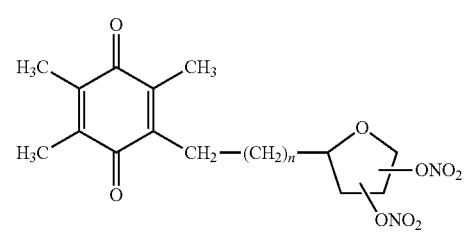

(Il)

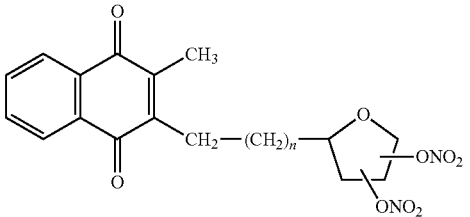

(Im)

wherein n is an integer from 0 to 10; preferably n is an integer from 0 to 6.

Another embodiment of the invention provides a compound of formula (I) selected from the group:

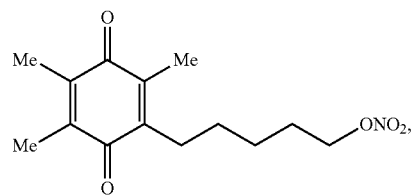

(1)

(2)
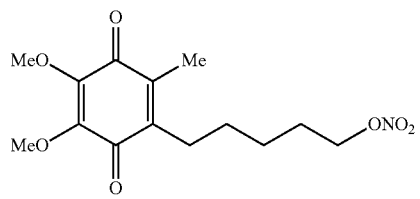
(3)
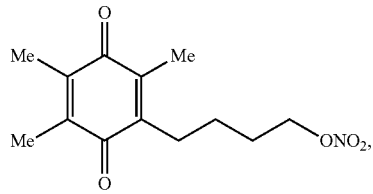
(4)
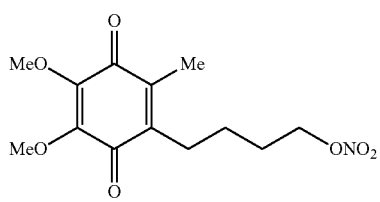
(5)
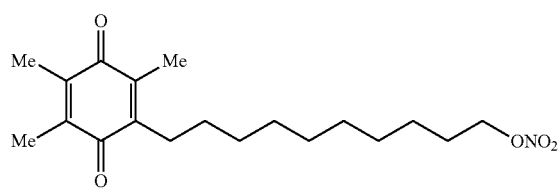
(6)
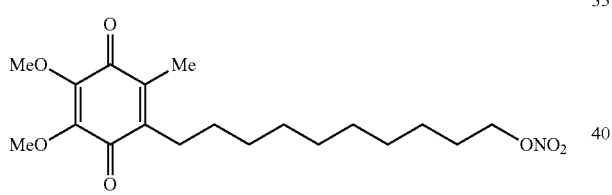
(7)
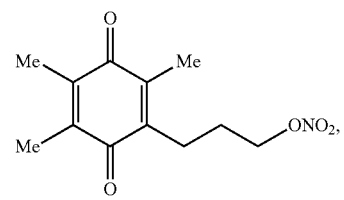
(8)
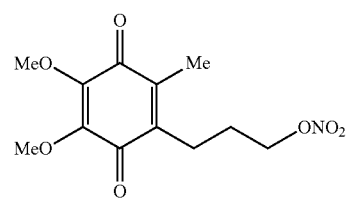
(9)
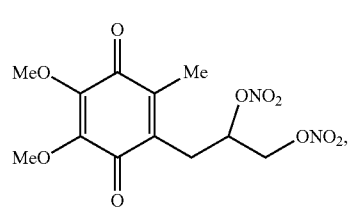
(10)
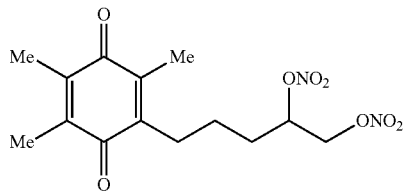
(11)
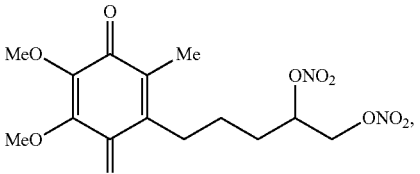
(12)
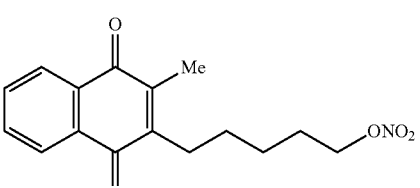
(13)
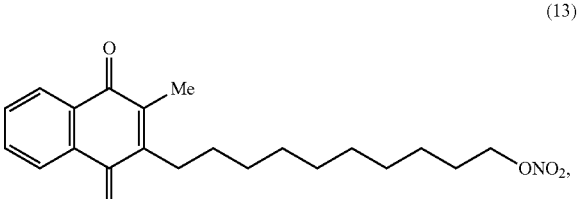
(14)
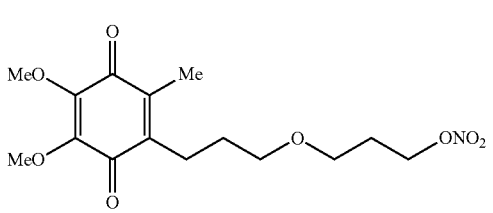
(15)
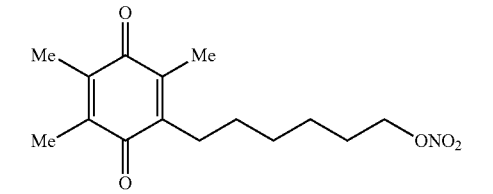
(16)
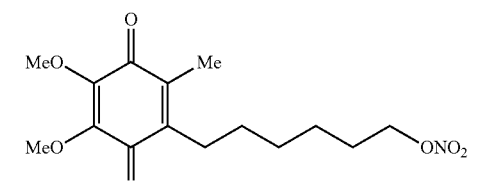
(17)
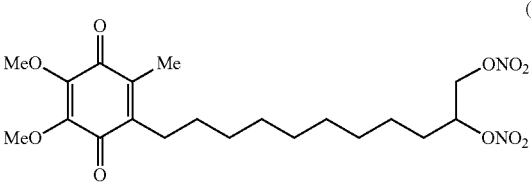

(18)
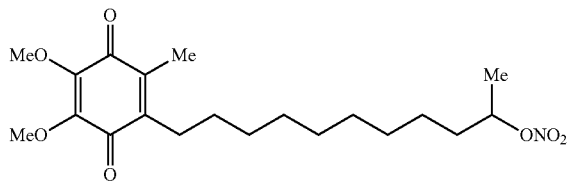
(19)
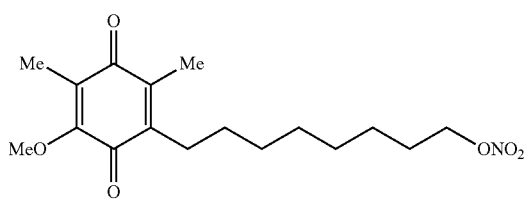
(20)
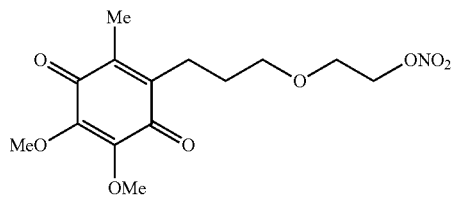
(21)
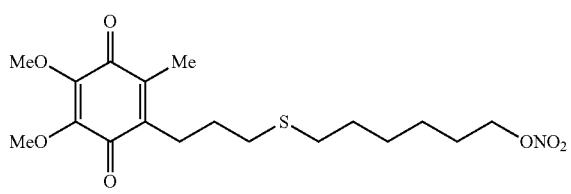
(22)
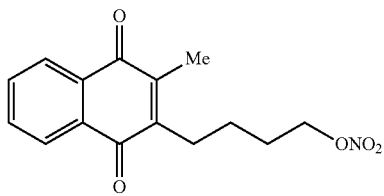
(23)
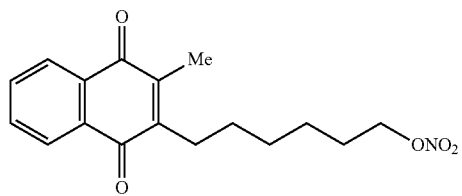
(24)
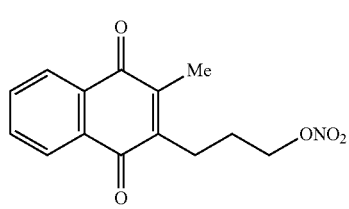
(25)
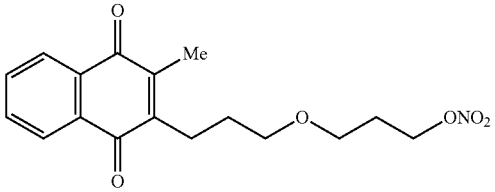
(26)
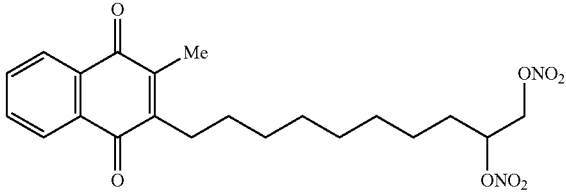
(27)
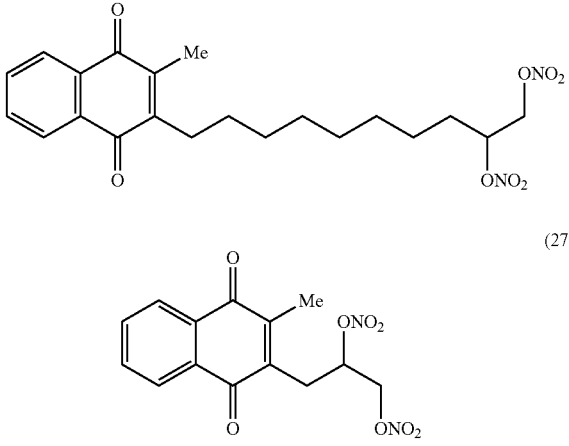
(28)
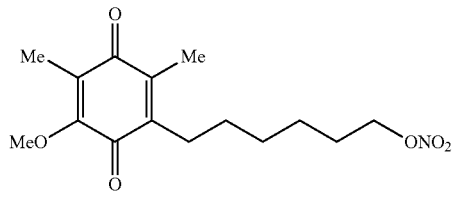
(29)
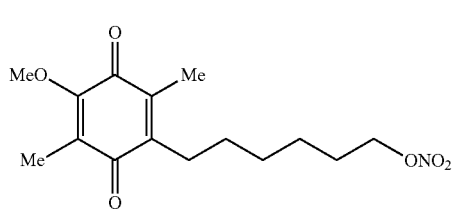
(30)
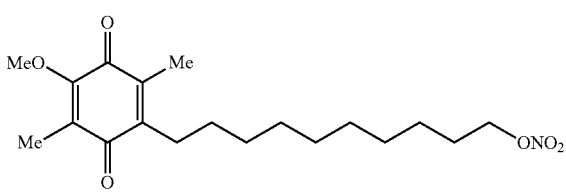
(31)
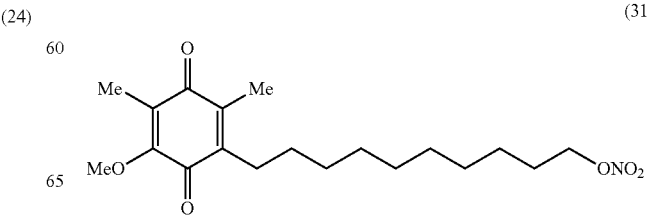

(32)
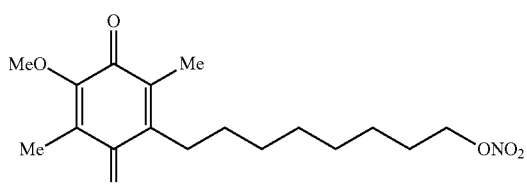

(33)
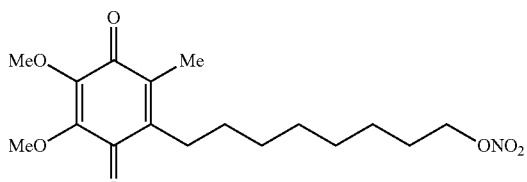

(34)
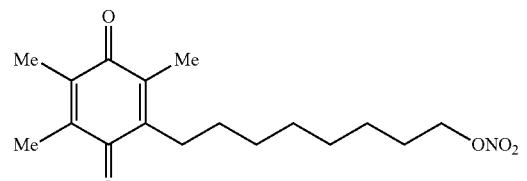

(35)
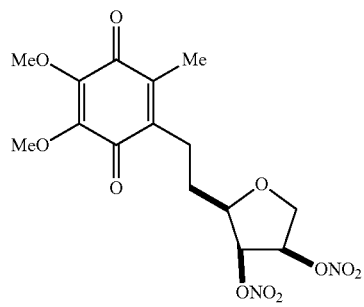

(36)
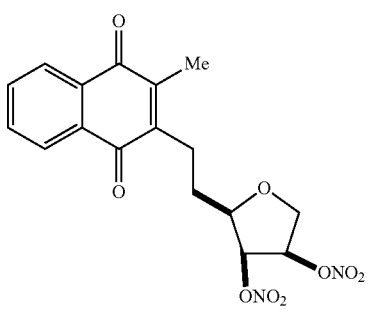

(37)
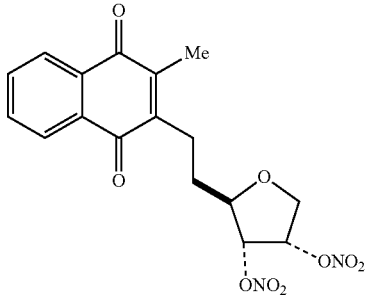

The tests performed demonstrated that compounds of formula (I) show a vasodilating activity comparable with that of the isosorbide mononitrate. Further, they manifest a significantly inferior tolerance and/or side effects as compared to those observed with isosorbide mononitrate. Consequently, the compounds of the invention may be used as drug with vasodilating effect for the treatment of pathological conditions where a deficit of NO plays an important role in their pathogenesis.

Additionally, the compounds of formula (I) may also be used in a therapy for the prevention and/or treatment of pulmonary hypertension, the treatment and/or prevention of dysfunctions of the circulatory system involving vasculopathies preferably pulmonary arterial hypertension, Sickle cell disease, systemic sclerosis, scleroderma, muscular dystrophies such as Duchenne's muscular dystrophy and Becker's muscular dystrophy, cardiac allograft vasculopathy, pathological conditions where oxidative stress plays an important role in their pathogenesis, and/or tissue damage due to ischemia and/or due to ischemia-reperfusion, ophthalmic diseases, glaucoma and ocular hypertension.

The pharmaceutical compositions may be administered by different routes. For example, they may be administered orally in form of pharmaceutically preparations such as tablets, capsules, syrups and suspensions, parenterally in form of solutions or emulsions, etc. They may also be administered topically in form of creams, pomades, balsams, and transdermically for example through the use of patches or bandages. The preparations may comprise physiologically acceptable carriers, excipients, activators, chelating agents, stabilizers, etc. In case of injections there may be incorporated physiologically acceptable buffers, solubilizing agents or isotonics.

The pharmaceutical compositions according to the present invention may further comprise a non steroidal anti-inflammatory drug (NSAID), a steroid drug, a thrombolytic agent such as plasminogen activator urokinase, streptokinase, alteplase or anistreplase.

Alternately, the pharmaceutical compositions according to the invention may further comprise a hypolipidemic agent preferably simvastatin, lovastatin, atorvastatin, pravastatin, fluvastatin, eptastatin, lifibrol, acifran, acitemate, glunicate or rosuvastatine.

The present inventions also relates to compositions comprising a nitric oxide donor of formula (I) in combination with one or more further active ingredients selected from the group consisting of alpha adrenergic agonist, beta blocker, carbonic anhydrase inhibitor, prostaglandin analogs, non-steroidal anti-inflammatory drugs, steroidal anti-inflammatory drugs.

Examples of suitable alpha adrenergic agonist are brimonidine, apraclonidine, clonidine.

Examples of suitable beta blocker are timolol, carteolol, betaxolol, levobunolol.

Examples of suitable carbonic anhydrase inhibitor are dorzolamide, acetazolamide, brinzolamide, dorzolamide, dichlorphenamide, methazolamide.

Examples of suitable prostaglandin analogs are bimatoprost, latanoprost, travoprost, unoprostone and tafluprost.

Examples of non-steroidal anti-inflammatory drugs are bromfenac, flurbiprofen, naproxen, ketoprofen.

Examples of steroidal anti-inflammatory drugs are dexamethsone, fluocinolone acetonide, triamcinolone acetonide, budesonide, prednisolone.

The daily dose may be varied depending on the specific symptoms, the age, the body weight of the patients, the specific mode of administration, etc., and a daily normal dose for an adult person could be between 0.1 to 1000 mg, and could be administered as one dose only or divided into several doses during the day.

General Synthesis
1. Compounds of formula (I)

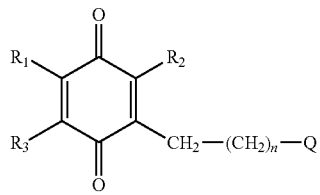

wherein n, $R_1$, $R_2$ and $R_3$ are as above defined and Q is the group of formula (II)

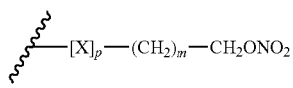

wherein p is 0 and m is as above defined, can be synthesized by nitrating a compound (V)

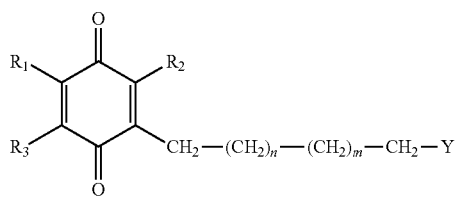

wherein Y is an halogen atom or Y is —OH.

When Y is a halogen atom the nitrate agent may be, for example, $AgNO_3$ in acetonitrile as known in the literature.

When Y is OH, compounds (V) can be nitrated using as nitrate agent a mixture of acetic anhydride and $HNO_3$ or triflic anhydride and tetra-alkylammonium nitrates salts in the presence of a base such as pyridine, lutidine, 2,6-di-tert-butyl-4-methylpyridine. Alternatively, the hydroxyl group is first converted to the corresponding mesyl or tosyl or triflate group and then nitrated using an appropriated nitrate agent such as known methods tetraalkylammonium nitrate and sodium nitrate.

Compounds of formula (V) wherein Y, n, m, $R_1$, $R_2$ and $R_3$ are as above defined are known in the literature or are made from methods described in the literature (Duveau D. Y. Bioor & Med Chemistry 2010, 18, 6429-6441).

1.1 Alternatively, compounds of formula (I) wherein n, $R_1$, $R_2$ and $R_3$ are as above defined and Q is the group of formula (II)

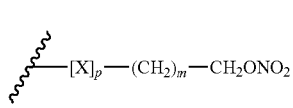

wherein p is 0 and m is as above defined, can be prepared by reacting a compound (VI) with a carboxylic acid of formula (VII).

$HOOC$—$(CH_2)_n$—$(CH_2)_m$—$CH_2ONO_2$ in the presence of salts of peroxydisulfuric acid such as ammonium or potassium salts and $AgNO_3$ in an appropriated solvent such as acetonitrile or acetonitrile/water under reflux, as described by Breyer, S. and co-workers in Chem Med Chem, 2009, 4(5), 761-768 or by Duveau D, Y et al in Bioor & Med Chemistry 2010, 18, 6429-6441 or by Kayashima, Tomoko et al. in Bioor & Med Chemistry, 2010 18(10), 6305-6309 when the two groups $R_1$ and $R_3$ taken together form —CH=CH—CH=CH—.

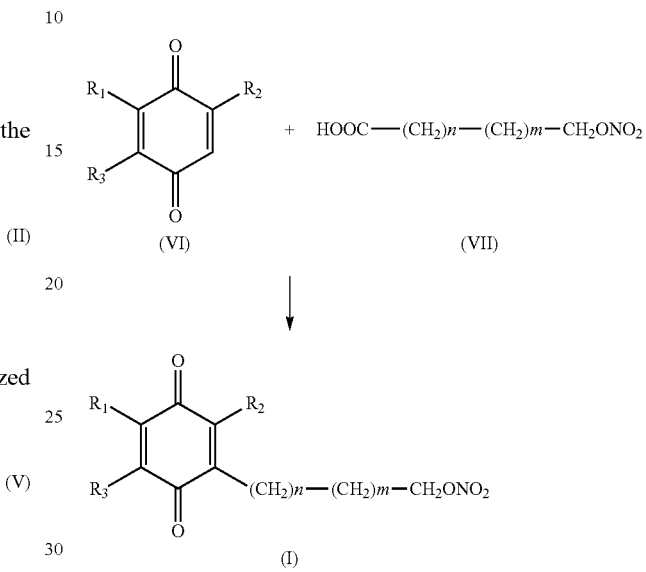

Compounds (VII) are known in the literature or they can be obtained by nitration reactions of the correspondent hydroxy acids of formula (VIIa) $HOOC$—$(CH_2)_n$—$(CH_2)_mCH_2$—OH or halogen acids of formula (VIIb) $HOOC$—$(CH_2)_n$—$(CH_2)_m$—$CH_2$-Hal by known reactions. Compounds (VIIa) and (VIIb) are commercially available or are made from known methods.

Compounds (VI) wherein $R_2$ is H or methyl and $R_1$ and $R_3$ are methoxy or $R_1$ and $R_3$ taken together form —CH=CH—CH=CH— are commercially available.

Compounds (VI) wherein $R_1$ and $R_2$ and $R_3$ are methyl are known in the literature and can be prepared from commercially available compounds (see for example Duveau D. Y. Bioor & Med Chemistry 2010, 18, 6429-6441) and Example 2).

Compounds (VI) wherein $R_2$ is methyl and $R_1$ and $R_3$ are different and are methyl or methoxy are known in the literature and can be prepared from commercially available compounds (see for example Duveau D. Y. Bioor & Med Chemistry 2010, 18, 6429-6441).

2. The compound of formula (I) wherein n, $R_1$, $R_2$ and $R_3$ are as above defined and Q is the group of formula (II)

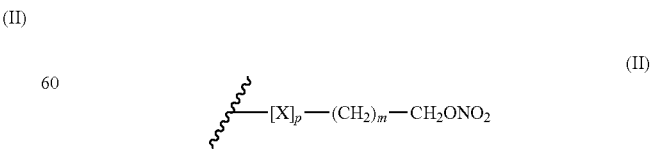

wherein p is 1, and X is O, can be synthesized by reacting a compound (VIII) with an halogen-alkyl-nitrate of formula (IX) Hal-$(CH_2)_m$—$ONO_2$, as depicted in the below scheme,

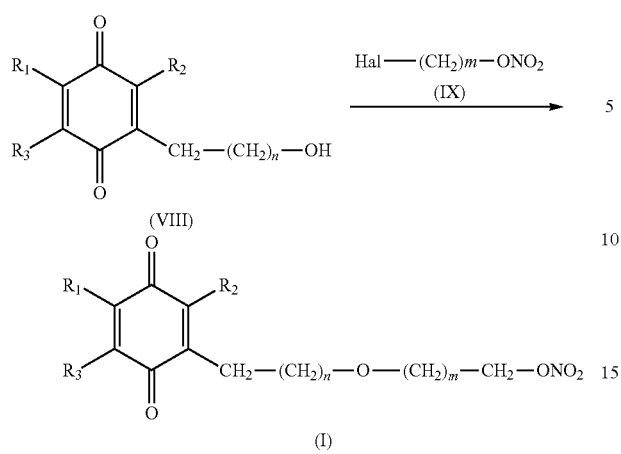
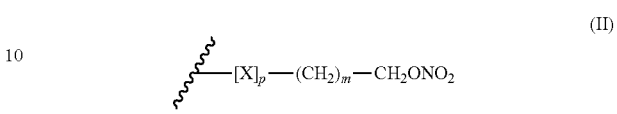

in the presence of a base, in an appropriated solvent such as acetonitrile, toluene, DMF at temperature ranging from 25 to 100° C. as known in the literature for the Williamson reaction.

[Compound (VIII) can be prepared as described above for compounds (V) wherein Y is —OH.]

2.1 Alternatively, the compound of formula (I) can be prepared by the following procedure:

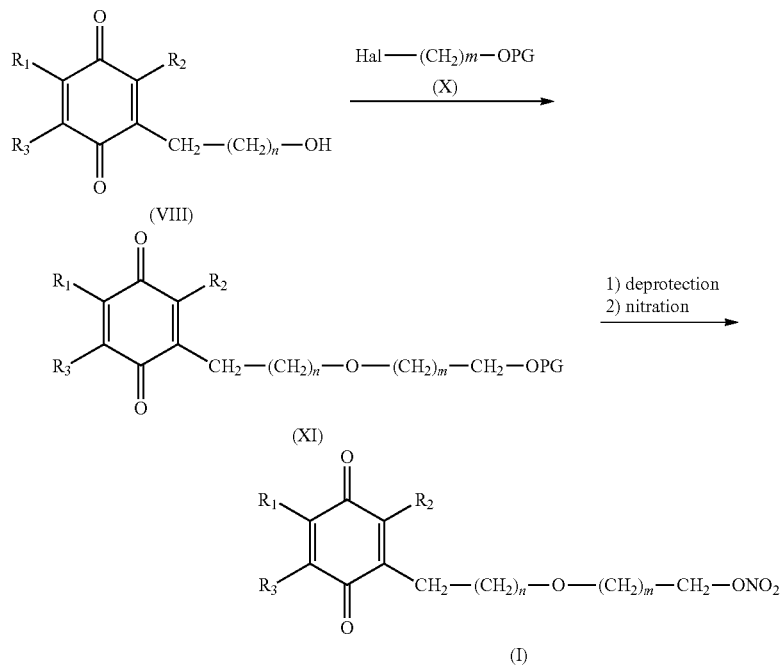

The compound (1) can be prepared by reacting a compound of formula (VIII) with a protected halogen-alkyl-alcohol of formula (X) wherein PG is an hydroxyl protective group such as dimethyl-tert-butylsilyl or other silyl derivative, the trityl group or the benzyl group, in the presence of a base in an appropriated solvent such as acetonitrile, toluene, DMF at temperature ranging from 25 to 100° C. as known in the literature for the Williamson reaction. The resulting quinone derivatives (XI) is converted to compound of formula (I) by deprotection and nitration with methods known in the literature.

Compounds of formula (VIII) are known in the literature or are made from methods described in the literature (Duveau D. Y. Bioor & Med Chemistry 2010, 18, 6429-6441)

3. Compounds of formula (I) wherein n, $R_1$, $R_2$ and $R_3$ are as above defined and Q is the group of formula (II)

$$\text{—[X]}_p\text{—(CH}_2)_m\text{—CH}_2\text{ONO}_2 \quad (II)$$

wherein m is 0, p is 1, and X is —CHONO$_2$ can be prepared by reacting a compound (VI) in the presence of salts of peroxydisulfuric acid like ammonium or potassium salts and AgNO$_3$ in an appropriate solvent such as acetonitrile or acetonitrile/water under reflux, as described for simple carboxylic acids by Breyer, S. and co-workers in Chem Med Chem, 2009, 4(5), 761-768 or by Duveau D, Y et al in Bioor & Med Chemistry 2010, 18, 6429-6441 or by Kayashima, Tomoko et al. in Bioor & Med Chemistry, 2010 18(10), 6305-6309 when the two groups $R_1$ and $R_3$ taken together form —CH=CH—CH=CH—).

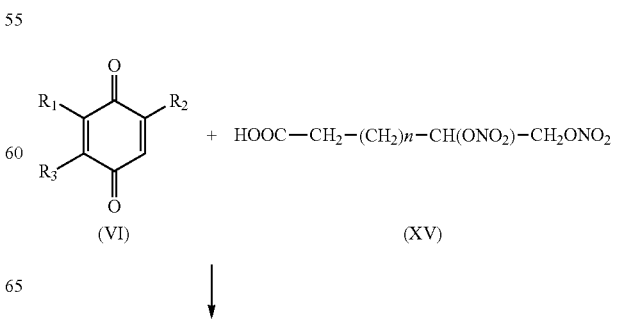

-continued

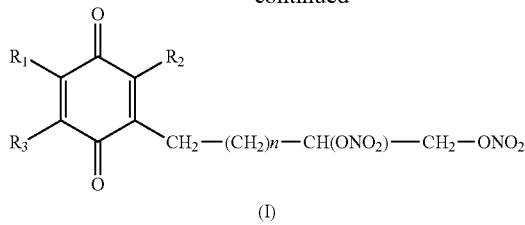

Compounds (XV) are known in the literature or they can be prepared by nitration reactions of the correspondent unsaturated acids of formula (XVI) HOOC—(CH$_2$)$_n$—CH=CH$_2$ by known reactions as for example by directly nitrating with I$_2$ and AgNO$_3$ or first converting the unsaturated acids of formula (XVI) to the diol (XVII) HOOC—(CH$_2$)$_n$—CHOH—CH$_2$OH and then nitrating with HNO$_3$ and acetic anhydride.

4. Compound of formula (I) wherein n, R$_1$, R$_2$ and R$_3$ are as above defined and Q is the group of formula (II)

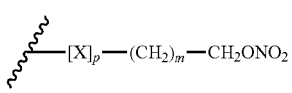

wherein p is 1, and X is S, can be prepared as depicted in the following scheme

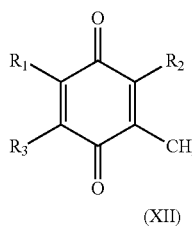

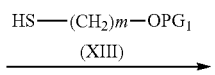

wherein Z is an halogen atom or the —O-mesyl or —O-tosyl groups and PG$_1$ is an hydroxyl protective group such as dimethyl-tert-butylsilyl or other silyl derivatives or the trityl group.

The compound (I) can be prepared by reacting a compound (XII) with a thiol compound of formula (XIII) with known methods depending on the meaning of Y. The resulting quinone derivative (XIV) is converted into compound of formula (I)) by known deprotection/nitration methods.

Compound (XII) are known in the literature or are made from methods described in the literature (Duveau D. Y. Bioor & Med Chemistry 2010, 18, 6429-6441).

5. The compound of formula (I) wherein n, R$_1$, R$_2$ and R$_3$ are as above defined and Q is the formula (III)

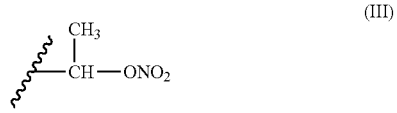

can be prepared according to the below depicted process:

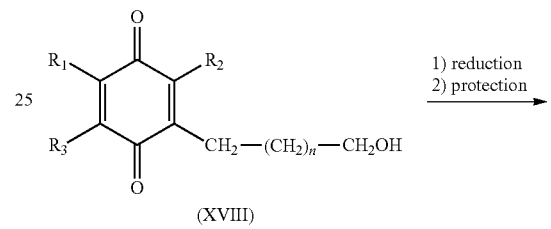

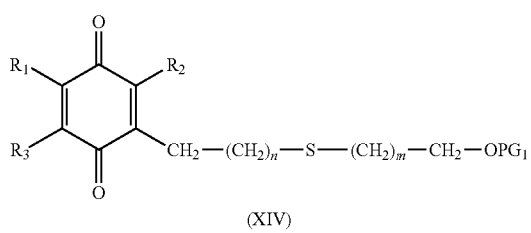

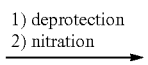

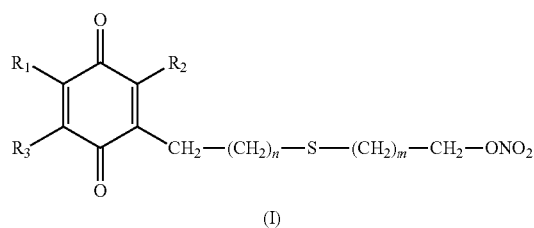

-continued

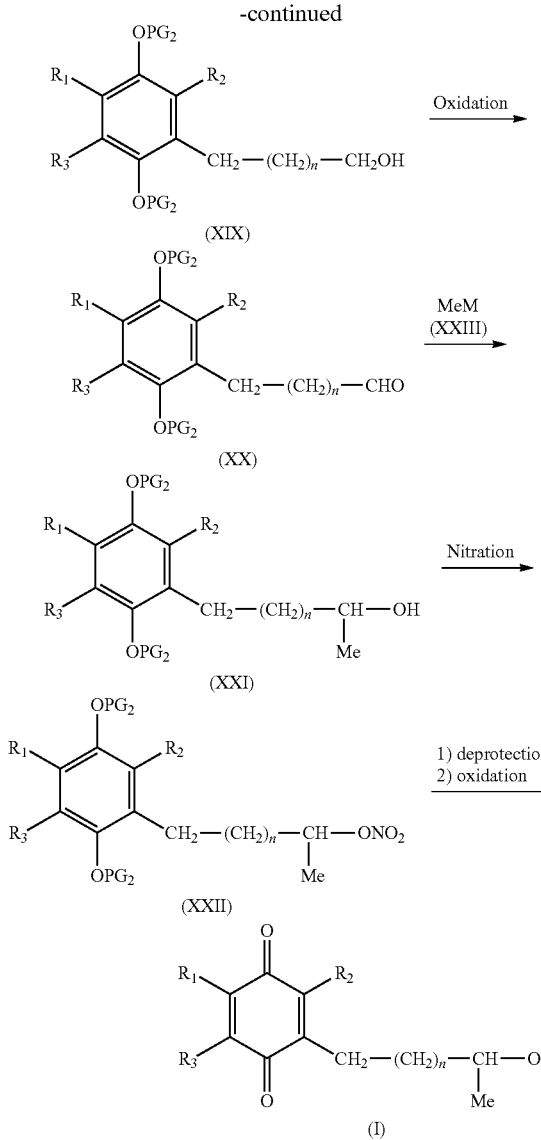

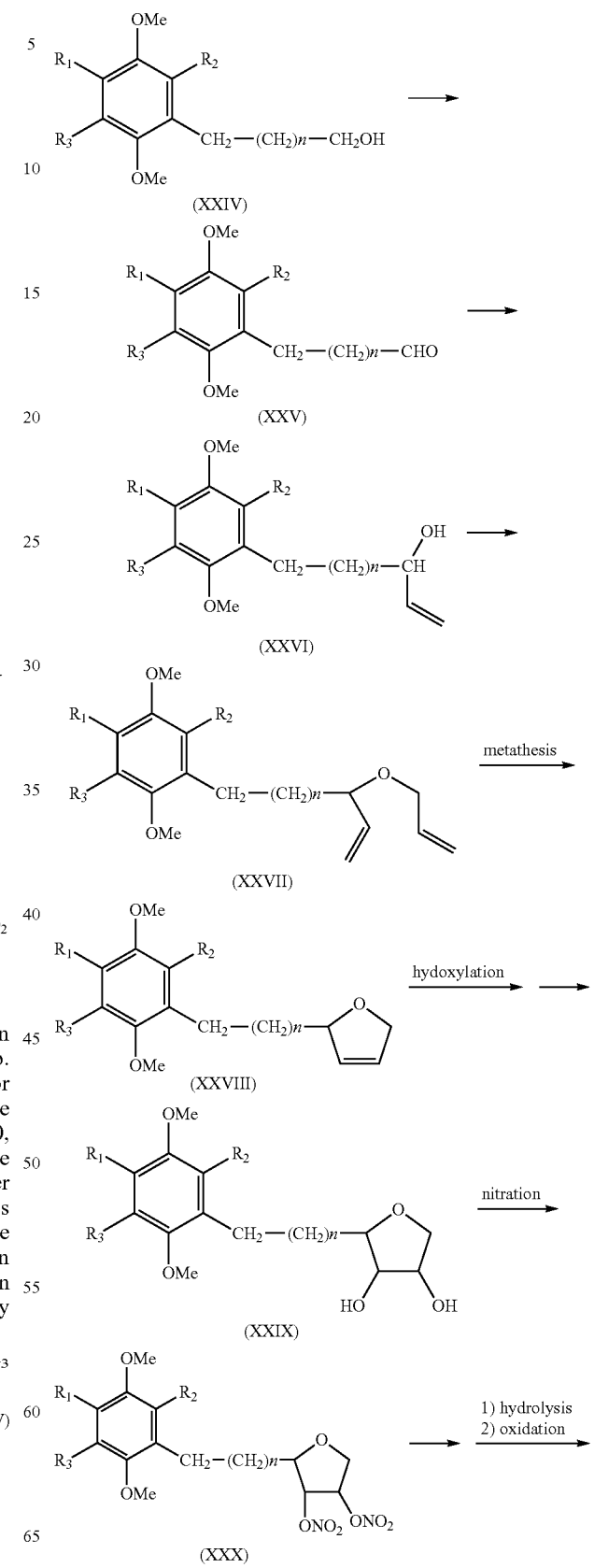

wherein $R_1$, $R_2$, $R_3$, n are as above defined and $PG_2$ is an oxygen protective group such as the methyl or the -boc group.

Compound (XVIII) are first reduced to phenols with, for example, $NaBH_4$ or dithionite as described in the literature (see for example Duveau D. Y. Bioor & Med Chemistry 2010, 18, 6429-6441). The hydroxyl groups of compound (XIX) are protected and then oxidized to aldehyde with PCC or other suitable alcohol oxidizing reagents. The aldehyde (XX) is alkylated with a compound MeM (XXIII) wherein M is the group —Li or —Mg and Hal is an halogen atom using known procedures. The alcohol (XXI) is then nitrated with known methods and the compound (XXII) is then deprotected by known methods.

6. The compound of formula (I) wherein n, $R_1$, $R_2$ and $R_3$ are as above defined and Q is the group of formula (IV)

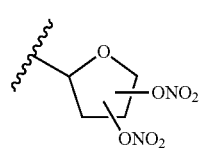

can be prepared as depicted in the following scheme:

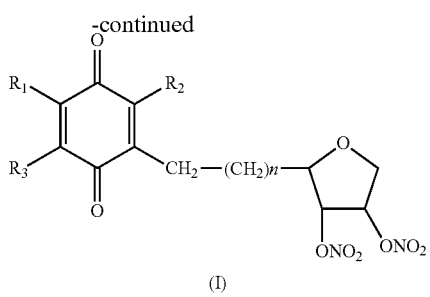

(I)

Compound (XXIV) is oxidized to compound (XXV) and then vinylated by known methods to obtained compound (XXVI). Compound (XXVII) is obtained by classic Williamson reaction and transformed into furan derivative (XXVIII) by known metathesis process. Compound (XXX) is prepared hydroxylation and nitration reaction of compound (XXVIII). Compounds (I) is obtained from hydrolysis and re-oxidation of compound (XXX).

Compounds (XXIV), wherein $R_1$, $R_2$, and $R_3$ are as above defined, are known in the literature or are prepared by known methods

EXAMPLE 1

Synthesis of 10-(4,5-dimethoxy-2-methyl-3,6-dioxo-cyclohexa-1,4-dienyl)decyl nitrate (Compound (6))

Compound (6)

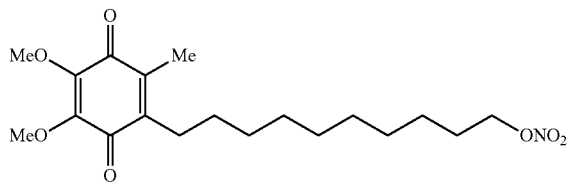

Method A

A dry 500 mL round bottom flask containing 2-(10-hydroxydecyl)-5,6-dimethoxy-3-methyl cyclohexa-2,5-diene-1,4-dione (7 g, 20.7 mmol), 2,6-di-tert-butyl-4-methylpyridine (6.37 g, 31 mmol, 1.5 eq) and tetrabutylammonium nitrate (7.5 g, 24.8 mmol, 1.2 eq) in dichloromethane (250 mL) was cooled to −70° C. and maintained at this temperature with stirring during the dropwise addition of a solution of triflic anhydride (4 mL, 24.8 mmol, 1.2 eq) in dichloromethane (30 mL). The reaction mixture was stirred at −70° C. for 2 h, and then allowed to warm to room temperature. The reaction mixture was washed with $H_2O$. The organic phase was dried over anhydrous sodium sulfate and the solvent removed in vacuum. The residue was purified by column chromatography (SNAP 340, gradient system from 4/6 ethyl acetate/n-hexane to 60/40 ethyl acetate/n-hexane) to give the titled compound as a reddish oil (6.0 g, 75%).

Method B

Step 1: Synthesis of 10-(4,5-dimethoxy-2-methyl-3, 6-dioxocyclohexa-1,4-dienyl)decyl methanesulfonate To a solution of 2-(10-hydroxydecyl)-5,6-dimethoxy-3-methyl cyclohexa-2,5-diene-1,4-dione (2.0 g, 5.91 mmol) and triethylamine (0.9 mL, 6.5 mmol, 1.1 eq) in dry $CH_2Cl_2$ (20 mL) was added at 0° C. a solution of methansulfonyl chloride (505 μL, 6.5 mmol, 1.1 eq) in $CH_2Cl_2$ (5 mL) followed by DMAP (10 mg). The reaction was left at room temperature for 16 hrs and then washed successively with water, saturated $NaHCO_3$, water and brine. The residue was purified by column chromatography (SNAP 100, gradient system from 20/80 ethyl acetate/n-hexane to 40/60 ethyl acetate/n-hexane in 10 CV) to give the title compound as an orange solid (2.21 g, 91%).

$^1H$ NMR (300 MHz, $CDCl_3$) δ 4.22 (t, J=6.6, 2H), 3.99 (s, 6H), 3.00 (s, 3H), 2.44 (t, J=7.2, 2H), 2.01 (s, 3H), 1.81-1.66 (m, 2H), 1.31 (m, 14H).

Step 2: Synthesis of 10-(4,5-dimethoxy-2-methyl-3, 6-dioxocyclohexa-1,4-dienyl)decyl nitrate To a stirred solution of 10-(4,5-dimethoxy-2-methyl-3,6-dioxocyclohexa-1,4-dienyl)decyl methanesulfonate (2.21 g, 5.3 mmol) in BuOAc/MeCN (3:1, 5 mL) was added tetrabutylammonium nitrate (0.32 g, 1.06 mmol, 0.2 eq) and sodium nitrate (0.68 g, 7.95 mmol, 1.5 eq). The reaction was heated at 80° C. for 18 h and then cooled down to RT. The reaction mixture was diluted with EtOAc and water. The organic layer was extracted, washed twice with water and then with brine, dried ($Na_2SO_4$), filtered and evaporated. The residue was purified by column chromatography (SNAP 100, gradient system from 40/60 ethyl acetate/n-hexane to 60/40 ethyl acetate/n-hexane) to give the titled compound as a reddish oil (1.81 g, 89%).

$^1H$ NMR (300 MHz, $CDCl_3$) δ 4.44 (t, J=6.6, 2H), 3.98 (s, 6H), 2.43 (d, J=7.2, 2H), 2.01 (s, 3H), 1.77-1.63 (m, 2H), 1.31 (m, 14H)

$^{13}C$ NMR (75 MHz, $CDCl_3$) δ 184.40, 183.92, 144.73, 144.66, 142.35, 138.62, 74.24, 61.10, 29.59, 29.25, 29.19, 28.98, 28.53, 26.47, 26.12, 25.50, 11.97.

EXAMPLE 2

Synthesis of 5-(2,4,5-trimethyl-3,6-dioxocyclohexa-1,4-dienyl)pentyl nitrate (Compound (1))

(1)

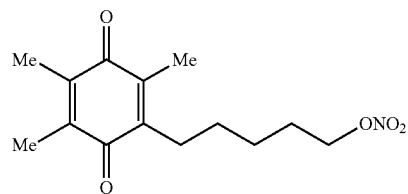

Step 1: Synthesis of 2,3,5-trimethyl-p-benzoquinone

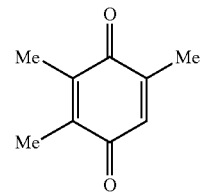

To a solution of trimethyl-p-hydroquinone (1.5 g; 6.57 mmol), (0.08 g; 0.33 mmol) and $H_2O_2$ 30% aq. (0.33 ml; 2.90 mmol) in MeOH (20 ml) cooled at 0° C., $H_2SO_4$ conc. (0.33 ml; 0.93 mmol) was added. The solution was stirred 1 hour at 0° C. and 2 hours at room temperature then was diluted with Et$_2$O (50 ml) and H$_2$O (50 ml). The two phases were separated and the aqueous layer was extracted with Et$_2$O (50 ml). The combined organic layers were washed with NaS$_2$O$_3$ sat. Solution (50 ml) and brine, dried on Na$_2$SO$_4$ and concentrated. The residue was purified by flash chromatography (Biotage SP1 instrument, SNAP 100 g column, Hex/EtAc 95:5, 10 CV) affording 0.70 g (yield: 71%) of the title compound as an orange solid.

$^1$H NMR (300 MHz, CDCl$_3$) δ 6.54 (s, 1H), 2.12-1.92 (m, 9H).

Step 2: Synthesis of 6-(nitrooxy)hexanoic acid

To a solution of 6-bromohexanoic acid (0.50 g; 2.56 mmol) in CH$_3$CN (10 ml), AgNO$_3$ (0.52 g; 3.07 mmol) was added. The solution was heated at the mw 20 minutes at 122° C. The salts were filtered off and the solvent evaporated. EtOAc was added and the salts were filtered off again, the solvent was evaporated affording 0.40 g (yield: 80%) of the title compound as a clear oil.

$^1$H NMR (300 MHz, CDCl$_3$) δ 4.46 (t, J=6.6, 2H), 2.39 (t, J=7.3, 2H), 1.91-1.60 (m, 4H), 1.56-1.38 (m, 2H).

Step 3: Synthesis of 5-(2,4,5-trimethyl-3,6-dioxocyclohexa-1,4-dienyl)pentyl nitrate To a solution of 2,3,5-trimethyl-p-benzoquinone (0.94 g, 6.28 mmol), 6-(nitrooxy)hexanoic acid (1.12 g, 6.28 mmol) and AgNO$_3$ (1.28 g, 7.54 mmol) in CH$_3$CN (50 ml) heated at 75° C., a solution of K$_2$S$_2$O$_8$ (2.04 g, 7.54 mmol) in H$_2$O (50 ml) was added dropwise. The reaction mixture was stirred at 75° C. for 5 hours, then it was allowed to cool to room temperature, and was poured in H$_2$O (50 ml). The product was extracted with EtOAc (2×30 ml). The combined organic layers were washed with NaHCO$_3$ sat. solution and brine, dried on Na$_2$SO$_4$ and concentrated. The residue was purified by flash chromatography (Biotage SP1 instrument, SNAP 100 g column, Hex/EtOAc 97:3, 10 cv, Hex/EtOAc 95:5 3 CV) affording 390 mg (yield: 22%) of the title compound as a yellow oil.

$^1$H NMR (300 MHz, CDCl$_3$) δ 4.45 (m, 2H), 2.48 (t, J=7.2, 2H), 2.11-1.92 (m, 9H), 1.87-1.66 (m, 2H), 1.53-1.35 (m, 4H).

EXAMPLE 3

Synthesis of 5-(4,5-dimethoxy-2-methyl-3,6-dioxo-cyclohexa-1,4-dienyl)pentyl nitrate (Compound (2))

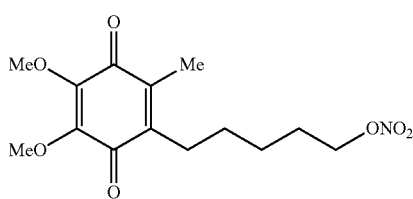

To a solution of 2,3-dimethoxy-5-methyl-p-benzoquinone (0.93 g, 5.12 mmol), 6-(nitrooxy)hexanoic acid (0.93 g, 5.12 mmol) (prepared as described in Example 2, Step 2) and AgNO$_3$ (1.04 g, 6.14 mmol) in CH$_3$CN (50 ml) heated at 75° C., a solution of K$_2$S$_2$O$_8$ (1.66 g, 6.14 mmol) in H$_2$O (50 ml) was added dropwise. The reaction mixture was stirred at 75° C. for 5 hours, then it was allowed to cool to room temperature, and was poured in H$_2$O (50 ml). The product was extracted with EtOAc (2×30 ml). The combined organic layers were washed with NaHCO$_3$ sat. solution and brine, dried on Na$_2$SO$_4$ and concentrated. The residue was purified by flash chromatography (Biotage SP1 instrument, SNAP 100 g column, EtOAc in Hex from 5% to 40% in 10 CV) affording 130 mg (yield: 8%) of the title compound as an orange oil.

$^1$H NMR (300 MHz, CDCl$_3$) δ 4.53-4.59 (m, 2H), 3.98 (s, 6H), 2.55-2.38 (m, 2H), 2.02 (s, 3H), 1.87-1.64 (m, 2H), 1.52-1.37 (m, 4H).

EXAMPLE 4

Synthesis of 5-(3-methyl-1,4-dioxo-1,4-dihydronaphthalen-2-yl)pentyl nitrate (Compound (12))

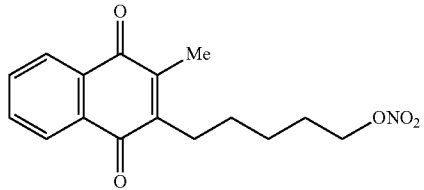

To a solution of 2-methyl-1,4-naphthoquinone (1.06 g, 6.15 mmol), 6-(nitrooxy)hexanoic acid (0.93 g, 5.12 mmol) and AgNO$_3$ (0.88 mg, 5.13 mmol) in CH$_3$CN (50 ml) heated at 75° C., a solution of K$_2$S$_2$O$_8$ (1.66 g, 6.15 mmol) in H$_2$O (50 ml) was added dropwise. The reaction mixture was stirred at 75° C. for 5 hours, was then allowed to cool to room temperature, and was poured in H$_2$O (50 ml). The product was extracted with EtOAc (2×30 ml). The combined organic layers were washed with NaHCO$_3$ saturated solution and brine, dried over Na$_2$SO$_4$ and concentrated. The residue was purified by flash chromatography (Biotage SP1 instrument, SNAP 100 g column, Hex:EtOAc 95:5, 5 CV and 90:10, 5 CV) affording 760 mg (Yield: 48%) of the title compound as a yellow oil.

1H NMR (300 MHz, CDCl$_3$) δ 8.19-8.02 (m, 2H), 7.77-7.62 (m, 2H), 4.53-4.38 (m, 2H), 2.75-2.53 (m, 2H), 2.20 (s, 3H), 1.88-1.66 (m, 4H), 1.64-1.41 (m, 4H).

EXAMPLE 5

In Vitro Antioxidant Activity (TBARS Test)

The antioxidant properties of compounds (6) (disclosed in example 1) and compound (23) (disclosed in example 19) and reference antioxidant compounds were assessed after NADPH-induced lipidic peroxidation of membrane lipids in rat hepatocytes using the detection of 2-thiobarbituric acid reactive substances (TBARS) by visible spectroscopy.

Hepatic microsomal membranes from male Wistar rats (200-250 g) were prepared by differential centrifugation (8000 g, 20 min; 120000 g, 1 h) in a HEPES/sucrose buffer (10 mM, 250 mM, pH 7.4) and stored at −80° C. Incubation was performed at 37° C. in a Tris-HCl/KCl (100 mM/150 mM, pH 7.4) containing microsomal membranes (2 mg prot/mL), sodium ascorbate (100 μM), and DMSO solutions of the tested compounds. Lipid peroxidation was initiated by adding ADP-FeCl₃ and NADPH (Method A) or 2.5 µM FeSO₄ (Method B) (as described by Boschi D. et al., J. Med. Chem. 2006, 49:2886-2897). Aliquots were taken from the incubation mixture at 5, 15, and 30 min and treated with trichloroacetic acid (TCA) 10% w/v. Lipid peroxidation was assessed by spectrophotometric (543 nm) determination of the TBARS consisting mainly of malondialdehyde (MDA). TBARS concentrations (expressed in nmol/mg protein) were obtained by interpolation with a MDA standard curve. The antioxidant activity of tested compounds was evaluated as the percent inhibition of TBARS production with respect to control samples, using the values obtained after 30 min of incubation. $IC_{50}$ values were calculated by nonlinear regression analysis.

The results reported in Table 1, showed that compound (6) ($IC_{50}$=2 µM) and (23) ($IC_{50}$=1.4 µM) proved to inhibit in a concentration-dependent manner the generation of TBARS with a potency ($IC_{50}$=2 µM) that is superior to well known antioxidant compounds as ferulic or caffeic acids, edavarone or melatonine.

TABLE 1

In vitro Antioxidant activity (TBARS test)

| Compound | Antioxidant activity IC50 µM (CL 95%) |
|---|---|
| Compound (6) | 2.0 (1.4-2.3) |
| Compound (23) | 1.4 (0.9-2.2) |
| Ferulic acid | 50.5 ± 0.4[§*] |
| Caffeic acid | 33 (32-34)[§] |
| Edavarone | 17 (15-18)[§a] |
| Idebenone | 1.6 (1.2-2.0) |
| Melatonin | 476 (442-512)[§b] |

[§]Method B;
[*]tested at 1 mM concentration;
[a]Chegaev, K. et al. J. Med. Chem. 2009, 52: 574-578:
[b]Chegaev, K. et al. J. Pineal Res. 2007, 42: 371-385

EXAMPLE 6

In Vitro NO-Mediated Activity

The ability of compound (6) disclosed in example 1, to induce in vitro vasorelaxation, which is a functional marker of NO release, was assessed on methoxamine-precontracted rabbit aortic rings.

Thoracic aortas from male New Zealand rabbits or male Sprague Dawley (SD) were used. The aortas were placed immediately in Krebs-HEPES buffer (pH 7.4; composition mM: NaCl 130.0, KCl 3.7, NaHCO3 14.9, KH2PO4 1.2, MgSO4.7H2O 1.2, Glucose 11.0, HEPES 10.0, CaCl2.2H2O 1.6). Connective tissue was removed and aortas were cut into ring segments (4-5 mm in length). Each ring was placed in a 5 mL tissue bath filled with Krebs-HEPES buffer (37° C.) aerated with 95% O2 and 5% CO2 and was attached to a force transducer (Grass FT03), connected to a BIOPAC MP150 System for measurement of the isometric tension. Preparations were allowed to equilibrate for 1 h at a resting tension of 2 g for rabbit aortas and 1 g for rat aortas with changes of the buffer every 15 min. Then the rings were stimulated by exposure to 90 mM KCl (3 times) with intervening washings.

Rabbit aorta. After equilibration, rabbit aortas were precontracted submaximally with methoxamine (3 µM) and, when the contraction was stable, acetylcholine (ACh, 3 µM) was added. A relaxant response to ACh indicated the presence of a functional endothelium. After washout, the rings were precontracted submaximally with methoxamine 3 µM. When a steady-state level of contraction was obtained, a cumulative concentration-response curve to the tested compounds (0.01-100 µM) was obtained in the presence of a functional endothelium.

Rat aorta. After equilibration, rat aortas were precontracted with KCl (90 mM) and, when the contraction was stable, a cumulative concentration-response curve to acetylcholine (ACh, 0.01-100 µM) was added. After washout, the rings were precontracted again with KCl (90 mM). When a steady-state level of contraction was obtained, a cumulative concentration-response curve to the tested compounds (0.01-100 µM) was obtained.

Data analysis. Results are given as mean±SEM. Vascular responses are expressed as percentage relaxation and plotted vs concentration. The sensitivity of isolated aorta to different vasodilators is expressed as the concentration that elicited 50% of the maximal responses (EC50). Responses are quantified in terms of EC50 and Emax (maximal vasodilating effect) values, obtained from the concentration-response curve by nonlinear curve fitting, using GraphPad software.

Compound (6) evoked concentration-dependent relaxation with $EC_{50}$=4.7±0.2 µM, achieving 89±1% relaxation at the highest concentration tested of 100 µM.

EXAMPLE 7

Effects of Compound 6 and isosorbide-5-mononitrate (5-ISMN) in Rat L-NAME-Induced Hypertension To assess the in vivo NO-dependent activity, Compound (6) was evaluated for systolic blood pressure (SBP) reduction efficacy in a rat model of NO-deprivation induced by L-NAME and compared with 5-ISMN.

Fasted male SD rats (250-300 g, n=3-5 per group), obtained from Harlan Italy (Correzzana, Milan, Italy), were orally treated with tested compounds or vehicle (DMSO: Methocel 1% 2/98 v/v) in a total volume of 4 ml/kg by gavage. At each time point (1, 3, 6 and 24 h) animals were deeply anesthetized with Zoletil® 100 (3 mg/kg), given intramuscularly. Thereafter, a pressure catheter (Samba Sensors, Harvard Apparatus, UK) was introduced into the common carotid artery for central blood pressure measurement. Pressure transducer was connected to a personal computer, in order to allow real time monitor of the pressure tracing. After 10 minutes of basal recording, L-NAME (50 mg/kg) was administered intraperitoneally and the effect on SBP monitored. When the SBP stabilized (5 minutes without variations) the recording was stopped. To further confirm that functional activity was NO-dependent, at each time point blood $^{15}$N-nitrite levels were measured following the procedure described in Example 12.

The results reported in Table 2 showed that intraperitoneal injection of L-NAME 50 mg/kg to anesthetized rats induced an increase of systolic blood pressure (SBP) of about 70 mmHg (from 129±5 to 197±9 mmHg). When orally administered, the reference NO-donor 5-ISMN (30 mg/kg) counteracted L-NAME induced hypertension until 3 hours after treatment, while Compound (6) (100 mg/kg) induced a more sustained effect, preventing such SBP increase over 6 hours after single oral administration in rats, indicating effective and prolonged systemic NO release. Surprisingly, even if compound (6) released less NO compared to 5-ISMN, as demonstrated by the 15N-nitrite blood levels shown in Table 2, it was able to induce a comparable efficacy on blood pressure.

TABLE 2

Effects of compound (6) and isosorbide-5-mononitrate (5-ISMN) in rat L-NAME-induced hypertension

| Time (hours) | Delta vs basal (mmHg) Vehicle | Delta vs basal (mmHg) 5-ISMN (30 mg/kg) | 15N-nitrite levels (µM) 5-ISMN (30 mg/kg) | Delta vs basal (mmHg) Comp. (6) (100 mg/kg) | 15N-nitrite levels (µM) Comp. (6) (100 mg/kg) |
|---|---|---|---|---|---|
| 1  | 67.8 ± 11.6 | 10.5 ± 6.1 | 11.0 ± 0.5  | 53.5 ± 4.5  | 1.3 ± 0.2 |
| 3  | 67.8 ± 11.6 | 6.5 ± 2.4  | 8.7 ± 0.7   | 14 ± 3.8    | 1.4 ± 0.4 |
| 6  | 67.8 ± 11.6 | 51.2 ± 5.7 | 6.5 ± 0.5   | 38 ± 3.6    | 1.1 ± 0.2 |
| 24 | 67.8 ± 11.6 | 83 ± 9     | 0.34 ± 0.06 | 67.7 ± 16.8 | 0.39 ± 0.1 |

EXAMPLE 8

In Vivo Tolerance Evaluation

To investigate whether the compound (6) induced nitrate tolerance, as observed for most of the drugs belonging to the nitrate class, the L-NAME-induced hypertension rat model described in Example 7 was performed following a repeated oral treatment. Rats were orally treated for 5 days with vehicle, compound (6) (100 mg/kg) or 5-ISMN (30 mg/kg). Compound (6) counteracted L-NAME-induced hypertension after 5-day oral treatment. Conversely, after 5-day treatment the reference nitrate 5-ISMN did not maintain its efficacy in preventing L-NAME-induced hypertension, suggesting the development of nitrate tolerance. The experiments were performed at the peak effect (1 hour for 5-ISMN and 3 hours for Compound (6)), results are reported in Table 3.

TABLE 3

In vivo tolerance evaluation

| Treatment | Delta vs basal (mmHg) Vehicle | Delta vs basal (mmHg) 5-ISMN (30 mg/kg) | Delta vs basal (mmHg) Comp. (6) (100 mg/kg) |
|---|---|---|---|
| acute    | 67.8 ± 11.6 | 10.5 ± 6.1 | 14 ± 3.8  |
| repeated | 67.8 ± 11.6 | 88 ± 11.5  | 27.8 ± 4  |

EXAMPLE 9

Ex Vivo Tolerance Evaluation

Tolerance to nitrate was further investigated assessing the vascular effects of Compound (6) following repeated treatment compared with 5-ISMN. The vascular response to the compound itself was assessed on isolated aortas from rats orally treated for 5 days with Compound (6) (100 mg/kg). The vascular response was performed as described in Example 6.

Arteries of animals treated with the compound (6) showed the same sensitivity to Compound (6) as those arteries of animals treated only with vehicle. On the contrary, the aortas from animals treated with the reference 5-ISMN (30 mg/kg) showed a reduced vascular response to 5-ISMN compared to control arteries, thus confirming the development of nitrate tolerance. Vascular responses were performed 1 h (ISMN) or 3 h (Compound (6)) after the last administration, the concentrations of tested compound that elicited the 50% of the maximal responses (EC50) are shown in Table 4.

TABLE 4

Ex vivo tolerance evaluation

| Treatment | $EC_{50}$ (µM) 5-ISMN (30 mg/kg) | $EC_{50}$ (µM) Compound (6) (100 mg/kg) |
|---|---|---|
| acute    | 20 ± 0.6 | 0.11 ± 0.02 |
| repeated | 127 ± 48 | 0.18 ± 0.02 |

EXAMPLE 10

Endothelial Dysfunction Evaluation

Endothelial-dependent vasodilation (vascular response to acetylcholine, ACh) was assessed following 5-day treatment with Compound (6) (100 mg/kg) or 5-ISMN (30 mg/kg). A relaxant response to ACh indicated the presence of a functional endothelium. The vascular response was performed as described in Example 6. The maximal vasodilating effect values (Emax) reported in Table 5, showed that Compound (6) did not modify endothelial-dependent vasorelaxation whereas 5-ISMN caused a reduced response to Ach.

TABLE 5

Endothelial-dependent vasodilation

| Treatment | % relaxation (Emax) 5-ISMN (30 mg/kg) | % relaxation (Emax) Comp. (6) (100 mg/kg) |
|---|---|---|
| acute    | 92.7 ± 4.3 | 89.6 ± 4.5 |
| repeated | 78.2 ± 9.2 | 84.3 ± 7.5 |

EXAMPLE 11

Pharmacokinetic (PK) Profile in Mice

The absorption and in vivo NO-donating property of the compounds of the invention were assessed by the evaluation of blood $^{15}$N-nitrite levels following oral administration.

Tested Compounds:

10-(4,5-dimethoxy-2-methyl-3,6-dioxocyclohexa-1,4-dienyl)decyl nitrate-nitrogen-15 which correspond to compound (6) containing nitrogen-15 ($^{15}$N-Compound (6));

5-isorbide mononitrate containing nitrogen-15 (5-ISM$^{15}$N)

Male CD1 mice (n=3/time point) were orally treated with $^{15}$N-Compound (6) at 100 mg/kg or 5-ISM$^{15}$N (30 mg/kg). At each time point (5, 10, 15, 30, 60, 120, 240, 360, 480 and 1440 min) blood was taken by cardiac puncture using heparin to avoid blood clotting. Blood samples were immediately protein crushed. Samples were analyzed by LC-MS/MS. $^{15}$N-nitrite levels following oral administration of Compound (6) (100 mg/kg) or 5-ISM$^{15}$N (30 mg/kg) in CD1 mice are reported in Table 6.

TABLE 6

| | $^{15}$N-nitrite levels in CD1 mice | | |
|---|---|---|---|
| Test compound | Cmax (microM) | Tmax (min) | AUC$_{0-24}$ (microM * min) |
| $^{15}$N-Compound (6) | 3.1 ± 0.3 | 30 | 1225 |
| 5-ISM$^{15}$N | 27.5 ± 3 | 30 | 2758 |

EXAMPLE 12

Pharmacokinetic (PK) Profile in Rats

The absorption and in vivo NO-donating property of the compounds of the invention were assessed by the evaluation of blood $^{15}$N-nitrite levels following oral administration.
Tested Compounds:
5-(2,4,5-trimethyl-3,6-dioxocyclohexa-1,4-dienylpentyl nitrate-nitrogen-15 which corresponds to compound (1) containing nitrogen-15 ($^{15}$N-Compound (1));
5-(4,5-dimethoxy-2-methyl-3,6-dioxocyclohexa-1,4-dienyl)pentyl nitrate-nitrogen-15 which corresponds to compound (2) containing nitrogen-15 ($^{15}$N-Compound (2));
4-(2,4,5-trimethyl-3,6-dioxocyclohexa-1,4-dienyl)butyl nitrate-nitrogen-15 which corresponds to compound (3) containing nitrogen-15 ($^{15}$N-Compound (3));
4-(4,5-dimethoxy-2-methyl-3,6-dioxocyclohexa-1,4-dienyl)butyl nitrate-nitrogen-15 which corresponds to compound (4) containing nitrogen-15 ($^{15}$N-Compound (4));
10-(2,4,5-trimethyl-3,6-dioxocyclohexa-1,4-dienyl)decyl nitrate-nitrogen-15 which corresponds to compound (5) containing nitrogen-15 ($^{15}$N-Compound (5));
10-(4,5-dimethoxy-2-methyl-3,6-dioxocyclohexa-1,4-dienyl)decyl nitrate-nitrogen-15 which corresponds to compound (6) containing nitrogen-15 ($^{15}$N-Compound (6));
3-(3-(4,5-dimethoxy-2-methyl-3,6-dioxocyclohexa-1,4-dienyl)propoxy)propyl nitrate-nitrogen-15 which corresponds to compound (14) containing nitrogen-15 ($^{15}$N-Compound (14));
6-(2,4,5-trimethyl-3,6-dioxocyclohexa-1,4-dienyl)hexyl nitrate-nitrogen-15 which corresponds to compound (15) containing nitrogen-15 ($^{15}$N-Compound (15));
6-(4,5-dimethoxy-2-methyl-3,6-dioxocyclohexa-1,4-dienyl)hexyl nitrate-nitrogen-15 which corresponds to compound (16) containing nitrogen-15 ($^{15}$N-Compound (16));
11-(4,5-dimethoxy-2-methyl-3,6-dioxocyclohexa-1,4-dienyl)-undecane-1,2-diyl dinitrate-nitrogen-15 which corresponds to compound (17) containing nitrogen-15 ($^{15}$N-Compound (17));
8-(5-methoxy-2,4-dimethyl-3,6-dioxocyclohexa-1,4-dienyl)octyl nitrate-nitrogen—which corresponds to compound (19) containing nitrogen-15 ($^{15}$N-Compound (19));
2-(3-(4,5-dimethoxy-2-methyl-3,6-dioxocyclohexa-1,4-dienyl)propoxy)ethyl nitrate-nitrogen-15 which corresponds to compound (20) containing nitrogen-15 ($^{15}$N-Compound (20));
6-(3-methyl-1,4-dioxo-1,4-dihydronaphthalen-2-yl)hexyl nitrate-nitrogen-15 which corresponds to compound (23) containing nitrogen-15 ($^{15}$N-Compound (23));
3-(3-(3-methyl-1,4-dioxo-1,4-dihydronaphthalen-2-yl)propoxy)propyl nitrate-nitrogen-15 which corresponds to compound (25) containing nitrogen-15 ($^{15}$N-Compound (25));
6-(5-methoxy-2,4-dimethyl-3,6-dioxocyclohexa-1,4-dienyl)hexyl nitrate-nitrogen-15 which corresponds to compound (28) containing nitrogen-15 ($^{15}$N-Compound (28));
6-(4-methoxy-2,5-dimethyl-3,6-dioxocyclohexa-1,4-dienyl)hexyl nitrate-nitrogen-15 which corresponds to compound (29) containing nitrogen-15 ($^{15}$N-Compound (29));
8-(4-methoxy-2,5-dimethyl-3,6-dioxocyclohexa-1,4-dienyl)octyl nitrate-nitrogen-15 which corresponds to compound (32) containing nitrogen-15 ($^{15}$N-Compound (32));
8-(2,4,5-trimethyl-3,6-dioxocyclohexa-1,4-dienyl)octyl nitrate-nitrogen-15 which corresponds to compound (34) containing nitrogen-15 ($^{15}$N-Compound (34));
5-isorbide mononitrate containing nitrogen-15 (5-ISM$^{15}$N).

Cannulated SD rats were orally treated with $^{15}$N-Compounds (6) at 30 mg/kg, 5-ISM$^{15}$N (30 mg/kg), or $^{15}$N-Compounds (1)-(5), (14)-(17), (19), (20), (23), (25), (28), (29), (32), (34) at 30 mg/kg. At each time point (5, 10, 15, 30, 60, 180, 360 and 1440 min) blood was taken using heparin to avoid blood clotting. Blood samples were immediately protein crushed. Samples were analyzed by LC-MS/MS.

In Table 7 are reported $^{15}$N-nitrite blood levels following oral administration of SD rats with 5-ISM$^{15}$N (30 mg/kg) or with $^{15}$N-labeled corresponding compounds of the invention (30 mg/kg).

All the compounds are able to release nitric oxide after oral administration in a range (Cmax) that was seen to be able to counteract L-NAME induced hypertension without the development of the phenomenon of tolerance to nitrates.

TABLE 7

| | $^{15}$N-nitrite levels in rats | | |
|---|---|---|---|
| Test compound | Cmax (microM) | Tmax (min) | AUC$_{0-24}$ (microM * min) |
| $^{15}$N-Compound (1) | 3.35 ± 0.42 | 60 | 1248 |
| $^{15}$N-Compound (2) | 1.92 ± 0.25 | 60 | 1139 |
| $^{15}$N-Compound (3) | 4.82 ± 1.10 | 60 | 1404 |
| $^{15}$N-Compound (4) | 3.33 ± 0.1 | 15 | 832 |
| $^{15}$N-Compound (5) | 1.89 ± 0.42 | 180 | 1496 |
| $^{15}$N-Compound (6) | 2.6 ± 0.2 | 180 | 2469 |
| $^{15}$N-Compound (14) | 1.52 ± 0.11 | 60 | 694 |
| $^{15}$N-Compound (15) | 3.65 ± 0.58 | 180 | 2135 |
| $^{15}$N-Compound (16) | 2.93 ± 0.49 | 180 | 1559 |
| $^{15}$N-Compound (17) | 2.06 ± 0.12 | 180 | 1666 |
| $^{15}$N-Compound (19) | 3.16 ± 0.32 | 60 | 1873 |
| $^{15}$N-Compound (20) | 3.58 ± 0.72 | 60 | 1154 |
| $^{15}$N-Compound (23) | 4.05 ± 0.53 | 180 | 2586 |
| $^{15}$N-Compound (25) | 2.89 ± 0.69 | 180 | 2010 |
| $^{15}$N-Compound (28) | 3.74 ± 0.42 | 60 | 1199 |
| $^{15}$N-Compound (29) | 2.55 ± 0.22 | 60 | 1309 |
| $^{15}$N-Compound (32) | 1.98 ± 0.57 | 180 | 1892 |
| $^{15}$N-Compound (34) | 2.80 ± 0.25 | 180 | 1477 |
| 5-ISM$^{15}$N | 20.6 ± 4.2 | 60 | 7399 |

EXAMPLE 13

Synthesis of 6-(2,4,5-trimethyl-3,6-dioxocyclohexa-1,4-dienyl)hexyl nitrate (Compound (15))

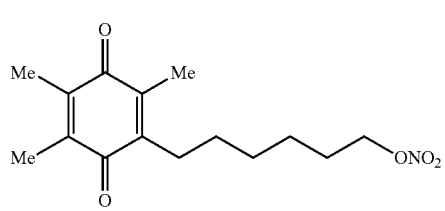

(15)

Step 1: Synthesis of Ethyl 7-(nitrooxy)heptanoate

To a solution of Ethyl 7-bromoheptanoate (1.40 g; 6.00 mmol) in $CH_3CN$ (20 ml), $AgNO_3$ (1.23 g; 7.20 mmol) was added. The solution was heated at the mw 22 minutes at 120° C. The salts were filtered off and the solvent evaporated. EtOAc was added and the salts were filtered off again, the solvent was evaporated affording 1.3 g (yield: 100%) of the title compound as a clear oil.

$^1$H NMR (300 MHz, $CDCl_3$) δ 4.44 (t, 2H), 4.13 (q, 2H), 2.44-2.21 (m, 2H), 1.82-1.54 (m, 4H), 1.54-1.31 (m, 4H), 1.31-1.16 (m, 3H).

Step 2: Synthesis of 7-(nitrooxy)heptanoic acid

To a solution of Ethyl 7-(nitrooxy)heptanoate (1.3 g; 6.0 mmol) cooled at 4° C., a solution of LiOH 2M (7.5 ml; 15.0 mmol) was added dropwise. The solution was stirred at 4° C. overnight then was acidified with HCl 3N until pH=1 and the product was extracted with $CH_2Cl_2$ (5×20 ml). The combined organic layers were dried on $Na_2SO_4$ and concentrated affording 0.91 g (Yield: 79%) of a clear oil.

$^1$H NMR (300 MHz, $CDCl_3$) δ 4.45 (t, 2H), 2.37 (t, 2H), 1.84-1.54 (m, 4H), 1.54-1.32 (m, 4H).

Step 3: Synthesis of 6-(2,4,5-trimethyl-3,6-dioxocyclohexa-1,4-dienyl)hexyl nitrate To a solution of 2,3,5-trimethyl-p-benzoquinone (0.71 g, 4.71 mmol), 7-(nitrooxy)heptanoic acid (0.91 g, 4.71 mmol) and $AgNO_3$ (0.80 g, 4.71 mmol) in $CH_3CN$ (20 ml) heated at 75° C., a solution of $K_2S_2O_8$ (1.27 g, 4.71 mmol) in $H_2O$ (20 ml) was added dropwise. The reaction mixture was stirred at 75° C. for 3 hours, then it was allowed to cool to room temperature, and was poured in $H_2O$ (20 ml). The product was extracted with EtOAc (2×15 ml). The combined organic layers were washed with $NaHCO_3$ sat. solution and brine, dried on $Na_2SO_4$ and concentrated. The residue was purified by flash chromatography (Biotage SP1 instrument, SNAP 50 g column, Hex/EtOAc 97:3, 20 cv) affording 560 mg (yield: 40%) of the title compound as a yellow oil.

$^1$H NMR (300 MHz, $CDCl_3$) δ 4.44 (t, 2H), 2.56-2.37 (m, 2H), 2.01 (s, 9H), 1.81-1.64 (m, 2H), 1.50-1.37 (m, 6H).

EXAMPLE 14

Synthesis of 4-(2,4,5-trimethyl-3,6-dioxocyclohexa-1,4-dienyl)butyl nitrate (Compound (3))

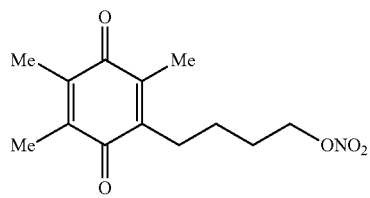

(3)

Step 2: Synthesis of Ethyl-5-(nitrooxy)valerate

To a solution of Ethyl 5-bromovalerate (0.63 g; 3.00 mmol) in $CH_3CN$ (10 ml), $AgNO_3$ (0.61 g; 3.6 mmol) was added. The solution was heated at the mw 22 minutes at 120° C. The salts were filtered off and the solvent evaporated. EtOAc was added and the salts were filtered off again, the solvent was evaporated affording 0.55 g (yield: 96%) of the title compound as a clear oil.

$^1$H NMR (300 MHz, $CDCl_3$) δ 4.53-4.38 (m, 2H), 4.14 (q, 2H), 2.45-2.24 (m, 2H), 1.85-1.64 (m, 4H), 1.26 (q, 3H).

Step 3: Synthesis of 5-(nitrooxy)pentanoic acid

To a solution of Ethyl-5-(nitrooxy)valerate (0.55 g; 2.87 mmol) cooled at 4° C., a solution of LiOH 2N (4.0 ml; 7.50 mmol) was added dropwise. The solution was stirred at 4° C. overnight then was acidified with HCl 3N until pH=1 and the product was extracted with $CH_2Cl_2$ (5×15 ml). The combined organic layers were dried on $Na_2SO_4$ and concentrated affording 0.47 g (Yield: 100%) of a clear oil $^1$H NMR (300 MHz, $CDCl_3$) δ 4.47 (t, 2H), 2.54-2.37 (m, 2H), 1.94-1.63 (m, 4H).

Step 4: Synthesis of 4-(2,4,5-trimethyl-3,6-dioxocyclohexa-1,4-dienyl)butyl nitrate To a solution of 2,3,5-trimethyl-p-benzoquinone (0.50 g, 3.34 mmol), 5-(nitrooxy)pentanoic acid (0.47 g, 2.87 mmol) and $AgNO_3$ (0.57 g, 3.34 mmol) in $CH_3CN$ (20 ml) heated at 75° C., a solution of $K_2S_2O_8$ (1.08 g, 4.01 mmol) in $H_2O$ (20 ml) was added dropwise. The reaction mixture was stirred at 75° C. for 3 hours, then it was allowed to cool to room temperature, and was poured in $H_2O$ (20 ml). The product was extracted with EtOAc (2×15 ml). The combined organic layers were washed with $NaHCO_3$ sat. solution and brine, dried on $Na_2SO_4$ and concentrated. The residue was purified by flash chromatography (Biotage SP1 instrument, SNAP 50 g column, Hex/EtOAc 97:3, 15 cv) affording 220 mg (yield: 24%) of the title compound as a yellow oil.

$^1$H NMR (300 MHz, $CDCl_3$) δ 4.47 (t, 2H), 2.61-2.44 (m, 2H), 2.01 (s, 9H), 1.86-1.68 (m, 2H), 1.61-1.42 (m, 2H).

EXAMPLE 15

Synthesis of 5-(2,4,5-trimethyl-3,6-dioxocyclohexa-1,4-dienyl)pentane-1,2-diyl dinitrate (Compound (10))

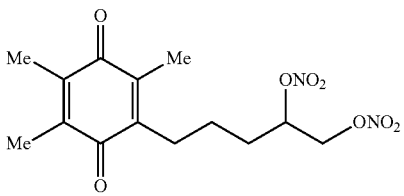

(10)

Step 1: Synthesis of 4-nitrophenyl hex-5-enoate

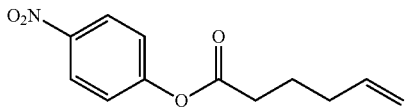 [SMILES: C=CCCCC(=O)Oc1ccc([N+](=O)[O-])cc1]

To a solution of 4-Nitrophenol (2.0 g; 14.38 mmol) and 5-hexenoic acid (1.7 ml; 14.38 mmol) in $CH_2Cl_2$ (30 ml) cooled at 0° C., Dimethylaminopropyl n-Ethyl Carbodiimide Hydrochloride (EDAC) (3.3 g, 17.26 mmol) and Dimethylaminopyridine (DMAP) (0.35 g; 2.88 mmol) were added portionwise. The mixture was stirred two hours at rt then was washed with a 5% solution of $NaH_2PO_4$ (30 ml), $H_2O$ (20 ml) and brine (20 ml). The organic layer was dried on $Na_2SO_4$ and concentrated affording 3.2 g (quantitative yield) of the title compound as a brown oil which was used without any further purification.

Step 2: Synthesis of 4-nitrophenyl 5,6-bis(nitrooxy)hexanoate

To a solution of 4-nitrophenyl hex-5-enoate (1.0 g; 4.25 g) in $CH_3CN$ (20 ml) cooled at −10° C., $AgNO_3$ (0.87 g; 5.1 mmol) and $I_2$ (1.3 g; 5.1 mmol) were added. The mixture was stirred 20 minutes at −10° C. then $AgNO_3$ (1.3 g; 7.65 mmol) was added and the mixture was heated at 75° C. for 24 hours. The salts were filtered off and the solvent evaporated. EtOAc (30 ml) was added, the salts filtered again and the solvent evaporated affording 1.1 g of the title compound which was used without any further purification.

Step 3: Synthesis of 5,6-bis(nitrooxy)hexanoic acid

To a solution of 4-nitrophenyl 5,6-bis(nitrooxy)hexanoate (1.1 g; 3.04 mmol) in THF/EtOH (2:1; 15 ml) cooled at 0° C., NaOH 2N (4.6 ml; 9.12 mmol) was added dropwise. The solution was stirred 30 minutes at 0° C., then the solvent was removed. $CH_2Cl_2$ (10 ml) and $H_2O$ (10 ml) were added to the residue, fum. HCl was added until pH=1. The two phases were separated and the organic one was extracted with $CH_2Cl_2$ (2×10 ml). The combined organic layers were dried on $Na_2SO_4$ and concentrated affording 470 mg of the title compound which was used without any further purification.

$^1$H NMR (300 MHz, $CDCl_3$) δ 5.40-5.19 (m, 1H), 4.83-4.68 (m, 1H), 4.57-4.40 (m, 1H), 2.54-2.35 (m, 2H), 1.94-1.66 (m, 4H).

Step 4: Synthesis of 5-(2,4,5-trimethyl-3,6-dioxocyclohexa-1,4-dienyl)pentane-1,2-diyl dinitrate To a solution of 2,3,5-trimethyl-p-benzoquinone (0.29 g, 1.96 mmol), 5,6-bis(nitrooxy)hexanoic acid (0.47 g, 1.96 mmol) and $AgNO_3$ (0.33 g, 1.96 mmol) in $CH_3CN$ (10 ml) heated at 75° C., a solution of $K_2S_2O_8$ (0.53 g, 1.96 mmol) in $H_2O$ (10 ml) was added dropwise. The reaction mixture was stirred at 75° C. for 3 hours, then it was allowed to cool to room temperature, and was poured in $H_2O$ (10 ml). The product was extracted with EtOAc (2×10 ml). The combined organic layers were washed with $NaHCO_3$ saturated solution and brine, dried on $Na_2SO_4$ and concentrated. The residue was purified by flash chromatography (Biotage SP1 instrument, SNAP 50 g column, Hex/EtOAc 90:10, 15 cv) affording 266 mg (yield: 39%) of the title compound as a yellow oil.

$^1$H NMR (300 MHz, $CDCl_3$) δ 5.46-5.25 (m, 1H), 4.82-4.67 (m, 1H), 4.57-4.39 (m, 1H), 2.53 (t, 2H), 2.08-1.95 (m, 9H), 1.89-1.66 (m, 2H), 1.66-1.45 (m, 2H).

EXAMPLE 16

Synthesis of 3-(4,5-dimethoxy-2-methyl-3,6-dioxo-cyclohexa-1,4-dienyl)propyl nitrate (Compound (8))

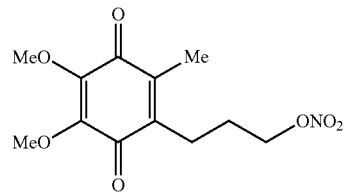

(8)

Step 1: Synthesis of 4,5-dimethoxy-2-methyltricyclo[6.2.1.0²,⁷]undeca-4,9-diene-3,6-dione To a solution of 2,3-dimethoxy-5-methyl-p-benzoquinone (4.0 g, 21.96 mmol) in glacial acetic acid (100 mL) was added freshly distilled cyclopentadiene (2.8 mL, 32.94 mmol, 1.5 eq) and the reaction was stirred overnight at r.t. The reaction was cooled to 0° C. and ice/water was added. The aqueous layer was neutralized using 3M aq NaOH and extracted with ethyl acetate (3×50 mL). The combined organic layers were washed with water, brine, dried on $Na_2SO_4$, filtered and evaporated affording the title compound (5.4 g, yield: 98%) as a dark red oil.

$^1$H NMR (300 MHz, $CDCl_3$) δ 6.16 (dd, J=5.6, 2.9, 1H), 6.01 (dd, J=5.6, 2.8, 1H), 3.94 (s, 3H), 3.92 (s, 3H), 3.42 (s, 1H), 3.08 (s, 1H), 2.83 (d, J=3.9, 1H), 2.07 (d, J=12.6, 3H), 1.71-1.62 (m, 1H), 1.54 (dt, J=9.2, 1.6, 1H).

Step 2: Synthesis of 2-allyl-4,5-dimethoxy-7-methyl-tricyclo[6.2.1.0²,⁷]-undeca-4,9-diene-3,6-dione To a stirred solution of crude 4,5-dimethoxy-2-methyltricyclo[6.2.1.0²,⁷]undeca-4,9-diene-3,6-dione (5.4 g) in dry THF (100 mL) cooled to 0° C. was added portionwise potassium tert-butoxide (4.0 g, 32.9 mmol, 1.5 eq). The reaction became dark reddish and was stirred at this temperature for another 30 mins then a solution of allyl bromide (2.9 mL, 35.1 mmol, 1.6 eq) in dry THF (30 mL) was added slowly. The reaction was stirred for 2 h before addition of water (30 mL). The aqueous layer was acidified to pH 2 and the solution was extracted with Et2O (3×50 mL). The combined organic layers were washed with water and brine, dried on sodium sulfate, filtered and evaporated. The residue was purified by flash chromatography (Biotage instrument, SNAP 340 column, EtOAc in Hex from 20% to 40% in 10 CV) affording the title compound as a pale yellow oil (4.22 g, yield: 67%).

$^1$H NMR (300 MHz, CDCl$_3$) δ 6.05 (d, J=6.1, 2H), 5.90-5.69 (m, 1H), 5.10 (s, 1H), 5.05 (dd, J=3.6, 2.1, 1H), 3.94-3.87 (m, 5H), 3.12 (d, J=1.6, 1H), 3.05-2.99 (m, 1H), 2.70 (dd, J=14.5, 7.6, 1H), 2.56 (dd, J=14.5, 6.7, 1H), 1.76 (m, 1H), 1.50 (s, 3H), 1.49 (s, 1H).

Step 3: Synthesis of 2-Allyl-3-methyl-5,6-dimethoxy-1,4-benzoquinone

A solution of 2-allyl-4,5-dimethoxy-7-methyltricyclo [6.2.1.0$^{2,7}$]-undeca-4,9-diene-3,6-dione (4.1 g, 14.22 mmol) in toluene (50 mL) was heated at reflux for 7 h. The reaction was then cooled down and the solvent evaporated. The residue was purified by flash chromatography (Biotage instrument, SNAP 340 column, EtOAc in Hex from 20% to 40% in 10 CV) affording the title compound as a red oil (4.22 g, yield: 67%).

$^1$H NMR (300 MHz, CDCl$_3$) δ 5.83-5.65 (m, 1H), 5.07 (dd, J=3.9, 1.5, 1H), 5.02 (dd, J=3.6, 1.6, 1H), 3.99 (d, J=1.1, 5H), 3.23 (t, J=6.7, 2H), 2.08-1.96 (m, 3H).

Step 4: Synthesis of 1-Allyl-2,3,4,5-tetramethoxy-6-methyl benzene

To a stirred solution of 2-Allyl-3-methyl-5,6-dimethoxy-1,4-benzoquinone (27 g, 121.5 mmol) and tetrabutylammonium bromide (2.0 g) in THF/water (1/1, 700 mL each) was added sodium dithionite (211 g, 1.215 mole, 10 eq). The reaction was stirred for 30 min then cooled to 0° C. and NaOH (73 g, 15 eq). After 30 min of stirring, methyl iodide (100 mL, 1.215 mole, 10 eq) was added and the reaction heated overnight at 40° C. The reaction was diluted with water (1 L) and extracted 3 times with Et2O (500 mL each). The combined organic layers were washed with water and brine, dried on sodium sulfate, filtered and evaporated. The residue was purified by flash chromatography (Biotage SP4, 3 SNAP 340 columns, EtOAc in Hex from 5% to 20% in 10 CV) affording the title compound as a colourless oil (19.7 g, yield: 64%).

$^1$H NMR (300 MHz, CDCl$_3$) δ 5.91 (ddt, J=16.0, 10.2, 5.8, 1H), 5.04-4.97 (m, 1H), 4.92 (dq, J=17.1, 1.8, 1H), 3.92 (s, 3H), 3.90 (s, 3H), 3.80 (s, 3H), 3.78 (s, 3H), 3.38 (dt, J=5.8, 1.8, 2H), 2.18 (s, 3H).

Step 5: Synthesis of 1-(3-Hydroxypropyl)-2,3,4,5-tetramethoxy-6-methylbenzene To a stirred solution of 1-allyl-2,3,4,5-tetramethoxy-6-methylbenzene (6.8 g, 26.95 mmol) in dry THF (100 mL) was added at 0° C. a 0.5 M solution of 9-BBN in THF (108 mL, 53.9 mmol, 2 eq). The reaction was stirred for 16 h at rt. The reaction was cooled to 0° C. and simultaneously were added a 3M aqueous NaOH solution (44.1 mL) and a 30% aqueous H$_2$O$_2$ solution (44.1 mL). The reaction was stirred for 30 min then water was added and then Et$_2$O (150 mL) and the organic layer was separated. The aqueous layer was reextracted twice with Et$_2$O (50 mL). The combined organic layers were washed with water, brine, dried on sodium sulfate, filtered and evaporated. The residue was purified by flash chromatography (Biotage instrument, SNAP 340 column, EtOAc in Hex from 30% to 60% in 10 CV) affording the title compound as a colourless oil (5.43 g, yield: 74%).

$^1$H NMR (300 MHz, CDCl$_3$) δ 3.91 (s, 3H), 3.89 (s, 3H), 3.83 (d, J=4.7, 3H), 3.77 (d, J=6.6, 3H), 3.60-3.49 (m, 2H), 2.71 (t, J=7.1, 2H), 2.40 (t, J=6.3, 1H), 2.17 (s, 3H), 1.80-1.66 (m, 2H).

Step 6: Synthesis of 3-(2,3,4,5-tetramethoxy-6-methylphenyl)propyl methanesulfonate To a stirred solution of 1-(3-hydroxypropyl)-2,3,4,5-tetramethoxy-6-methylbenzene (5.4 g, 20 mmol) and Et3N (2.8 mL, 20.4 mmol, 1.02 eq) and DMAP (0.2 g) in dry CH$_2$Cl$_2$ (50 mL) was added at 0° C. dropwise methanesulfonyl chloride (2.31 g, 20.2 mmol, 1.01 eq) and the reaction was stirred for 5 h at this temperature and then diluted with water. The organic layer was separated and washed successively with water, 0.1 M aqueous HCl, water $^1$H NMR (300 MHz, CDCl$_3$) δ 4.27 (t, J=6.4, 1H), 3.91 (s, 1H), 3.89 (s, 1H), 3.83 (d, J=4.8, 2H), 3.78 (s, 2H), 3.02 (s, 1H), 2.75-2.65 (m, 1H), 2.17 (s, 2H), 1.98-1.87 (m, 1H).

Step 7: Synthesis of 3-(2,3,4,5-tetramethoxy-6-methylphenyl)propyl nitrate

A stirred solution of 3-(2,3,4,5-tetramethoxy-6-methylphenyl) propyl methanesulfonate (1.31 g, 3.77 mmol), tetrabutylammonium nitrate (0.23 g, 0.75 mmol, 0.2 eq) and sodium nitrate (0.43 g, 5.07 mmol, 1.5 eq) in a 3/1 mixture of butyl acetate and acetonitrile (10 mL) was heated at 90° C. for 16 h and then cooled down to rt. The reaction was diluted with water and the organic layer was separated, washed with water and then dried on sodium sulfate, filtered and evaporated. The residue was purified by flash chromatography (Biotage SP4 instrument, SNAP 100 column, EtOAc in nHex from 20% to 30% in 10 CV) affording the title compound as a colourless oil (0.73 g, Yield: 45%).

$^1$H NMR (300 MHz, CDCl$_3$) δ 4.47 (t, J=6.5, 2H), 3.91 (s, 3H), 3.89 (s, 3H), 3.82 (s, 3H), 3.78 (s, 3H), 2.76-2.63 (m, 2H), 2.16 (d, J=1.9, 3H), 1.98-1.82 (m, 2H).

Step 8: Synthesis of 3-(4,5-dimethoxy-2-methyl-3,6-dioxo cyclohexa-1,4-dienyl)propyl nitrate (Compound (8))

To a solution of 3-(2,3,4,5-tetramethoxy-6-methylphenyl) propyl nitrate (0.294 g, 0.929 mmol) in acetonitrile/water 1:1 (10 mL) cooled to 0° C. was added CAN (1.16 g, 2.05 mmol, 2 eq). After 3 h, the reaction was diluted with H$_2$O/EtOAc and the organic layer was separated, washed with water, brine, dried on sodium sulfate, filtered and evaporated. The residue was purified by flash chromatography (Biotage SP4 instrument, SNAP 100 column, EtOAc in nHex from 20% to 30% in 10 CV) affording the title compound as an orange oil (0.198 g, Yield: 74%).

$^1$H NMR (300 MHz, CDCl$_3$) δ 4.47 (t, J=6.3, 2H), 4.03-3.94 (m, 6H), 2.65-2.53 (m, 2H), 2.03 (s, 3H), 1.94-1.79 (m, 2H).

EXAMPLE 17

Synthesis of 6-(4,5-dimethoxy-2-methyl-3,6-dioxo-cyclohexa-1,4-dienyl)hexyl nitrate (Compound (16))

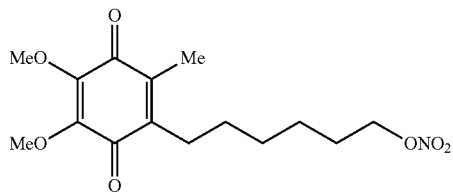

(16)

To a solution of 2,3-dimethoxy-5-methyl-p-benzoquinone (1.04 g, 5.72 mmol), 7-(nitrooxy)heptanoic acid (1.10 g, 5.72 mmol) and AgNO$_3$ (0.97 g, 5.72 mmol) in CH$_3$CN (50 ml) heated at 75° C., a solution of K$_2$S$_2$O$_8$ (1.55 g, 5.72 mmol) in H$_2$O (50 ml) was added dropwise. The reaction mixture was stirred at 75° C. for 3 hours, then it was allowed to cool to room temperature, and was poured in H$_2$O (50 ml). The product was extracted with EtOAc (2×30 ml). The combined organic layers were washed with NaHCO$_3$ sat. solution and brine, dried on Na$_2$SO$_4$ and concentrated. The residue was purified by flash chromatography (Biotage SP1 instrument, SNAP 50 g column, EtOAc in Hex from 5% to 50% in 10 CV) affording 125 mg (Yield: 7%) of the title compound ad a red oil.

$^1$H NMR (300 MHz, CDCl$_3$) δ 4.50-4.38 (m, 2H), 3.96 (s, 6H), 2.54-2.36 (m, 2H), 2.01 (s, 3H), 1.83-1.64 (m, 2H), 1.52-1.31 (m, 6H).

EXAMPLE 18

Synthesis of 4-(4,5-dimethoxy-2-methyl-3,6-dioxo-cyclohexa-1,4-dienyl)butyl nitrate (Compound (4))

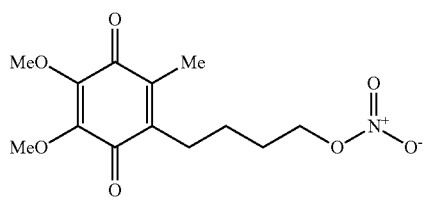

(4)

To a solution of 2,3-dimethoxy-5-methyl-p-benzoquinone (0.54 g, 2.95 mmol), 5-(nitrooxy)pentanoic acid (0.48 g, 2.95 mmol) and AgNO$_3$ (0.50 g, 2.95 mmol) in CH$_3$CN (15 ml) heated at 75° C., a solution of K$_2$S$_2$O$_8$ (0.96 g, 3.54 mmol) in H$_2$O (15 ml) was added dropwise. The reaction mixture was stirred at 75° C. for 3 hours, then it was allowed to cool to room temperature, and was poured in H$_2$O (10 ml). The product was extracted with EtOAc (2×10 ml). The combined organic layers were washed with NaHCO$_3$ sat. solution and brine, dried on Na$_2$SO$_4$ and concentrated. The residue was purified by flash chromatography (Biotage SP1 instrument, SNAP 50 g column, EtOAc in Hex from 5% to 40% in 15 CV) affording 90 mg of a red oil (Yield: 10%).

$^1$H NMR (300 MHz, CDCl$_3$) δ 4.47 (t, 2H), 3.99 (s, 6H), 2.61-2.42 (m, 2H), 2.03 (s, 3H), 1.86-1.69 (m, 2H), 1.60-1.41 (m, 2H).

EXAMPLE 19

Synthesis of 11-(4,5-dimethoxy-2-methyl-3,6-dioxo-cyclohexa-1,4-dienyl)undecane-1,2-diyl dinitrate (Compound (17))

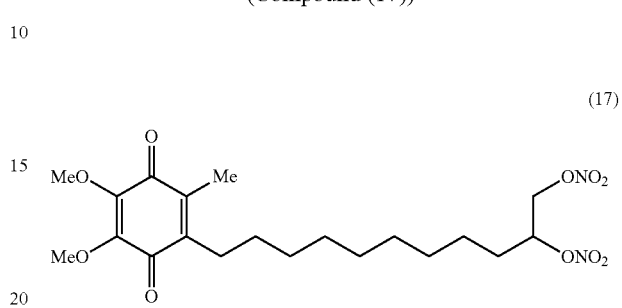

(17)

Step 1: Synthesis of 10-(4,5-dimethoxy-2-methyl-3,6-dioxocyclohexa-1,4-dienyl)decanal To a solution of oxalyl chloride (1.0 mL, 11.82 mmol, 2 eq) in dry dichloromethane (40 mL) cooled to −78° C. was added over a period of 5 min DMSO (1.68 mL, 23.64 mmol, 4 eq). After 10 min of stirring at this temperature, a solution of idebenone (2.0 g, 5.91 mmol) in CH$_2$Cl$_2$ (20 mL) was added over a period of 5 min. After another 5 min of stirring, Et$_3$N (6.6 mL, 47.28 mmol, 8 eq) and the reaction stirred for 1 h and then left to warm to rt. Water was added and the organic layer was extracted, washed successively with 0.1 M aqueous HCl, water and brine, dried on sodium sulfate, filtered and evaporated. The residue was purified by flash chromatography (Biotage SP4, SNAP 100 column, EtOAc in Hex from 20% to 40% in 10 CV) to afford the title compound as a yellow solid (1.68 g Yield: 84%).

$^1$H NMR (300 MHz, CDCl$_3$) δ 9.76 (d, J=1.6, 1H), 3.99 (s, 6H), 2.42 (dt, J=9.0, 4.4, 4H), 2.01 (s, 3H), 1.68-1.58 (m, 2H), 1.35-1.21 (m, 18H).

Step 2: Synthesis of 2,3-dimethoxy-5-methyl-6-(undec-10-enyl)cyclohexa-2,5-diene-1,4-dione To a stirred solution of methyltriphenylphosphonium bromide (860 mg, 2.4 mmol, 1.2 eq.) in dry THF was added at 0° C. a 1M solution of lithio bis(trimethylsilyl)amide in THF (2.5 mL, 2.6 mmol, 1.3 eq.). After 30 min of stirring, 10-(4,5-dimethoxy-2-methyl-3,6-dioxocyclohexa-1,4-dienyl)decanal (672 mg, 2.0 mmol) was added. The solution became green and then brown. Water was then added to quench the reaction and acidified to pH 4 with HCl M. The reaction was extracted with Et2O (3*20 mL). The combined organic layers were washed with water and brine, dried (sodium sulfate), filtered and evaporated. The residue was purified by flash chromatography (Biotage SP4, SNAP 100 column, EtOAc in Hex from 15% to 40% in 10 CV) to afford the title compound as a yellow oil (132 mg Yield: 10%).

Step 3: Synthesis of 11-(4,5-dimethoxy-2-methyl-3,6-dioxocyclohexa-1,4-dienyl)undecane-1,2-diyldinitrate (Compound (17))

To a stirred solution of 2,3-dimethoxy-5-methyl-6-(undec-10-enyl)cyclohexa-2,5-diene-1,4-dione (130 mg, 0.39 mmol)

and silver nitrate (660 mg, 0.39 mmol, 1 eq) in acetonitrile cooled to −15° C. was added iodine (100 mg, 0.39 mmol, 1 eq). The reaction was stirred for 30 min at this temperature then silver nitrate (660 mg, 0.39 mmol, 1 eq) was added and the reaction was heated at 40° C. for 8 h. The reaction was cooled down and brine was added. After 30 min of stirring, EtOAc was added and the precipitate filtered off. The organic layer was separated and washed with water and brine, dried on sodium sulfate, filtered and evaporated. The residue was purified by flash chromatography (Biotage SP4, SNAP 100 column, EtOAc in Hex from 15% to 40% in 10 CV) to afford the title compound as a reddish oil (71 mg Yield: 40%).

$^1$H NMR (300 MHz, CDCl$_3$) δ 5.27 (ddt, J=10.0, 6.7, 3.3, 1H), 4.74 (dt, J=12.8, 2.9, 1H), 4.47 (ddd, J=12.8, 6.7, 4.2, 1H), 3.99 (s, 6H), 2.45 (t, J=7.2, 2H), 2.01 (s, 3H), 1.81-1.61 (m, 2H), 1.50-1.19 (m, 14H).

EXAMPLE 20

Synthesis of 11-(4,5-dimethoxy-2-methyl-3,6-dioxo-cyclohexa-1,4-dienyl)undecan-2-yl nitrate (Compound (18))

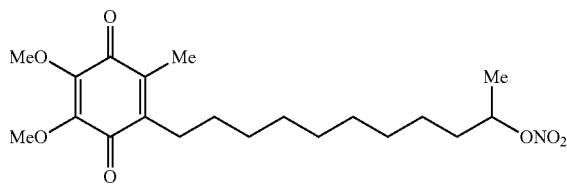

(18)

Step 1: Synthesis of 2-(10-hydroxydecyl)-5,6-dimethoxy-3-methylbenzene-1,4-diol

Step 2: Synthesis of tert-butyl 2-(10-hydroxydecyl)-5,6-dimethoxy-3-methyl-1,4-phenylene dicarbonate To a stirred solution of 2-(10-hydroxydecyl)-5,6-dimethoxy-3-methylbenzene-1,4-diol (1 g, 2.94 mmol) and Et$_3$N (0.9 mL, 6.47 mmol, 2.2 eq) in dry THF (40 mL) was added at 0° C. a solution of Boc$_2$O (1.34 g, 6.17 mmol, 2.1 eq) in dry THF (5 mL). The reaction was stirred overnight at rt and then diluted with H$_2$O/EtOAc. The organic layer was separated and washed with HCl 0.1M, water, saturated aqueous NaHCO$_3$, water and brine, dried on sodium sulfate, filtered and evaporated. The residue was purified by flash chromatography (Biotage SP4, SNAP 100 column, EtOAc in Hex from 20% to 40% in 10 CV) to afford the title compound as a colorless oil (1.26 g, Yield: 79%).

Step 3: Synthesis of tert-butyl 2,3-dimethoxy-5-methyl-6-(10-oxodecyl)-1,4-phenylene dicarbonate To a stirred solution of Synthesis of tert-butyl 2-(10-hydroxydecyl)-5,6-dimethoxy-3-methyl-1,4-phenylene dicarbonate (900 mg, 1.66 mmol) in dry CH$_2$Cl$_2$ cooled to 0° C. was added PCC (0.54 g, 2.5 mmol, 1.5 eq) and the reaction was stirred for 6 h at this temperature. The solid were then filtered off and washed with CH2Cl2. The organic layer was washed with water, HCl 1M, water and brine, dried on sodium sulphate, filtered and evaporated. The residue was purified by flash chromatography (Biotage SP4, SNAP 50 column, EtOAc in Hex from 15% to 30% in 10 CV) to afford the title compound as a colourless oil (640 mg, Yield: 71%).

Step 4: Synthesis of tert-butyl 2-(10-hydroxyundecyl)-5,6-dimethoxy-3-methyl-1,4-phenylene dicarbonate To a stirred solution of tert-butyl 2,3-dimethoxy-5-methyl-6-(10-oxodecyl)-1,4-phenylene dicarbonate 430 mg, 0.835 mmol) in dry THF (10 mL) cooled to −78° C. was added slowly a 3M solution of methylmagnesium iodide in Et$_2$O (0.4 mL, 1.2 mmol, 1.2 eq) and the reaction was stirred for 1 h at this temperature then left to turn back to rt. The reaction was quenched by addition of water and then 1M aqueous HCl to dissolve magnesium salts. EtOAc was added and the organic layer extracted, washed with water and brine, dried on sodium sulfate, filtered and evaporated. The residue was purified by flash chromatography (Biotage SP1 instrument, SNAP 50 g column, EtOAc in Hex from 10% to 30% in 10 CV) to afford the title compound as a colourless oil (364 mg, Yield: 79%).

Step 5: Synthesis of tert-butyl 2,3-dimethoxy-5-methyl-6-(10-(nitrooxy)undecyl)-1,4-phenylene dicarbonate To a stirred solution of tert-butyl 2-(10-hydroxyundecyl)-5,6-dimethoxy-3-methyl-1,4-phenylene dicarbonate (310 mg, 0.561 mmol), tetrabutylammonium nitrate (180 mg, 5.89 mmol, 1.05 eq) and 2,6-di-tert-butyl-4-methylpyridine (126 mg, 0.617 mmol, 1.1 eq) in dry CH$_2$Cl$_2$ cooled to −78° C. was added dropwise trific anhydride (0.1 mL, 5.89 mmol, 1.1 eq) and the reaction was stirred for 1 h at −78° C. and left to turn back to rt. The reaction was then quenched with water and the organic layer was separated, washed with water and brine, dried on sodium sulfate, filtered and evaporated. The residue was purified by flash chromatography (Biotage SP4, SNAP 100 column, EtOAc in Hex from 20% to 30% in 10 CV) affording the title compound as a yellowish oil (126 mg, Yield: 21%).

Step 6: Synthesis of 11-(4,5-dimethoxy-2-methyl-3,6-dioxo cyclohexa-1,4-dienyl)undecan-2-yl nitrate (Compound (18))

A solution of tert-butyl 2,3-dimethoxy-5-methyl-6-(10-(nitrooxy)undecyl)-1,4-phenylene dicarbonate (250 mg, 0.416 mmol) in EtOAc (10 mL) was treated with a 4M solution of HCl in dioxane (0.41 mL, 1.66 mmol, 3 eq) and was stirred overnight at rt. The reaction was evaporated to dryness and then diluted with Et$_2$O and Ag$_2$O (192 mg, 0.832 mmol, 2 eq) was added and the reaction stirred for 2 h. The silver salts were filtered off and the residue was purified twice by flash chromatography (Biotage SP4, SNAP 100 column, EtOAc in Hex from 20% to 40% in 10 CV) affording the title compound as a red oil (94 mg, Yield: 52%).

$^1$H NMR (300 MHz, CDCl$_3$) δ 5.06 (dd, J=12.6, 6.3, 1H), 3.99 (s, 6H), 2.45 (t, J=7.2, 2H), 2.01 (s, 3H), 1.76-1.46 (m, 6H), 1.45-1.20 (m, 18H).

EXAMPLE 21

Synthesis of 3-(4,5-dimethoxy-2-methyl-3,6-dioxo-cyclohexa-1,4-dienyl)propane-1,2-diyl dinitrate (Compound (9))

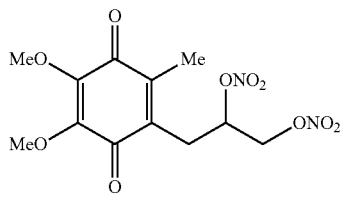

(9)

Step 1: Synthesis of 2-allyl-5,6-dimethoxy-3-methyl-1,4-phenylene tert-butyl dicarbonate To a stirred solution of 2-allyl-5,6-dimethoxy-3-methyl-benzo-1,4-quinone (1.2 g, 5.4 mmol) in EtOH (20 mL) was added portionwise sodium borohydride (0.51 g, 13.5 mmol, 2.5 eq) and the reaction was stirred for 30 min. The reaction was cooled to 0° C. and quenched carefully by the addition of water. EtOAc was added and the organic layer separated, washed with water, brine, filtered and evaporated. The residue was then diluted in dry THF (20 mL) and Et$_3$N (2.26 mL, 16.2 mmol, 3 eq) followed by a solution of Boc$_2$O (3.5 g, 16.2 mmol, 3 eq) in THF were added. The reaction was stirred overnight at rt and then washed with water, HCl 1M, water and brine. The organic layer was dried on sodium sulfate, filtered and evaporated. The residue was purified by flash chromatography (Biotage SP4, SNAP 100 column, EtOAc in n-Hex from 10% to 20% in 10 CV) affording the title compound as a colourless oil (1.27 g, Yield: 55%).

Step 2: Synthesis of 2-(2,3-bis(nitrooxy)propyl)-5,6-dimethoxy-3-methyl-1,4-phenylene tert-butyl dicarbonate To a stirred solution of 2-allyl-5,6-dimethoxy-3-methyl-1,4-phenylene tert-butyl dicarbonate (500 mg, 1.18 mmol) and silver nitrate (200 mg, 1.18 mmol, 1 eq) in acetonitrile (15 mL) cooled to −15° C. was added iodine (300 mg, 1.18 mmol, 1 eq) and the reaction was stirred at this temperature for 30 min then left to rt for 30 min. Silver nitrate (200 mg, 1.18 mmol, 1 eq) was added and the reaction stirred for 16 h at rt. Brine was added and the reaction stirred for 30 min. The salts formed were filtered off, washed with EtOAc and the resulting solution diluted with water (30 mL) and EtOAc (30 mL). The organic layer was separated and washed with brine, filtered and evaporated. The residue was purified by flash chromatography (Biotage SP4, SNAP 100 column, EtOAc in n-Hex from 10% to 30% in 10 CV) affording the title compound as red oil (361 mg, Yield: 56%).

Step 3: Synthesis of 3-(4,5-dimethoxy-2-methyl-3,6-dioxo cyclohexa-1,4-dienyl)propane-1,2-diyl dinitrate (Compound (9)

A solution of 2-(2,3-bis(nitrooxy)propyl)-5,6-dimethoxy-3-methyl-1,4-phenylene tert-butyl dicarbonate (360 mg, 6.56 mmol) in Et$_2$O was treated with a 4 M solution of HCl in dioxane (0.5 mL) overnight. The reaction was then concentrated to dryness and directly purified by flash chromatography (Biotage SP4, SNAP 100 column, EtOAc in n-Hex from 20% to 40% in 10 CV) affording the title compound as a red oil (31 mg, Yield: 13%).

Mass spectrum (EI), m/z 348.25 (M+H)$^+$ (C$_{12}$H$_{14}$N$_2$O$_{10}$ requires 347.24)

EXAMPLE 22

Synthesis of 3-(3-(4,5-dimethoxy-2-methyl-3,6-dioxocyclohexa-1,4-dienyl)propoxy)propyl nitrate (Compound (14))

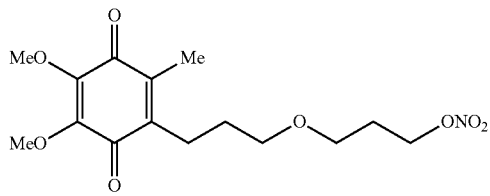

(14)

Step 1: Synthesis of 1-[3-(allyloxy)propyl]-2,3,4,5-tetra methoxy-6-methylbenzene To a stirred solution of allyl alcohol (0.10 g, 1.72 mmol, 1.2 eq) in dry THF was added sodium hydride (0.046 g, 90% in mineral oil, 1.4 eq) and after 10 min, 3-(2,3,4,5-tetramethoxy-6-methylphenyl)propyl methanesulfonate (0.5 g, 1.43 mmol) was added and a catalytic amount of 15-crown-S. The reaction heated at 70° C. overnight and then evaporated to dryness. The residue was purified by flash chromatography (Biotage SP4 instrument, column SNAP 100, EtOAc in Hex from 15% to 30% in 8 CV) affording the title compound as a colourless oil (0.415 g, Yield: 93%).

$^1$H NMR (300 MHz, CDCl$_3$) δ 5.94 (ddd, J=22.6, 10.7, 5.5, 1H), 5.29 (dd, J=17.2, 1.2, 1H), 5.17 (dd, J=10.4, 1.2, 1H), 4.00 (d, J=5.5, 2H), 3.90 (s, 6H), 3.82 (s, 3H), 3.78 (s, 3H), 3.49 (t, J=6.5, 2H), 2.65 (dd, J=9.0, 6.5, 2H), 2.17 (s, 3H), 1.82-1.69 (m, 2H).

Step 2: Synthesis of 2-[3-(2,3,4,5-tetramethoxy-6-methylphenyl)propoxy]propanol To a stirred solution of 1-[3-(allyloxy)propyl]-2,3,4,5-tetramethoxy-6-methylbenzene (0.415 g, 1.34 mmol) in dry THF was added at 0° C. a 0.5M solution of 9-BBN in THF (2.9 mL, 1.2 eq) and the reaction was stirred at rt for 18 h. The reaction was cooled to 0° C. and simultaneously were added a 3M aqueous solution of NaOH (2.2 mL) and a 30% aqueous solution of H2O2 (2.2 mL). After 30 min, the organic layer was diluted with Et2O (30 mL) and water (50 mL) and the organic layer was separated. The aqueous layer was extracted twice with Et2O (30 mL). The combined organic layers were washed with H2O, brine, dried on sodium sulfate, filtered and evaporated. The residue was purified by flash chromatography (Biotage SP4, column SNAP 100, EtOAc in Hex from 20% to 50% in 10 CV) affording the title compound as a colourless oil (0.165 g, Yield: 37%).

$^1$H NMR (300 MHz, CDCl$_3$) δ 3.89 (s, 3H), 3.86 (s, 3H), 3.81 (m, 5H), 3.78 (s, 3H), 3.64 (t, J=5.7, 2H), 3.48 (t, J=6.4, 2H), 2.68-2.58 (m, 2H), 2.16 (s, 3H), 1.91-1.80 (m, 2H), 1.80-1.64 (m, 3H).

Step 3: Synthesis of 2-[3-(2,3,4,5-tetramethoxy-6-methylphenyl)propoxy]ethyl nitrate To a solution of 2-[3-(2,3,4,5-tetramethoxy-6-methylphenyl) propoxy]propanol (162 mg, 0.493 mmol), tetrabutylammonium nitrate (158 mg, 0.518 mmol, 1.1 eq) and 2,6-di-tert-butyl-4-methylpyridine (106 mg, 0.518 mmol, 1.1 eq) in dry dichloromethane (5 mL) cooled to −78° C. was slowly added trifle anhydride (87 μL, 0.518 mmol, 1.1 eq). The reaction was stirred at −78° C. for 30 min and then left to go back to rt. The reaction was then quenched using water. The organic layer was separated and washed with water and brine, dried on sodium sulfate, filtered and evaporated. The residue was purified by flash chromatography (Biotage SP4, column SNAP 50, EtOAc in Hex from 20% to 40% in 10 CV) affording the title compound as a colorless oil (0.05472 g, Yield: 29%) along with compound 14 as a reddish oil (0.036 g, Yield: 21%).

$^1$H NMR (300 MHz, CDCl$_3$) δ 4.68-4.58 (m, 2H), 3.91 (s, 3H), 3.90 (s, 3H), 3.82 (s, 3H), 3.78 (s, 3H), 3.76-3.69 (m, 2H), 3.51 (t, J=6.4, 2H), 2.64 (dd, J=8.9, 6.7, 2H), 2.17 (s, 3H), 1.81-1.68 (m, 2H).

Step 4: Synthesis of 3-(3-(4,5-dimethoxy-2-methyl-3,6-dioxocyclohexa-1,4-dienyl)propoxy)propyl nitrate (Compound (14))

To a solution of 2-[3-(2,3,4,5-tetramethoxy-6-methylphenyl) propoxy]ethyl nitrate (54 mg, 0.144 mmol) in a 1/1 mixture of water and acetonitrile (2 mL) was added at 0° C. cerium ammonium nitrate (CAN, 0.171 g, 0.303 mmol, 2.1 eq). The reaction was stirred for 3 h then diluted with water and EtOAc. The organic layer was separated, washed with water and brine, dried on sodium sulfate, filtered and evaporated. The residue was purified by flash chromatography (Biotage SP4, SNAP 25 g column, nHex/EtOAc 8/2 to 7/3, 8 CV) affording the title compound as a red oil (37 mg, Yield: 74%).

$^1$H NMR (300 MHz, CDCl$_3$) δ 4.57 (t, J=6.4, 2H), 3.99 (s, 3H), 3.99 (s, 3H), 3.49 (t, J=6.0, 2H), 3.42 (t, J=6.2, 2H), 2.58-2.49 (m, 2H), 2.02 (s, 3H), 1.97 (dd, J=12.3, 6.2, 2H), 1.74-1.61 (m, 2H).

EXAMPLE 23

Synthesis of 2-(3-(4,5-dimethoxy-2-methyl-3,6-dioxocyclohexa-1,4-dienyl)propoxy)ethyl nitrate (Compound (20))

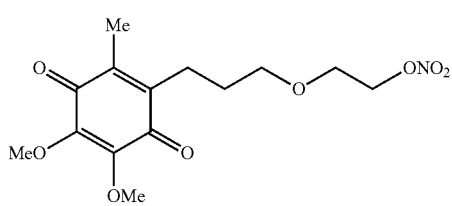

(20)

Step 1: Synthesis of ((2-(3-(2,3,4,5-tetramethoxy-6-methylphenyl)propoxy)ethoxy)methanetriyl)tribenzene To a stirred solution of 3-(2,3,4,5-tetramethoxy-6-methylphenyl)propan-1-ol (0.54 g, 2.0 mmol) in dry DMF was added at 0° C. sodium hydride (90% in mineral oil, 0.057 g, 2.4 mmol, 1.2 eq) and a catalytic amount of 15-crown-5. The reaction was stirred for 15 min and then [(2-iodoethoxy)(diphenyl)methyl]benzene (0.83 g, 2.0 mmol, 1 eq) was added and the reaction heated at 80° C. overnight. Water and Et2O (20 mL of each) were then added at rt and the organic layer separated. The aqueous layer was extracted once with Et2O and the combined organic layers were washed with water and brine, dried on sodium sulfate, filtered and evaporated. The residue was purified by flash chromatography (Biotage SP4, column SNAP 100, EtOAc in Hex from 10% to 30% in 10 CV) affording the title compound as an oil (0.25 g, Yield: 22%).

$^1$H NMR (300 MHz, CDCl$_3$) δ 7.56-7.43 (m, 6H), 7.34-7.16 (m, 12H), 3.91 (s, 3H), 3.89 (s, 2H), 3.81 (s, 3H), 3.78 (s, 3H), 3.64 (t, J=5.1, 2H), 3.55 (t, J=6.4, 2H), 3.25 (t, J=5.1, 2H), 2.69 (dd, J=9.1, 6.7, 2H), 2.19 (s, 3H), 1.84-1.70 (m, 2H).

Step 2: Synthesis of 2-[3-(2,3,4,5-tetramethoxy-6-methylphenyl)propoxy]ethanol

A solution of ((2-(3-(2,3,4,5-tetramethoxy-6-methylphenyl) propoxy)ethoxy)methanetriyl)tribenzene (0.25 g, 0.449 mmol) and pyridinium paratoluenesulfonate (56 mg, 0.224 mmol, 0.5 eq) in a 1/1 mixture of CHCl$_3$/MeOH was stirred overnight. The reaction was then evaporated to dryness and purified by flash chromatography (Biotage SP4, column SNAP 50, EtOAc in Hex from 20% to 40% in 10 CV) affording the title compound as an oil (0.121 g, Yield: 86%).

$^1$H NMR (300 MHz, CDCl$_3$) δ 3.91 (s, 3H), 3.90 (s, 3H), 3.82 (s, 3H), 3.79 (s, 3H), 3.74 (dd, J=8.6, 4.5, 2H), 3.58-3.54 (m, 2H), 3.51 (t, J=6.4, 2H), 2.67 (dd, J=8.5, 6.9, 2H), 2.21 (t, J=4.5, 1H), 2.17 (s, 3H), 1.83-1.71 (m, 2H).

Step 3: 2-(3-(2,3,4,5-tetramethoxy-6-methylphenyl)propoxy)ethyl nitrate

To a solution of 2-[3-(2,3,4,5-tetramethoxy-6-methylphenyl) propoxy]ethanol (0.121 g, 0.385 mmol), tetrabutylammonium nitrate (134 mg, 0.435 mmol, 1.1 eq) and 2,6-di-tert-butyl-4-methylpyridine (106 mg, 0.518 mmol, 1.1 eq) in dry dichloromethane (5 mL) coiled to −78° C. was slowly added trifle anhydride (87 μL, 0.518 mmol, 1.1 eq). The reaction was stirred at −78° C. for 30 min and then left to go back to rt. The reaction was then quenched using water. The organic layer was separated and washed with water and brine, dried on sodium sulfate, filtered and evaporated. The residue was purified by flash chromatography (Biotage SP4, column SNAP 50, EtOAc in Hex from 20% to 40% in 10 CV) affording the title compound as a colorless oil (0.072 g, Yield: 37%) along with compound 14 as a reddish oil (0.036 g, Yield: 21%).

$^1$H NMR (300 MHz, CDCl$_3$) δ 4.67-4.59 (m, 2H), 3.91 (s, 3H), 3.90 (s, 3H), 3.82 (s, 3H), 3.78 (s, 3H), 3.76-3.68 (m, 2H), 3.51 (t, J=6.4, 2H), 2.64 (dd, J=8.9, 6.7, 2H), 1.81-1.68 (m, 2H).

Step 4: 2-(3-(4,5-dimethoxy-2-methyl-3,6-dioxocyclohexa-1,4-dienyl)propoxy)ethyl nitrate (Compound (20))

To a solution of 2-[3-(2,3,4,5-tetramethoxy-6-methylphenyl) propoxy]ethyl nitrate (72 mg, 0.144 mmol) in a 1/1 mixture of water and acetonitrile (2 mL) was added at 0° C. cerium ammonium nitrate (CAN, 237 mg, 0.42 mmol, 2.1 eq). The reaction was stirred for 3 h then diluted with water and EtOAc. The organic layer was separated, washed with water and brine, dried on sodium sulfate, filtered and evaporated. The residue was purified by flash chromatography (Biotage SP4, SNAP 25 g column, nHex/EtOAc 8/2 to 7/3, 8 CV) affording the title compound as a red oil (52 mg, Yield: 79%).

$^1$H NMR (300 MHz, CDCl$_3$) δ 4.64-4.55 (m, 2H), 3.99 (s, 6H), 3.72-3.64 (m, 2H), 3.48 (t, J=6.1, 2H), 2.55 (t, J=7.6, 2H), 2.03 (s, 3H), 1.76-1.63 (m, 2H).

EXAMPLE 24

Synthesis of 6-(3-(4,5-dimethoxy-2-methyl-3,6-dioxocyclohexa-1,4-dienyl)propylthio)hexyl nitrate (Compound (21))

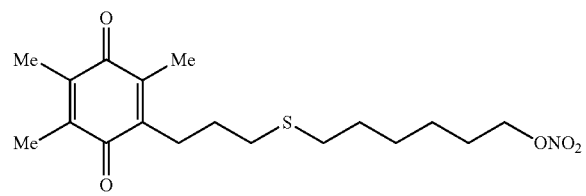

(21)

Step 1: Synthesis of S-[3-(2,3,4,5-tetramethoxy-6-methylphenyl) propyl]ethanethioate To a solution of 3-(2,3,4,5-tetramethoxy-6-methylphenyl) propyl methanesulfonate (synthesized as in example 7, steps 1-6) (3.0 g; 8.6 mmol) in DMF (30 ml), Potassium thioacetate (2.0 g; 17.2 mmol) and NaI (0.26 g: 1.7 mmol) were added. The mixture was stirred 3 hours at room temperature then H$_2$O (30 ml) and EtOAc (30 ml) were added. The two phases were separated and the organic layer was extracted with EtOAc (2×20 ml). The combined organic layers were washed with H$_2$O (5×20 ml), brine (20 ml), dried on Na$_2$SO$_4$ and concentrated under reduced pressure affording 2.8 g (Yield: 100%) of the title compound as a clear oil $^1$H NMR (300 MHz, CDCl$_3$) δ 3.93-3.86 (m, 6H), 3.81 (s, 3H), 3.77 (s, 3H), 3.00-2.88 (m, 2H), 2.69-2.58 (m, 2H), 2.32 (s, 3H), 2.15 (s, 3H), 1.82-1.66 (m, 2H).

Step 2: Synthesis of 3-(2,3,4,5-tetramethoxy-6-methylphenyl) propane-1-thiol

To a solution of S-[3-(2,3,4,5-tetramethoxy-6-methylphenyl)propyl]ethanethioate (0.10 g; 0.30 mmol) in MeOH (2 ml), 3 drops of Sodium methoxide solution 25 wt. % in MeOH were added. The solution was stirred 15 minutes at room temperature then was quenched with Amberlite® IR-120H ion-exchange resin. The resin was filtered off and the solvent evaporated affording 80 mg (Yield: 92%) of the title compound.

$^1$H NMR (300 MHz, CDCl$_3$) δ 3.96-3.87 (m, 6H), 3.82 (s, 3H), 3.78 (s, 3H), 2.73-2.64 (m, 2H), 2.64-2.52 (m, 2H), 2.17 (s, 3H), 1.84-1.70 (m, 2H).

Step 3: Synthesis of 6-(3-(2,3,4,5-tetramethoxy-6-methylphenyl) propylthio)hexan-1-ol To a solution of 3-(2,3,4,5-tetramethoxy-6-methylphenyl) propane-1-thiol (0.59 g; 2.06 mmol) and 6-Bromo-1-hexanol (0.32 µl; 2.47 mmol) in DMF (10 ml) cooled at 0° C., Cs$_2$CO$_3$ (0.80 g; 2.47 mmol) was added. The mixture was stirred 2 hours at room temperature then H$_2$O (10 ml) and EtOAc (10 ml) were added. The two phases were separated end the aqueous one was extracted with EtOAc (2×10 ml). The combined organic layers were washed with H$_2$O (5×10 ml), brine, dried on Na$_2$SO$_4$ and concentrated under reduced pressure. The residue was purified by flash chromatography (Biotage SP1 instrument, SNAP 50 g column, EtOAc in Hex from 9% to 60% in 10 CV) affording 590 mg (Yield: 74%) of the title compound as a clear oil.

$^1$H NMR (300 MHz, CDCl$_3$) δ 3.96-3.86 (m, 6H), 3.82 (s, 3H), 3.78 (s, 3H), 3.71-3.58 (m, 3H), 2.73-2.62 (m, 2H), 2.62-2.47 (m, 4H), 2.17 (s, 3H), 1.66-1.48 (m, 4H), 1.51-1.27 (m, 4H).

Step 4: Synthesis of 6-(3-(2,3,4,5-tetramethoxy-6-methylphenyl) propylthio)hexyl nitrate To a solution of 6-(3-(2,3,4,5-tetramethoxy-6-methylphenyl) propylthio)hexan-1-ol (0.59 g; 1.53 mmol), Et$_4$NNO$_3$ (0.35 g; 1.83 mmol) and 2,6-Di-tert-butyl-4-methylpyridine (0.38 g; 1.83 mmol) in dry CH$_2$Cl$_2$ (25 ml) under N$_2$ atmosphere and cooled at −78° C., a solution of Trifluoromethansulfonic anhydride (0.30 ml; 1.83 mmol) in CH$_2$Cl$_2$ (5 ml) was added dropwise. The mixture was stirred at −78° C. 3 hours then a saturated solution of NH$_4$Cl (10 ml) was added and the mixture was allowed to reach room temperature. The two phases were separated and the aqueous one was extracted with CH$_2$Cl$_2$ (20 ml). The combined organic phases were washed with brine, dried on Na$_2$SO$_4$ and concentrated under reduced pressure. The residue was purified by flash chromatography (Biotage SP1 instrument, SNAP 25 g column, Hex/EtOAc 94:6, 10 CV) affording 108 mg (Yield: 16%) of the title compound as a clear oil.

$^1$H NMR (300 MHz, CDCl$_3$) δ 4.45 (t, 2H), 3.95-3.86 (m, 6H), 3.82 (s, 3H), 3.78 (s, 3H), 2.75-2.62 (m, 2H), 2.62-2.48 (m, 4H), 2.17 (s, 3H), 1.82-1.67 (m, 4H), 1.49-1.37 (m, 4H).

Step 5: Synthesis of 6-(3-(4,5-dimethoxy-2-methyl-3,6-dioxocyclohexa-1,4-dienyl)propylthio)hexyl nitrate To a solution of 6-(3-(2,3,4,5-tetramethoxy-6-methylphenyl) propylthio)hexyl nitrate (0.18 g; 0.41 mmol) in CH$_3$CN: H$_2$O 1:1 (8 ml), cerium ammonium nitrate (0.58 g; 1.02 mmol) was added. The mixture was stirred 3 hours at room temperature then H$_2$O (5 ml) and Et$_2$O (10 ml) were added. The two phases were separated and the aqueous layer was extracted with Et$_2$O (10 ml). The combined organic layers were washed with H$_2$O (10 ml) and brine, dried on Na$_2$SO$_4$ and concentrated under reduced pressure. The residue was purified by flash chromatography (Biotage SP1 instrument, SNAP 25 g column, EtOAc in Hex from 5% to 50% in 10 CV) affording 90 mg (Yield: 55%) of the title compound as an orange oil.

$^1$H NMR (300 MHz, CDCl$_3$) δ 4.45 (t, 2H), 4.05-3.94 (m, 6H), 2.63-2.44 (m, 6H), 2.04 (s, 3H), 1.81-1.51 (m, 6H), 1.51-1.35 (m, 4H).

EXAMPLE 25

Synthesis of 10-(3-methyl-1,4-dioxo-1,4-dihydronaphthalen-2-yl)decyl nitrate (Compound (13))

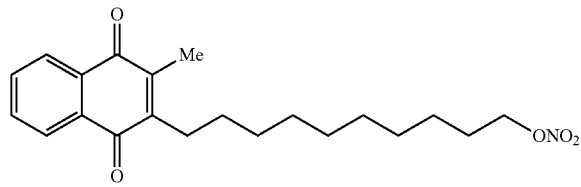

(13)

Step 1: Synthesis of 11-(nitrooxy)undecanoic acid

To a solution of 11-Bromoundecanoic acid (1.50 g; 5.65 mmol) in CH$_3$CN (20 ml), AgNO$_3$ (1.15 g; 6.78 mmol) was added. The solution was heated at the mw 22 minutes at 120° C. The salts were filtered off and the solvent evaporated. EtOAc was added and the salts were filtered off again, the solvent was evaporated affording 1.3 g (yield: 100%) of the title compound as a clear oil.

$^1$H NMR (300 MHz, CDCl$_3$) δ 4.50-4.36 (m, 2H), 2.35 (t, 2H), 1.81-1.54 (m, 4H), 1.48-1.21 (m, 12H).

Step 2: Synthesis of 10-(3-methyl-1,4-dioxo-1,4-dihydro naphthalen-2-yl)decyl nitrate To a solution of 2-methyl-1,4-naphthoquinone (0.97 g, 5.65 mmol), 11-(nitrooxy)undecanoic acid (1.3 g, 5.65 mmol) and AgNO$_3$ (0.96 mg, 5.65 mmol) in CH$_3$CN (50 ml) heated at 75° C., a solution of K$_2$S$_2$O$_8$ (1.83 g, 6.77 mmol) in H$_2$O (50 ml) was added dropwise. The reaction mixture was stirred at 75° C. for 5 hours, was then allowed to cool to room temperature, and was poured in H$_2$O (50 ml). The product was extracted with EtOAc (2×30 ml). The combined organic layers were washed with NaHCO$_3$ saturated solution and brine, dried over Na$_2$SO$_4$ and concentrated. The residue was purified by flash chromatography (Biotage SP1 instrument, SNAP 100 g column, Hex:EtOAc 95:5, 10 CV) affording 419 mg (Yield: 20%) of the title compound as a yellow oil.

Mass spectrum (EI), m/z 374.18 (M+H)$^+$ (C$_{21}$H$_{27}$NO$_5$ requires 373.45)

EXAMPLE 26

Synthesis of 4-(3-methyl-1,4-dioxo-1,4-dihydronaphthalen-2-yl)butyl nitrate (Compound (22))

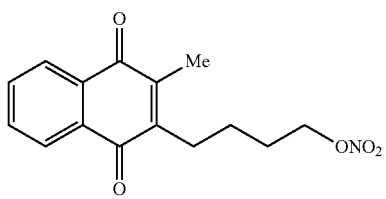

(22)

To a solution of 2-methyl-1,4-naphthoquinone (0.63 g, 3.68 mmol), 5-(nitrooxy)pentanoic acid (synthesized as in Example 4, steps 2 and 3) (0.60 g, 3.68 mmol) and AgNO$_3$ (0.62 g, 3.68 mmol) in CH$_3$CN (20 ml) heated at 75° C., a solution of K$_2$S$_2$O$_8$ (1.20 g, 4.41 mmol) in H$_2$O (20 ml) was added dropwise. The reaction mixture was stirred at 75° C. for 3 hours, was then allowed to cool to room temperature, and was poured in H$_2$O (20 ml). The product was extracted with EtOAc (2×15 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 97:3, 24 CV) affording 260 mg (Yield: 24%) of the title compound as a yellow oil.

$^1$H NMR (300 MHz, CDCl$_3$) δ 8.15-7.99 (m, 2H), 7.77-7.61 (m, 2H), 4.50 (t, 2H), 2.79-2.57 (m, 2H), 2.20 (s, 3H), 1.93-1.74 (m, 2H), 1.74-1.49 (m, 2H).

EXAMPLE 27

Synthesis of 6-(3-methyl-1,4-dioxo-1,4-dihydronaphthalen-2-yl) hexyl nitrate (Compound (23))

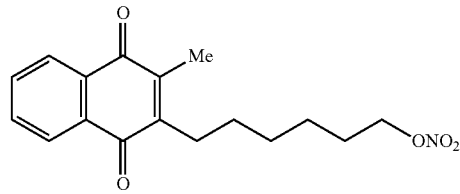

(23)

To a solution of 2-methyl-1,4-naphthoquinone (0.98 g, 5.72 mmol), 7-(nitrooxy)heptanoic acid (synthesized as in Example 3, steps 2 and 3) (1.1 g, 5.72 mmol) and AgNO$_3$ (0.97 g, 5.72 mmol) in CH$_3$CN (25 ml) heated at 75° C., a solution of K$_2$S$_2$O$_8$ (1.55 g, 5.72 mmol) in H$_2$O (25 ml) was added dropwise. The reaction mixture was stirred at 75° C. for 3 hours, was then allowed to cool to room temperature, and was poured in H$_2$O (25 ml). The product was extracted with EtOAc (2×20 ml). The combined organic layers were washed with NaHCO$_3$ saturated solution and brine, dried over Na$_2$SO$_4$ and concentrated. The residue was purified by flash chromatography (Biotage SP1 instrument, SNAP 100 g column, Hex:EtOAc 97:3, 15 CV) affording 990 mg (Yield: 54%) of the title compound as a yellow oil.

$^1$H NMR (300 MHz, CDCl$_3$) δ 8.16-7.98 (m, 2H), 7.78-7.58 (m, 2H), 4.45 (t, 2H), 2.73-2.55 (m, 2H), 2.22 (s, 3H), 1.86-1.62 (m, 2H), 1.57-1.38 (m, 4H).

EXAMPLE 28

Synthesis of 3-(3-methyl-1,4-dioxo-1,4-dihydronaphthalen-2-yl)propyl nitrate (Compound (24))

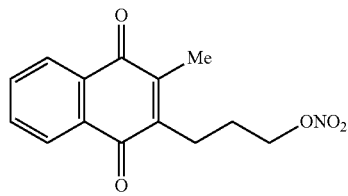

(24)

Step 1: Synthesis of Compound A

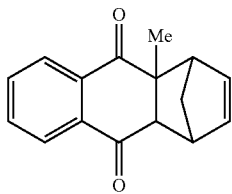

To a stirred solution of menadione (6.89 g, 40 mmol) in acetic acid was added freshly distilled cyclopentadiene (5 mL, 60 mmol, 1.5 eq) and the reaction was stirred for 2 days. The reaction was then poured in water/ice and extracted with EtOAc (2×200 mL). The combined organic layers were washed twice with saturated aqueous $NaHCO_3$ solution, water and brine, dried on sodium sulfate, filtered and evaporated to give the title compound as a pale yellow solid (7.76 g, Yield: 78%).

$^1$H NMR (300 MHz, $CDCl_3$) δ 8.07-7.96 (m, 2H), 7.72-7.63 (m, 2H), 6.09 (dd, J=5.6, 2.9, 1H), 5.90 (dd, J=5.6, 2.8, 1H), 3.51 (d, J=18.4, 1H), 3.21 (s, 1H), 3.05 (d, J=3.8, 1H), 1.80-1.71 (m, 1H), 1.60-1.51 (m, 3H).

Step 2: Synthesis of Compound B

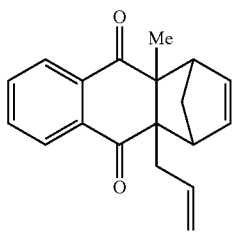

To a stirred solution of crude A (Step 1) (5.4 g) in dry THF (100 mL) cooled to 0° C. was added portionwise potassium tert-butoxide (4.0 g, 32.9 mmol, 1.5 eq). The reaction became dark reddish and was stirred at this temperature for another 30 mins then a solution of allyl bromide (2.9 mL, 35.1 mmol, 1.6 eq) in dry THF (30 mL) was added slowly. The reaction was stirred for 2 h before addition of water (30 mL). The aqueous layer was acidified to pH 2 and the solution was extracted with Et2O (3×50 mL). The combined organic layers were washed with water and brine, dried on sodium sulfate, filtered and evaporated. The residue was purified by flash chromatography (Biotage instrument, SNAP 340 column, EtOAc in Hex from 20% to 40% in 10 CV) affording the title compound as a pale yellow oil (4.22 g, yield: 67%).

$^1$H NMR (300 MHz, $CDCl_3$) δ 7.97-7.85 (m, 2H), 7.73-7.62 (m, 2H), 6.08-6.03 (m, 2H), 5.67 (ddt, J=17.1, 10.1, 7.0, 1H), 5.35 (ddd, J=13.8, 11.8, 1.5, 1H), 5.00 (dd, J=23.0, 5.9, 2H), 3.25 (d, J=1.6, 1H), 3.19-3.11 (m, 1H), 2.82 (dd, J=14.5, 7.2, 1H), 2.58 (dd, J=14.5, 6.9, 1H), 1.88 (t, J=8.4, 1H), 1.59-1.54 (m, 3H).

Step 3: Synthesis of 2-allyl-3-methylnaphthoquinone

A solution of B (Step 2) (0.67 g, 2.4 mmol) in toluene was heated at 120° C. for 5 h. The solvents were evaporated under reduced pressure and the residue crystallized from hexane/$Et_2O$ to give the title compound as a pale yellow solid (480 mg, Yield: 94%).

$^1$H NMR (300 MHz, $CDCl_3$) δ 8.17-8.02 (m, 2H), 7.75-7.64 (m, 2H), 5.84 (ddt, J=16.4, 10.1, 6.3, 1H), 5.08 (ddt, J=13.7, 12.5, 6.3, 2H), 3.42 (d, J=6.2, 2H), 2.16 (s, 3H).

Step 4: Synthesis of 2-allyl-1,4-dimethoxy-3-methylnaphthalene

To a stirred solution of 2-allyl-3-methylnaphthoquinone (8.0 g, 37.7 mmol) and tetrabutylammonium chloride (0.5 g) in THF/water (1/1, 500 mL each) was added slowly sodium dithionite (65.6 g, 377 mmol, 10 eq). The reaction was stirred for 30 min at this temperature then cooled to 0° C. and soda (22.6 g, 565 mmol, 15 eq) was added portionwise. After 10 min, methyl iodide (46 mL, 754 mmol, 20 eq) was added and the reaction was heated at 40° C. overnight. The reaction was then diluted with water (200 mL) and extracted with $Et_2O$ (3×300 mL). The combined organic layers were washed with water and brine, dried on sodium sulfate, filtered and evaporated. The residue was purified by flash chromatography (Biotage SP4, 2×SNAP 340 g columns, nHex:EtOAc 95/5 to 85/15 in 10 CV) affording the title compound as a pale yellow solid (7.5 g, Yield: 82%).

$^1$H NMR (300 MHz, $CDCl_3$) δ 8.12-8.00 (m, 2H), 7.57-7.40 (m, 2H), 6.15-5.91 (m, 1H), 5.05 (dd, J=10.2, 1.7, 1H), 4.91 (dd, J=17.2, 1.8, 1H), 3.90 (s, 3H), 3.87 (s, 3H), 3.64 (dt, J=5.4, 1.7, 2H), 2.39 (s, 3H).

Step 5: Synthesis of 3-(1,4-dimethoxy-3-methyl-2-naphthyl)propan-1-ol

To a solution of 2-allyl-1,4-dimethoxy-3-methylnaphthalene (7.5 g, 30.95 mmol) in dry THF (300 mL) cooled to 0° C. was added dropwise a 0.5 M solution of 9-BBN in THF (124 mL, 62 mmol, 2 eq) and the reaction was stirred overnight at rt. The reaction was cooled to 0° C. and simultaneously were added a 3M aqueous solution of NaOH (81 mL) and a 30% aqueous solution of $H_2O_2$ (81 mL). After 60 min of stirring, the organic layer was diluted with $Et_2O$ (300 mL) and water (500 mL) and the organic layer was separated. The aqueous layer was extracted twice with $Et_2O$ (300 mL). The combined organic layers were washed with water, brine, dried on sodium sulfate, filtered and evaporated. The residue was purified by flash chromatography (Biotage SP4, column SNAP 340, EtOAc in Hex from 20% to 50% in 10 CV) affording the title compound as a colourless oil (5.62 g, Yield: 70%).

$^1$H NMR (300 MHz, $CDCl_3$) δ 8.14-8.01 (m, 1H), 7.77-7.65 (m, 1H), 4.53 (td, J=6.3, 2.8, 1H), 2.84-2.70 (m, 1H), 2.19 (d, J=13.2, 2H), 1.94 (tt, J=17.6, 8.8, 1H).

Step 6: Synthesis of 3-(1,4-dimethoxy-3-methyl-2-naphthyl)propyl methanesulfonate To a solution of 3-(1,4-dimethoxy-3-methyl-2-naphthyl) propan-1-ol (5.6 g, 21.51 mmol), $Et_3N$ (3.6 mL, 25.8 mmol, 1.2 eq) and DMAP (0.2 g) in dry $CH_2Cl_2$ (70 mL) cooled to 0° C. was added dropwise a solution of mesyl chloride (5.04 g, 23.6 mmol, 1.1 eq) in $CH_2Cl_2$ (20 mL). The reaction was stirred for 6 h at rt and then diluted with water (100 mL). The organic layer was separated and washed with water, HCl 0.1 M, water and brine, dried on sodium sulfate, filtered and evaporated. The residue was purified by flash chromatography (Biotage SP4, column SNAP 340, EtOAc in Hex from 20% to 50% in 10 CV) affording the title compound as a colourless oil (5.62 g, Yield: 70%).

$^1$H NMR (300 MHz, CDCl$_3$) δ 8.11-7.93 (m, 2H), 7.54-7.39 (m, 2H), 4.31 (t, J=6.3, 2H), 3.90 (s, 3H), 3.87 (s, 3H), 3.02 (s, 3H), 2.97-2.89 (m, 2H), 2.39 (s, 3H), 2.11-1.96 (m, 2H).

Step 7: Synthesis of
3-(1,4-dimethoxy-3-methyl-2-naphthyl)propyl nitrate

A solution of 3-(1,4-dimethoxy-3-methyl-2-naphthyl)propyl methanesulfonate (650 mg, 1.92 mmol), tetrabutylammonium nitrate (117 mg, 0.38 mmol, 0.2 eq) and sodium nitrate (151 mg, 2.3 mmol, 1.2 eq) in a 1/1 mixture of butyl acetate and acetonitrile (10 mL) was heated overnight at 90° C. The reaction was then cooled down then diluted with water. The organic layer was separated and washed with water and brine, dried on sodium sulfate, filtered and evaporated. The residue was purified by flash chromatography (Biotage SP4, SNAP 100 g column, nHex/EtOAc 80/20 to 40/60 in 10 CV) affording the title compound as a clear oil (500 mg, Yield: 89%).

$^1$H NMR (300 MHz, CDCl$_3$) δ 8.08-7.97 (m, 2H), 7.53-7.41 (m, 2H), 4.53 (td, J=6.5, 2.7, 2H), 3.90 (s, 3H), 3.87 (s, 3H), 2.99-2.86 (m, 2H), 2.41 (s, 3H), 2.06-1.93 (m, 2H).

Step 8: Synthesis of 3-(3-methyl-1,4-dioxo-1,4-dihydro naphthalen-2-yl)propyl nitrate (Compound 21)

To a solution of 3-(1,4-dimethoxy-3-methyl-2-naphthyl) propyl nitrate (500 mg, 1.63 mmol) in a 1/1 mixture of water and acetonitrile (10 mL) was added at 0° C. cerium ammonium nitrate (CAN, 1.94 g, 3.43 mmol, 2.1 eq). The reaction was stirred for 3 h then diluted with water and EtOAc. The organic layer was separated, washed with water and brine, dried on sodium sulfate, filtered and evaporated. The residue was purified by flash chromatography (Biotage SP4, SNAP 100 g column, nHex/EtOAc 8/2 to 7/3, 8 CV) affording the title compound as a red oil (231 mg, Yield: 89%).

$^1$H NMR (300 MHz, CDCl$_3$) δ 8.15-8.01 (m, 2H), 7.80-7.61 (m, 2H), 4.53 (td, J=6.3, 2.8, 2H), 2.86-2.65 (m, 2H), 2.29-2.11 (m, 3H), 2.08-1.84 (m, 2H).

EXAMPLE 29

Synthesis of 3-(3-(3-methyl-1,4-dioxo-1,4-dihydronaphthalen-2-yl)propoxy)propyl nitrate (Compound (25))

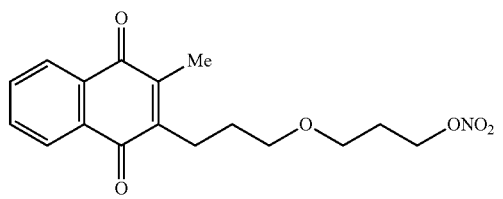

Step 1: Synthesis of 2-[3-(allyloxy)propyl]-1,4-dimethoxy-3-methylnaphthalene

A solution of 3-(1,4-dimethoxy-3-methyl-2-naphthyl)propan-1-ol (Example 21, Step 5) (900 mg, 3.46 mmol) in DMF cooled to 0° C. was added portionwise sodium hydride (90% in mineral oil, 110 mg, 4.15 mmol, 1.2 eq). After 15 min, allyl bromide (0.36 mL, 4.15 mmol, 1.2 eq) and 15-crown-5 (0.1 mL) were added and the reaction heated at 90° C. overnight. The reaction was quenched with water and EtOAc was added. The organic layer was separated and washed with water and then brine. The residue was purified by flash chromatography (Biotage SP4, SNAP 100 g column, nHex/EtOAc 85/15 to 7/3, 8 CV) affording the title compound as a colorless oil (750 mg, Yield: 72%).

$^1$H NMR (300 MHz, CDCl$_3$) δ 8.12-7.95 (m, 2H), 7.52-7.39 (m, 2H), 6.06-5.86 (m, 1H), 5.31 (ddd, J=17.2, 3.3, 1.6, 1H), 5.19 (dd, J=10.4, 1.5, 1H), 4.02 (dt, J=5.5, 1.4, 2H), 3.91 (s, 3H), 3.87 (s, 3H), 3.55 (t, J=6.4, 2H), 2.99-2.81 (m, 2H), 2.43 (s, 3H), 1.88 (tt, J=12.7, 6.4, 2H).

Step 2: Synthesis of 3-[3-(1,4-dimethoxy-3-methyl-2-naphthyl)propoxy]propan-1-ol To a solution of 2-[3-(allyloxy)propyl]-1,4-dimethoxy-3-methylnaphthalene (1.5 g, 4.99 mmol) in dry THF (40 mL) was added dropwise a 0.5M solution of 9-BBN (26 mL, 13 mmol, 2.2 eq) and the reaction was stirred overnight at rt, then cooled to 0° C. A 3M aqueous solution of sodium hydroxide (8.2 mL, 25 mmol, 5 eq) and a 30% aqueous solution of H2O2 (8.2 mL, 5 eq) were added. The reaction was stirred for 30 min then diluted with water and Et$_2$O. The organic layer was separated and the aqueous layer extracted 3 times with Et$_2$O (10 mL). The combined organic layers were washed with water and brine, dried on sodium sulfate, filtered and evaporated. The residue was purified by flash chromatography (Biotage SP4, SNAP 100 g column, nHex/EtOAc 7/3 to 5/5 in 8 CV) affording the title compound as a white solid (510 mg, Yield: 32%).

$^1$H NMR (300 MHz, CDCl$_3$) δ 8.09-7.97 (m, 2H), 7.50-7.40 (m, 2H), 3.90 (s, 3H), 3.87 (s, 3H), 3.82 (dd, J=10.9, 5.4, 2H), 3.66 (t, J=5.7, 2H), 3.53 (t, J=6.3, 2H), 2.93-2.84 (m, 2H), 2.55 (t, J=5.5, 1H), 2.42 (s, 3H), 1.92-1.80 (m, 4H).

Step 3: Synthesis of 3-[3-(1,4-dimethoxy-3-methyl-2-naphthyl)propoxy]propyl nitrate To a solution of 3-[3-(1,4-dimethoxy-3-methyl-2-naphthyl) propoxy]propan-1-ol (0.51 g, 1.60 mmol), Bu$_4$NNO$_3$ (0.586 g, 1.92 mmol, 1.2 eq) and 2,6-Di-tert-butyl-4-methylpyridine (0.362 g, 1.76 mmol) in dry CH$_2$Cl$_2$ (20 ml) under N$_2$ atmosphere and cooled at −78° C., a solution of trifluoromethansulfonic anhydride (0.29 ml, 1.76 mmol) in CH$_2$Cl$_2$ (5 ml) was added dropwise. The mixture was stirred at −78° C. for 1 hour then a saturated solution of NH$_4$Cl (10 ml) was added and the mixture was allowed to reach room temperature. The two phases were separated and the aqueous one was extracted with CH$_2$Cl$_2$ (20 ml). The combined organic phases were washed with brine, dried on Na$_2$SO$_4$ and concentrated under reduced pressure. The residue was purified by flash chromatography (Biotage SP4, SNAP 100 column, Hex/EtOAc 80/20 to 60/40 in 10 CV) affording the title compound as a clear oil (354 mg, Yield: 60%).

$^1$H NMR (300 MHz, CDCl$_3$) δ 8.11-7.97 (m, 2H), 7.51-7.39 (m, 2H), 4.60 (td, J=6.5, 3.0, 2H), 3.89 (d, J=4.9, 3H), 3.87 (s, 3H), 3.58-3.45 (m, 4H), 2.88 (dd, J=8.9, 6.8, 2H), 2.42 (s, 3H), 2.06-1.96 (m, 3H), 1.91-1.75 (m, 2H).

Step 4: Synthesis of 3-(3-(3-methyl-1,4-dioxo-1,4-dihydronaphthalen-2-yl)propoxy)propyl nitrate (Compound 25)

To a stirred solution 3-[3-(1,4-dimethoxy-3-methyl-2-naphthyl)propoxy]propyl nitrate (354 mg, 0.971 mmol) in a 1:1 mixture of water and acetonitrile (10 mL) cooled to 0° C. was added cerium ammonium nitrate (1.15 g, 2.04 mmol, 2.1 eq). The reaction was stirred for 3 h at 0° C. then diluted with water and EtOAc. The organic layer was separated, washed with water and brine, dried on sodium sulfate, filtered and evaporated. The residue was purified by flash chromatography (Biotage SP4, SNAP 100 column, Hex/EtOAc 80/20 to 60/40 in 10 CV) affording the title compound as a yellow oil (275 mg, Yield: 85%).

$^1$H NMR (300 MHz, CDCl$_3$) δ 8.08 (dt, 1=6.0, 3.1, 2H), 7.74-7.64 (m, 2H), 4.54 (td, J=6.4, 3.0, 2H), 3.49 (dd, J=10.5, 6.0, 4H), 2.79-2.65 (m, 2H), 2.21 (s, 3H), 1.94 (p, J=6.2, 2H), 1.85-1.68 (m, 2H).

EXAMPLE 30

Synthesis of 3-(3-methyl-1,4-dioxo-1,4-dihydronaphthalen-2-yl)propane-1,2-diyl dinitrate (Compound (27))

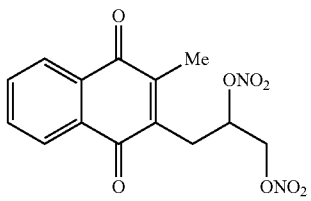

(27)

Step 1: Synthesis of 3-(1,4-dimethoxy-3-methyl-2-naphthyl)propane-1,2-diol

To a stirred solution of 2-allyl-1,4-dimethoxy-3-methylnaphthalene (2.42 g, 10 mmol) was added to a solution of ADmix (7 g of ADmix α and 7 g of ADmix β) in a 1/1 mixture of water and tBuOH (50 mL each). The reaction was stirred at RT for 16 h and the reaction was diluted with water/EtOAc (20 mL each). Sodium dithionite (3.6 g) was added slowly and after 30 min of stirring, the organic layer was extracted, washed with water, brine, filtered and evaporated. The residue was crystallized overnight in Et$_2$O to give the title compound as a white solid (2.03 g, 73%).

$^1$H NMR (300 MHz, CDCl$_3$) δ 8.11-7.97 (m, 1H), 7.54-7.45 (m, 1H), 3.97-3.91 (m, 2H), 3.88 (d, J=7.8, 2H), 3.70-3.56 (m, 1H), 3.56-3.43 (m, 1H), 3.06 (d, J=7.0, 1H), 2.77 (d, J=5.7, OH), 2.62 (dd, J=11.8, 6.5, OH), 2.44 (s, 2H).

Step 2: Synthesis of 3-(3-methyl-1,4-dioxo-1,4-dihydro naphthalen-2-yl)propane-1,2-diyl dinitrate (Compound (27))

To a solution of 3-(1,4-dimethoxy-3-methyl-2-naphthyl) propane-1,2-diol (0.59 g, 1.53 mmol), Bu$_4$NNO$_3$ (0.73 g, 1.83 mmol, 2.4 eq) and 2,6-Di-tert-butyl-4-methylpyridine (0.38 g, 1.83 mmol) in dry CH$_2$Cl$_2$ (25 ml) under N$_2$ atmosphere and cooled at −78° C., a solution of trifluoromethansulfonic anhydride (0.30 ml; 1.83 mmol) in CH$_2$Cl$_2$ (5 ml) was added dropwise. The mixture was stirred at −78° C. 3 hours then a saturated solution of NH$_4$Cl (10 ml) was added and the mixture was allowed to reach room temperature. The two phases were separated and the aqueous one was extracted with CH$_2$Cl$_2$ (20 ml). The combined organic phases were washed with brine, dried on Na$_2$SO$_4$ and concentrated under reduced pressure. The residue was purified by flash chromatography (Biotage SP4, SNAP 100 column, Hex/EtOAc 80/20 to 60/40 in 10 CV) affording the title compound as a red oil (51 mg, Yield: 15%).

Mass spectrum (EI), m/z 360.18 (M-Na)$^+$ (C$_{14}$H$_{12}$N$_2$O$_8$ requires 337.25).

EXAMPLE 31

Synthesis of 6-(5-methoxy-2,4-dimethyl-3,6-dioxocyclohexa-1,4-dienyl)hexyl nitrate (Compound (28))

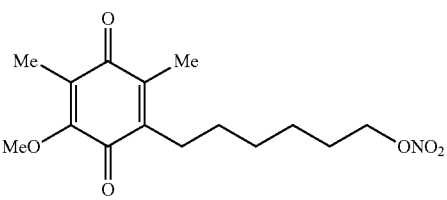

(28)

Step 1: Synthesis of 3,5-dimethyl-2-methoxy-p-benzoquinone

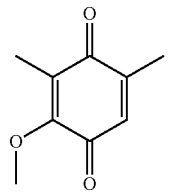

The title compound was synthesized as described in literature (*Bioorganic & Medicinal Chemistry* 18 (2010) 6429-6441), starting from 2,6-dimethyl-p-benzoquinone which was treated with acetic anhydride and boron trifluoride-etherate 14 at 40° C. affording 1,2,4-triacetoxy-3,5-dimethylbenzene in 92% yield. 1,2,4-triacetoxy-3,5-dimethylbenzene was then treated with sodium hydroxide and dimethyl sulfate in methanol at 23° C. to provide 3,5-dimethyl-1,2,4-trimethoxybenzene in 82% yield. Finally, 3,5-dimethyl-1,2,4-trimethoxybenzene was oxidized using phenyliodine diacetate (PIDA) to obtain 3,5-dimethyl-2-methoxy-p-benzoquinone in 65% yield.

Step 2: Synthesis of 6-(5-methoxy-2,4-dimethyl-3,6-dioxo cyclohexa-1,4-dienyl)hexyl nitrate (Compound (28))

To a solution of 3,5-dimethyl-2-methoxy-p-benzoquinone (0.52 g, 3.12 mmol), 7-(nitrooxy)heptanoic acid (synthesized as in Example 3, steps 2 and 3) (0.6 g, 3.12 mmol) and AgNO$_3$ (0.53 g, 3.12 mmol) in CH$_3$CN (55 ml) heated at 75° C., a solution of K$_2$S$_2$O$_8$ (1.00 g, 3.74 mmol) in H$_2$O (55 ml) was added dropwise. The reaction mixture was stirred at 75° C. for 3 hours, was then allowed to cool to room temperature, and was poured in H$_2$O (55 ml). The product was extracted with EtOAc (2×35 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 95:5, 10 CV) affording 150 mg (Yield: 15%) of the title compound as a yellow oil.

$^1$H NMR (300 MHz, CDCl$_3$) δ 4.52-4.57 (m, 2H), 3.95 (s, 3H), 2.56-2.57 (m, 2H), 2.00 (s, 3H), 1.94 (s, 3H), 1.81-1.62 (m, 2H), 1.52-1.32 (m, 6H).

EXAMPLE 32

Synthesis of 6-(4-methoxy-2,5-dimethyl-3,6-dioxo-cyclohexa-1,4-dienyl)hexyl nitrate (Compound (29))

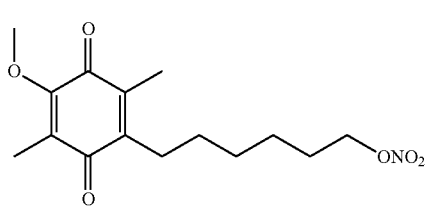

(29)

Step 1: Synthesis of 3,6-dimethyl-2-methoxy-p-benzoquinone

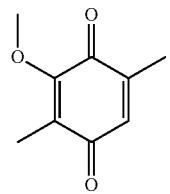

The title compound was synthesized as described in literature (*Bioorganic & Medicinal Chemistry* 18 (2010) 6429-6441), starting from 2,5-dimethyl-p-benzoquinone which was treated with acetic anhydride and boron trifluoride-etherate at 40° C. affording 1,2,4-triacetoxy-3,6-dimethylbenzene in 92% yield. 1,2,4-triacetoxy-3,6-dimethylbenzene was then treated with sodium hydroxide and dimethyl sulfate in methanol at 23° C. to provide 3,6-dimethyl-1,2,4-trimethoxybenzene in 82% yield. Finally, 3,6-dimethyl-1,2,4-trimethoxybenzene was oxidized using phenyliodine diacetate (PIDA) to obtain 3,6-dimethyl-2-methoxy-p-benzoquinone in 65% yield.

Step 2: Synthesis of 6-(4-methoxy-2,5-dimethyl-3,6-dioxo cyclohexa-1,4-dienyl)hexyl nitrate To a solution of 3,6-dimethyl-2-methoxy-p-benzoquinone (0.52 g, 3.12 mmol), 7-(nitrooxy)heptanoic acid (synthesized as in Example 3, steps 2 and 3) (0.6 g, 3.12 mmol) and AgNO$_3$ (0.53 g, 3.12 mmol) in CH$_3$CN (55 ml) heated at 75° C., a solution of K$_2$S$_2$O$_8$ (1.00 g, 3.74 mmol) in H$_2$O (55 ml) was added dropwise. The reaction mixture was stirred at 75° C. for 3 hours, was then allowed to cool to room temperature, and was poured in H$_2$O (55 ml). The product was extracted with EtOAc (2×35 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 95:5, 10 CV) affording 140 mg (Yield: 14%) of the title compound as a yellow oil.

$^1$H NMR (300 MHz, CDCl$_3$) δ 4.52-4.57 (m, 2H), 3.95 (s, 3H), 2.56-2.57 (m, 2H), 2.00 (s, 3H), 1.94 (s, 3H), 1.81-1.62 (m, 2H), 1.52-1.32 (m, 6H).

EXAMPLE 33

Synthesis of 10-(4-methoxy-2,5-dimethyl-3,6-dioxo-cyclohexa-1,4-dienyl)decyl nitrate (Compound (30))

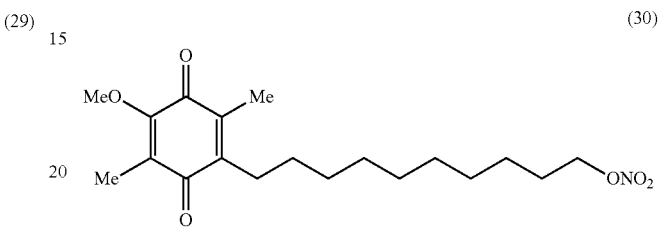

(30)

To a solution of 3,6-dimethyl-2-methoxy-p-benzoquinone (0.52 g, 3.12 mmol), 11-(nitrooxy)undecanoic acid (synthesized as in Example 18, step 1) (0.48 g, 2.89 mmol) and AgNO$_3$ (0.49 g, 2.89 mmol) in CH$_3$CN (15 ml) heated at 75° C., a solution of K$_2$S$_2$O$_8$ (0.94 g, 3.47 mmol) in H$_2$O (15 ml) was added dropwise. The reaction mixture was stirred at 75° C. for 3 hours, was then allowed to cool to room temperature, and was poured in H$_2$O (15 ml). The product was extracted with EtOAc (2×20 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 97:3, 10 CV) affording 350 mg (Yield: 33%) of the title compound as a yellow oil.

$^1$H NMR (300 MHz, CDCl$_3$) δ 4.51-4.37 (m, 2H), 3.95 (s, 3H), 2.55-2.36 (m, 2H), 2.03 (s, 3H), 1.94 (s, 3H), 1.80-1.63 (m, 2H), 1.48-1.16 (m, 14H).

EXAMPLE 34

Synthesis of 10-(5-methoxy-2,4-dimethyl-3,6-dioxo-cyclohexa-1,4-dienyl)decyl nitrate (Compound (31))

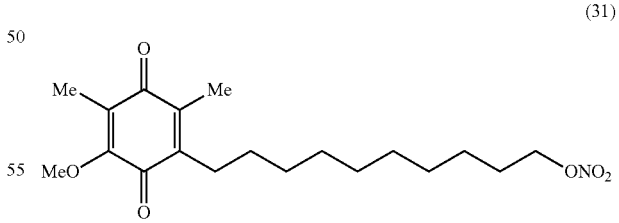

(31)

To a solution of 3,5-dimethyl-2-methoxy-p-benzoquinone (0.67 g, 4.03 mmol), 11-(nitrooxy)undecanoic acid (synthesized as in Example 18, step 1) (1.00 g, 4.03 mmol) and AgNO$_3$ (0.68 g, 4.03 mmol) in CH$_3$CN (25 ml) heated at 75° C., a solution of K$_2$S$_2$O$_8$ (1.31 g, 4.83 mmol) in H$_2$O (25 ml) was added dropwise. The reaction mixture was stirred at 75° C. for 3 hours, was then allowed to cool to room temperature, and was poured in H$_2$O (25 ml). The product was extracted with EtOAc (2×30 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 97:3, 10 CV) affording 460 mg (Yield: 31%) of the title compound as a yellow oil.

$^1$H NMR (300 MHz, CDCl$_3$) δ 4.51-4.37 (m, 2H), 3.95 (s, 3H), 2.55-2.36 (m, 2H), 2.03 (s, 3H), 1.94 (s, 3H), 1.80-1.63 (m, 2H), 1.48-1.16 (m, 14H).

EXAMPLE 35

Synthesis of 8-(4-methoxy-2,5-dimethyl-3,6-dioxo-cyclohexa-1,4-dienyl)octyl nitrate (Compound (32))

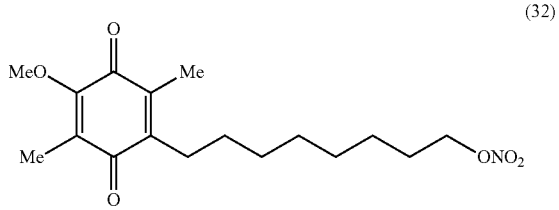

Step 1: Synthesis of 9-bromononanoic acid

To a solution of 9-Bromo-1-nonanol (1.50 g, 6.72 mmol) in acetone (27 ml) cooled at 0° C., a saturated solution of NaHCO$_3$ (9 ml), NaBr (0.14 g, 1.34 mmol) and 2,2,6,6-Tetramethyl-1-piperidinyloxy-free radical (TEMPO) (0.10 g, 0.67 mmol) were added. Then Trichloroisocyanuric acid (3.1 g, 13.44 mmol) was added portionwise. The mixture was stirred 30 minutes at 0° C. and 3 hours at room temperature then was cooled at 0° C. and 2-Propanol (8 ml) was added slowly. The mixture was stirred at 0° C. for further 30 minutes then the white precipitate was filtered off and the mixture concentrated under reduced pressure. H$_2$O (10 ml) and CH$_2$Cl$_2$ (10 ml) were added to the residue. The two phases were separated and the aqueous layer was extracted with CH$_2$Cl$_2$ (2×10 ml). The combined organic layers were dried on Na$_2$SO$_4$ and concentrated affording 1.60 g (Yield: 100%) of the title compound as a white solid.

$^1$H NMR (300 MHz, DMSO) δ 3.49 (t, 2H), 2.23-2.08 (m, 2H), 1.84-1.68 (m, 2H), 1.57-1.14 (m, 10H).

Step 2: Synthesis of 9-(nitrooxy)nonanoic acid

To a solution of 9-bromononanoic acid (1.60 g; 6.72 mmol) in CH$_3$CN (30 ml), AgNO$_3$ (1.53 g; 8.96 mmol) was added. The solution was heated at the mw 22 minutes at 120° C. The salts were filtered off and the solvent evaporated. EtOAc was added and the salts were filtered off again, the solvent was evaporated affording 1.45 g (yield: 98%) of the title compound as a clear oil.

$^1$H NMR (300 MHz, CDCl$_3$) δ 4.50-4.37 (m, 2H), 2.41-2.29 (m, 2H), 1.79-1.54 (m, 4H), 1.44-1.25 (m, 8H).

Step 3: Synthesis of 8-(4-methoxy-2,5-dimethyl-3,6-dioxo cyclohexa-1,4-dienyl)octyl nitrate To a solution of 3,6-dimethyl-2-methoxy-p-benzoquinone (0.54 g, 3.26 mmol), 9-(nitrooxy)nonanoic acid (0.72 g, 3.26 mmol) and AgNO$_3$ (0.55 g, 3.26 mmol) in CH$_3$CN (20 ml) heated at 75° C., a solution of K$_2$S$_2$O$_8$ (1.06 g, 3.91 mmol) in H$_2$O (20 ml) was added dropwise. The reaction mixture was stirred at 75° C. for 3 hours, was then allowed to cool to room temperature, and was poured in H$_2$O (20 ml). The product was extracted with EtOAc (2×25 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 97:3, 15 CV) affording 300 mg (Yield: 25%) of the title compound as a yellow oil.

$^1$H NMR (300 MHz, CDCl$_3$) δ 4.52-4.39 (m, 2H), 4.01 (s, 3H), 2.46 (t, 2H), 2.05 (s, 3H), 1.95 (s, 3H), 1.84-1.65 (m, 2H), 1.49-1.23 (d, 10H).

EXAMPLE 36

Synthesis of 8-(5-methoxy-2,4-dimethyl-3,6-dioxo-cyclohexa-1,4-dienyl)octyl nitrate (Compound (19))

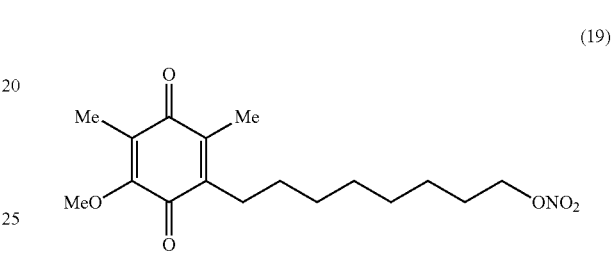

To a solution of 3,5-dimethyl-2-methoxy-p-benzoquinone (0.54 g, 3.26 mmol), 9-(nitrooxy)nonanoic acid (0.72 g, 3.26 mmol) (synthesized as in Example 35, steps 2 and 3) and AgNO$_3$ (0.55 g, 3.26 mmol) in CH$_3$CN (20 ml) heated at 75° C., a solution of K$_2$S$_2$O$_8$ (1.06 g, 3.91 mmol) in H$_2$O (20 ml) was added dropwise. The reaction mixture was stirred at 75° C. for 3 hours, was then allowed to cool to room temperature, and was poured in H$_2$O (20 ml). The product was extracted with EtOAc (2×25 ml). The combined organic layers were washed with NaHCO$_3$ saturated solution and brine, dried over Na$_2$SO$_4$ and concentrated. The residue was purified by flash chromatography (Biotage SP1 instrument, SNAP 50 g column, Hex:EtOAc 97:3, 15 CV) affording 80 mg (Yield: 7%) of the title compound as a yellow oil.

$^1$H NMR (300 MHz, CDCl$_3$) δ 4.52-4.39 (m, 2H), 4.01 (s, 3H), 2.46 (t, 2H), 2.05 (s, 3H), 1.95 (s, 3H), 1.84-1.65 (m, 2H), 1.49-1.23 (d, 10H).

EXAMPLE 37

Synthesis of 10-(2,4,5-trimethyl-3,6-dioxocyclo-hexa-1,4-dienyl)decyl nitrate (Compound (5))

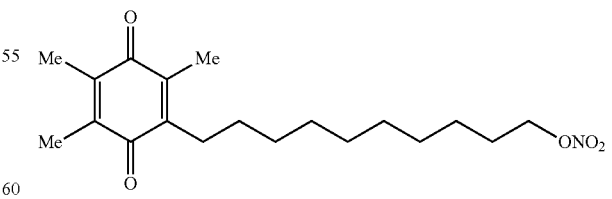

To a solution of 2,3,5-trimethyl-p-benzoquinone (0.95 g, 6.33 mmol), 11-(nitrooxy)undecanoic acid (synthesized as in Example 18, Step 1) (1.39 g, 5.65 mmol) and AgNO$_3$ (0.96 g, 5.65 mmol) in CH$_3$CN (50 ml) heated at 75° C., a solution of K$_2$S$_2$O$_8$ (1.83 g, 6.77 mmol) in H$_2$O (50 ml) was added dropwise. The reaction mixture was stirred at 75° C. for 3 hours, then it was allowed to cool to room temperature, and was poured in H$_2$O (50 ml). The product was extracted with EtOAc (2×30 ml). The combined organic layers were washed with NaHCO$_3$ sat. solution and brine, dried on Na$_2$SO$_4$ and concentrated. The residue was purified by flash chromatography (Biotage SP1 instrument, SNAP 50 g column, Hex/EtOAc 97:3, 15 cv) affording 600 mg (yield: 27%) of the title compound as an orange oil.

Mass spectrum (EI), m/z 352.19 (M+H)$^+$ (C$_{19}$H$_{29}$NO$_5$ requires 351.44)

EXAMPLE 38

Synthesis of 8-(4,5-dimethoxy-2-methyl-3,6-dioxocyclohexa-1,4-dienyl)octyl nitrate (Compound (33))

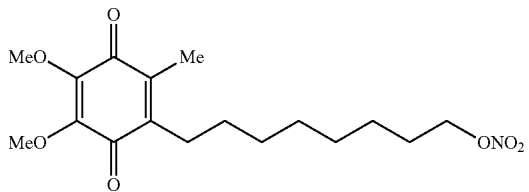

(33)

To a solution of 2,3-dimethoxy-5-methyl-p-benzoquinone (0.774 g, 4.01 mmol), 9-(nitrooxy)nonanoic acid (0.90 g, 4.01 mmol) (synthesized as in Example 28, steps 2 and 3) and AgNO$_3$ (0.68 g, 4.01 mmol) in CH$_3$CN (25 ml) heated at 75° C., a solution of K$_2$S$_2$O$_8$ (1.30 g, 4.81 mmol) in H$_2$O (25 ml) was added dropwise. The reaction mixture was stirred at 75° C. for 3 hours, then it was allowed to cool to room temperature, and was poured in H$_2$O (50 ml). The product was extracted with EtOAc (2×30 ml). The combined organic layers were washed with NaHCO$_3$ sat. solution and brine, dried on Na$_2$SO$_4$ and concentrated. The residue was purified by flash chromatography (Biotage SP1 instrument, SNAP 50 g column, Hex/EtOAc 9:1 in 15 CV) affording 80 mg (Yield: 6%) of the title compound ad a red oil.

$^1$H NMR (300 MHz, CDCl$_3$) δ 4.50-4.36 (m, 2H), 3.99 (s, 6H), 2.53-2.36 (m, 2H), 2.01 (s, 3H), 1.81-1.62 (m, 2H), 1.45-1.26 (m, 10H).

EXAMPLE 39

Synthesis of 8-(2,4,5-trimethyl-3,6-dioxocyclohexa-1,4-dienyl) octyl nitrate (Compound (34))

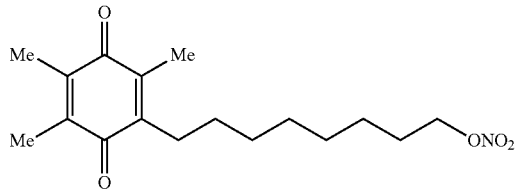

(34)

To a solution of 2,3,5-trimethyl-p-benzoquinone (0.49 g, 3.27 mmol), 9-(nitrooxy)nonanoic acid (0.72 g, 3.27 mmol) (synthesized as in Example 28, steps 2 and 3) and AgNO$_3$ (0.55 g, 3.27 mmol) in CH$_3$CN (20 ml) heated at 75° C., a solution of K$_2$S$_2$O$_8$ (1.06 g, 3.92 mmol) in H$_2$O (20 ml) was added dropwise. The reaction mixture was stirred at 75° C. for 3 hours, then it was allowed to cool to room temperature, and was poured in H$_2$O (50 ml). The product was extracted with EtOAc (2×30 ml). The combined organic layers were washed with NaHCO$_3$ saturated solution and brine, dried on Na$_2$SO$_4$ and concentrated. The residue was purified by flash chromatography (Biotage SP1 instrument, SNAP 50 g column, Hex/EtOAc 97:3, 10 cv) affording 195 mg (yield: 17%) of the title compound as an orange oil.

$^1$H NMR (300 MHz, CDCl$_3$) δ 4.51-4.39 (m, 2H), 2.53-2.41 (m, 2H), 2.02 (s, 9H), 1.80-1.65 (m, 2H), 1.47-1.27 (m, 10H).

EXAMPLE 40

Synthesis of 2-[2-(4,5-dimethoxy-2-methyl-3,6-dioxocyclohexa-1,4-dien-1-yl)ethyl]-4-(nitrooxy)tetrahydrofuran-3-yl nitrate (Compound (35))

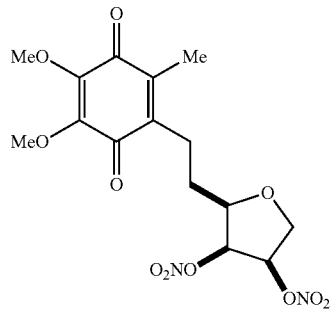

(35)

Step 1: Synthesis of 3-(2,3,4,5-tetramethoxy-6-methylphenyl)propanal

To a stirred solution of 1-(3-Hydroxypropyl)-2,3,4,5-tetramethoxy-6-methylbenzene (4.0 g, 14.8 mmol) in CH$_2$Cl$_2$ (100 mL) cooled to 0° C. was added pyridinium chlorochromate (4.8 g, 22.2 mmol, 1.5 eq) and the reaction was stirred for 6 h at rt. The reaction was filtered on a bed of celite and evaporated to dryness. The residue was purified by flash chromatography (Biotage SP4, SNAP 340 column, nHex/EtOAc from 15% to 30% in 10 CV) to afford the title compound as a colourless oil (3.28 g, Yield: 83%).

$^1$H NMR (300 MHz, CDCl$_3$) δ 9.82 (t, J=1.4, 1H), 3.90 (s, 3H), 3.89 (s, 3H), 3.83 (s, 3H), 3.78 (s, 3H), 2.90 (dd, J=9.9, 5.7, 2H), 2.64-2.55 (m, 2H), 2.16 (s, 3H).

Step 2: Synthesis of 5-(2,3,4,5-tetramethoxy-6-methylphenyl)pent-1-en-3-ol

To a solution of 3-(2,3,4,5-tetramethoxy-6-methylphenyl) propanal (1.00 g, 3.72 mmol) in dry THF (20 mL) cooled to −78° C. was added a 1M solution of vinylmagnesium bromide in THF (5 mL, 5 mmol, 1.3 eq). The reaction was stirred for 1 h at −78° C. and then quenched by addition of water. EtOAc was added and the organic layer was separated, washed with water and brine, dried on sodium sulfate, filtered and evaporated. The residue was purified by flash chromatography (Biotage SP4, SNAP 100 column, nHex/EtOAc 80/20 to 55/45 in 10 CV) to afford the title compound as a colourless oil (0.76 g, Yield: 69%).

$^1$H NMR (300 MHz, CDCl$_3$) δ 5.94 (ddt, J=17.2, 10.6, 5.4, 1H), 5.76 (ddd, J=17.7, 10.3, 7.5, 1H), 5.34-5.13 (m, 4H), 4.12-4.04 (m, 1H), 3.92-3.89 (m, 4H), 3.89 (s, 3H), 3.81 (s, 3H), 3.78 (s, 3H), 2.64 (qdd, J=13.1, 10.8, 5.8, 2H), 2.16 (s, 3H), 1.83-1.59 (m, 2H).

Step 3: Synthesis of 2-[3-(allyloxy)pent-4-enyl]-3,4,5,6-tetramethoxy-1-methylbenzene To a stirred solution of 5-(2,3,4,5-tetramethoxy-6-methylphenyl)pent-1-en-3-ol (0.76 g, 2.57 mmol) in dry THF (10 mL) cooled to −10° C. was added dropwise a 40% solution of NaHMDS in THF (0.565 g, 3.08 mmol, 1.2 eq). The reaction was stirred for 5 min then 15-crown-5 (51 µL, 0.26 mmol, 0.1 eq) and allyl bromide (0.26 g, 3.08 mmol, 1.2 eq). The reaction was stirred at rt overnight and water and EtOAc were added. The organic layer was separated and washed with water and brine, dried on sodium sulfate, filtered and evaporated. The residue was purified by flash chromatography (Biotage SP4, SNAP 100 column, nHex/EtOAc from 15% to 35% in 10 CV) to afford the title compound as a colourless oil (0.65 g, Yield: 75%).

$^1$H NMR (300 MHz, CDCl$_3$) δ 5.94 (ddt, J=17.2, 10.6, 5.4, 1H), 5.76 (ddd, J=17.2, 10.3, 7.5, 1H), 5.34-5.20 (m, 3H), 5.16 (ddd, J=10.4, 3.1, 1.4, 1H), 4.14-4.03 (m, 1H), 3.90 (d, J=2.2, 4H), 3.89 (s, 3H), 3.81 (s, 3H), 3.78 (s, 3H), 2.64 (qdd, J=13.1, 10.8, 5.8, 2H), 2.16 (s, 3H), 1.83-1.59 (m, 2H).

Step 4: Synthesis of 2-[2-(2,3,4,5-tetramethoxy-6-methylphenyl)ethyl]-2,5-dihydrofuran To a degassed solution of 2-[3-(allyloxy)pent-4-enyl]-3,4,5,6-tetramethoxy-1-methylbenzene (0.65 g, 1.93 mmol) in dry CH$_2$Cl$_2$ (6 mL) was added Grubbs catalyst 1$^{st}$ generation (0.153 g, 0.19 mmol, 0.05 eq) and the reaction was refluxed for 2 h. The reaction was cooled to rt and evaporated to dryness. The residue was purified by flash chromatography (Biotage SP4, SNAP 100 column, nHex/EtOAc from 10% to 25% in 8 CV) to afford the title compound as a colourless oil (0.52 g, Yield: 87%).

$^1$H NMR (300 MHz, CDCl$_3$) δ 5.95-5.89 (m, 1H), 5.85 (ddd, J=6.3, 3.7, 2.3, 1H), 4.89 (dd, J=6.7, 3.0, 1H), 4.78-4.59 (m, 2H), 3.90 (s, 3H), 3.89 (s, 3H), 3.82 (s, 3H), 3.78 (s, 3H), 2.66 (qdd, J=13.0, 10.0, 6.3, 2H), 2.17 (s, 3H), 1.79-1.61 (m, 2H).

Step 5: Synthesis of 2-[2-(2,3,4,5-tetramethoxy-6-methylphenyl)ethyl]tetrahydrofuran-3,4-diol

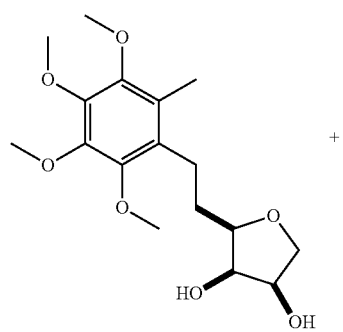

+

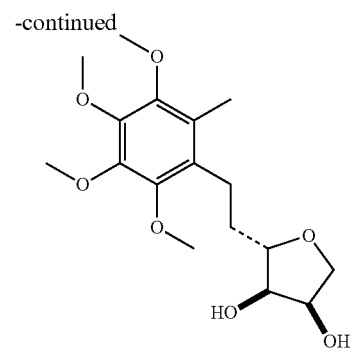

To a solution of Admix β (5.44 g, 1.4 g/mmol) in a 1:1 mixture of water/tBuOH (20 mL each) was added 2-[2-(2,3,4,5-tetramethoxy-6-methylphenyl)ethyl]-2,5-dihydrofuran (1.2 g, 3.9 mmol) and then methanesulfonamide (74 mg, 0.2 eq). The reaction was stirred overnight at rt and then diluted with water/EtOAc. To the reaction was added sodium dithionite (1.2 g) and stirring continued for 30 min. The organic layer was separated and the aqueous layer extracted with EtOAc (20 mL). The combined organic layers were washed with water and brine, dried on sodium sulfate, filtered and evaporated under reduced pressure. The residue was purified by flash chromatography (Biotage SP4, SNAP 100 column, nHex/EtOAc from 40% to 90% in 12 CV) to afford the title compound as a colourless oil (1.16 g, Yield: 87%). The two diastereoisomers were not separated.

$^1$H NMR (300 MHz, CDCl$_3$) δ 4.70 (s, 1H), 4.41 (td, J=11.9, 5.4, 1H), 4.28-4.05 (m, 6H), 3.93-3.71 (m, 28H), 3.71-3.56 (m, 2H), 3.16 (d, J=5.3, 1H), 2.81-2.55 (m, 7H), 2.18 (2s, 6H), 1.93-1.71 (m, 4H).

Step 6: 2-[2-(4,5-dimethoxy-2-methyl-3,6-dioxocyclohexa-1,4-dien-1-yl)ethyl]-4-(nitrooxy)tetrahydrofuran-3-yl nitrate

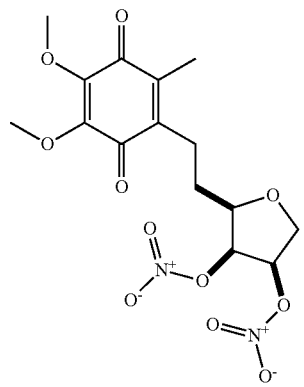

To a stirred solution of racemic 2-[2-(2,3,4,5-tetramethoxy-6-methylphenyl)ethyl]tetrahydrofuran-3,4-diol (1.15 g, 3.36 mmol), Bu$_4$NNO$_3$ (2.35 g, 7.7 mmol, 2.2 eq) and 2,6-di-tert-butyl-4-methylpyridine (1.51 g, 7.35 mmol, 2.05 eq) in dry CH$_2$Cl$_2$ (40 mL) cooled to −78° C. was added dropwise a solution of trifluoromethansulfonic anhydride (1.21 mL, 7.2 mmol, 2.0 eq) in dry CH$_2$Cl$_2$ (5 mL). The reaction was stirred at −78° C. for 1 h and left to go back to rt in 30 min. The reaction was quenched by addition of a saturated solution of NH$_4$Cl (5 mL) and the organic layer was separated, washed with water and brine, dried on sodium sulfate, filtered and evaporated under reduced pressure. The residue was purified by flash chromatography (Biotage SP4, SNAP 100 column, EtOAc/nHex: 25/75 to 60/40 in 12 CV) to give the title compound as a red oil (153 mg, Yield: 11%). Only diastereoisomer 1 was isolated.

$^1$H NMR (300 MHz, CDCl$_3$) δ 5.60 (dd, J=10.8, 7.9, 1H), 5.21-5.12 (m, 1H), 4.38 (dd, J=10.9, 6.0, 1H), 4.00 (s, 5H), 3.97-3.85 (m, 2H), 2.73-2.50 (m, 2H), 2.03 (s, 3H), 1.97-1.81 (m, 1H), 1.73 (ddd, J=19.9, 11.4, 7.2, 1H).

EXAMPLE 41

Synthesis of 2-[2-(1,4-dimethoxy-3-methyl-naphthalen-2-yl)-ethyl]-3,4-bis-nitrooxy-tetrahydro-furan (Compound (36) and (37))

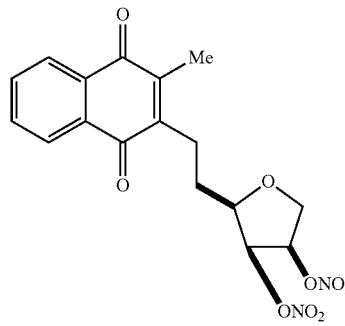
(36)

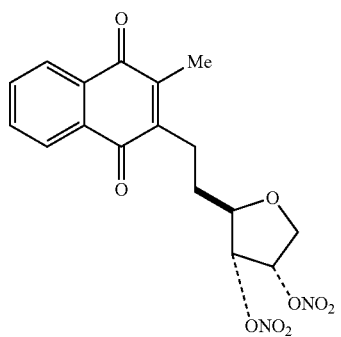
(37)

Step 1: Synthesis of 3-(1,4-dimethoxy-3-methyl-naphthalen-2-yl)-propionaldehyde

To a stirred solution of 3-(1,4-dimethoxy-3-methyl-naphthalen-2-yl)-propan-1-ol (4.3 g, 16.5 mmol) in dry DCM cooled to 0° C. was added pyridinium chlorochromate (5.34 g, 24.8 mmol, 1.5 eq). The reaction was stirred for 5 h at rt then filtered on a bed of celite. The filtrate was evaporated under reduced pressure and the residue purified by flash chromatography (Biotage SP4, SNAP 340 column, nHex/EtOAc 85/15 to 70/30 in 8 CV) to afford the title compound as a colourless oil (1.76 g, Yield: 41%).

$^1$H NMR (300 MHz, CDCl$_3$) δ 9.88 (s, 1H), 8.09-7.92 (m, 2H), 7.54-7.40 (m, 2H), 3.90 (s, 3H), 3.87 (s, 3H), 3.19-3.03 (m, 2H), 2.80-2.62 (m, 2H), 2.38 (s, 3H).

Step 2: Synthesis of 5-(1,4-dimethoxy-3-methyl-naphthalen-2-yl)-pent-1-en-3-ol

To a solution of 3-(1,4-dimethoxy-3-methyl-naphthalen-2-yl)-propionaldehyde (1.76 g, 6.82 mmol) in dry THF (40 mL) cooled to −78° C. was added a 1M solution of vinylmagnesium bromide in THF (18 mL, 18 mmol, 2.6 eq). The reaction was stirred for 1 h at −78° C. and then quenched by addition of water. EtOAc was added and the organic layer was separated, washed with water and brine, dried on sodium sulfate, filtered and evaporated. The residue was purified by flash chromatography (Biotage SP4, SNAP 100 column, nHex/EtOAc 80/20 to 55/45 in 10 CV) to afford the title compound as a colourless oil (1.65 g, Yield: 85%).

$^1$H NMR (300 MHz, CDCl$_3$) δ 8.03 (dtd, J=10.4, 6.8, 3.4, 3H), 7.56-7.40 (m, 3H), 5.90 (ddd, J=17.1, 10.5, 5.5, 1H), 5.26 (dt, J=17.2, 1.5, 1H), 5.10 (dd, J=10.5, 1.4, 1H), 4.10-3.99 (m, 1H), 3.98-3.89 (m, 4H), 3.87 (s, 4H), 3.05-2.85 (m, 3H), 2.43 (s, 3H), 1.83-1.73 (m, 2H).

Step 3: Synthesis of 2-(3-allyloxy-pent-4-enyl)-1,4-dimethoxy-3-methyl-naphthalene To a stirred solution of 5-(1,4-dimethoxy-3-methyl-naphthalen-2-yl)-pent-1-en-3-ol (1.65 g, 5.76 mmol) in dry THF (40 mL) cooled to −10° C. was added a 40% solution of sodium bis-trimethylsilylamide in THF (3.81 mL, 8.17 mmol, 1.4 eq). After 10 min of stirring, 15crown-5 (0.127 g, 0.58 mmol, 0.1 eq) and allylbromide (0.99 g, 8.17 mmol, 1.2 eq) were added and the reaction stirred overnight at rt. The reaction was then diluted with water and extracted with EtOAc (2×20 mL). The combined organic layers were washed with water and brine, dried on sodium sulfate, filtered and evaporated. The residue was purified by flash chromatography (Biotage SP4, SNAP 100 column, nHex/EtOAc: 80/20 to 65/35 in 10 CV) to afford the title compound as a colourless oil (0.89 g, Yield: 40%).

$^1$H NMR (300 MHz, CDCl$_3$) δ 8.15-7.92 (m, 2H), 7.51-7.37 (m, 2H), 5.97 (ddt, J=17.2, 10.6, 5.4, 1H), 5.79 (ddd, J=17.5, 10.3, 7.5, 1H), 5.36-5.13 (m, 4H), 4.11 (dddd, J=8.1, 5.1, 4.3, 2.7, 2H), 3.95-3.78 (m, 8H), 2.98-2.77 (m, 2H), 2.42 (s, 3H), 1.95-1.66 (m, 2H).

Step 4: Synthesis of 2-[2-(1,4-dimethoxy-3-methyl-naphthalen-2-yl)-ethyl]-2,5-dihydro-furan A solution of 2-(3-allyloxy-pent-4-enyl)-1,4-dimethoxy-3-methyl-naphthalene (0.889 g, 2.73 mmol) and Grubbs catalyst 1$^{st}$ generation (99 mg, 0.121 mmol, 0.05 eq) were heated at reflux for 2 h then cooled to rt and evaporated to dryness. The residue was purified by flash chromatography (Biotage SP4, SNAP 100 column, nHex/EtOAc: 85/15 to 65/35 in 10 CV) to afford the title compound as a colourless oil (0.749 g, Yield: 92%).

$^1$H NMR (300 MHz, CDCl$_3$) δ 8.10-7.96 (m, 2H), 7.52-7.39 (m, 2H), 5.95 (dd, J=6.2, 1.7, 1H), 5.91-5.81 (m, 1H), 5.03-4.89 (m, 1H), 4.82-4.57 (m, 2H), 3.92 (s, 3H), 3.87 (s, 3H), 3.01-2.77 (m, 2H), 2.42 (s, 3H), 1.92-1.69 (m, 2H).

Step 5: Synthesis of 2-[2-(1,4-dimethoxy-3-methyl-naphthalen-2-yl)-ethyl]-tetrahydro-furan-3,4-diol To a solution of ADmix β (3.5 g, 1.4 g/mmol of substrate) in a 1:1 mixture of water and tBuOH (7.5 mL each) was added 2-[2-(1,4-dimethoxy-3-methyl-naphthalen-2-yl)-ethyl]-2,5-dihydro-furan (0.749 g, 2.5 mmol) and methanesulfonamide (14 mg, 0.15 mmol, 0.2 eq). The reaction was stirred overnight at rt and then diluted with water and EtOAc. The reaction was carefully quenched with sodium metabisulfite (2.3 g) and stirred for another 30 min. The organic layer was separated and washed with water and brine, dried on sodium sulfate, filtered and evaporated under reduced pressure. The residue was purified by flash chromatography (Biotage SP4, SNAP 100 column, nHex/EtOAc: 60/40 to 10/90 in 10 CV) to afford the title compound as a colourless oil (0.68 g, Yield: 82%).

$^1$H NMR (300 MHz, CDCl$_3$) δ 8.03 (ddt, J=5.7, 3.5, 2.6, 2H), 7.46 (dt, J=9.9, 3.2, 2H), 4.41 (dd, J=11.7, 5.5, 1H), 4.28-4.05 (m, 3H), 3.97-3.80 (m, 8H), 3.75 (dd, J=9.5, 5.3, 1H), 3.65 (dt, J=12.5, 5.4, 1H), 2.93 (qdd, J=13.2, 9.1, 5.9, 2H), 2.46-2.41 (m, 3H), 2.00-1.80 (m, 2H).

Step 6: Synthesis of 2-[2-(1,4-dimethoxy-3-methyl-naphthalen-2-yl)-ethyl]-3,4-bis-nitrooxy-tetrahydro-furan To a stirred solution of racemic 2-[2-(1,4-dimethoxy-3-methyl-naphthalen-2-yl)-ethyl]-tetrahydro-furan-3,4-diol (200 mg, 0.602 mmol), Bu$_4$NNO$_3$ (404 mg, 1.32 mmol, 2.2 eq) and 2,6-di-tert-butyl-4-methylpyridine (271 mg, 1.32 mmol, 2.2 eq) in dry CH$_2$Cl$_2$ (10 mL) cooled to −78° C. was added dropwise a solution of trifluoromethansulfonic anhydride (205 μL, 1.25 mmol, 2.1 eq) in dry CH$_2$Cl$_2$ (3 mL). The reaction was stirred at −78° C. for 1 h and left to go back to rt in 30 min. The reaction was quenched by addition of a saturated solution of NH$_4$Cl (5 mL) and the organic layer was separated, washed with water and brine, dried on sodium sulfate, filtered and evaporated under reduced pressure. The residue was purified by flash chromatography (Biotage SP4, SNAP 100 column, EtOAc/nHex: 25/75 to 60/40 in 12 CV) to give: F1: Compound 36, red oil (34 mg, Yield: 14%)

$^1$H NMR (300 MHz, CDCl$_3$) δ 8.09 (dd, J=8.6, 5.1, 2H), 7.72 (dd, J=5.6, 3.3, 2H), 5.71-5.57 (m, 1H), 5.30-5.16 (m, 1H), 4.40 (dd, J=11.0, 6.0, 1H), 4.01 (td, J=7.8, 4.0, 1H), 3.93 (dd, J=11.0, 4.4, 1H), 2.92-2.66 (m, 2H), 2.22 (s, 3H), 2.08-1.91 (m, 2H), 1.91-1.72 (m, 1H).

$^{13}$C NMR (75 MHz, CDCl$_3$) δ 185.01, 184.53, 145.56, 143.91, 133.53, 133.52, 132.11, 132.04, 126.35, 126.29, 81.03, 77.87, 77.85, 77.61, 68.87, 31.27, 22.98, 12.62.

And the second diastereoisomer F2: Compound 37, pale yellow solid (30 mg, Yield: 13%).

$^1$H NMR (300 MHz, CDCl$_3$) δ 8.13-8.05 (m, 2H), 7.75-7.68 (m, 2H), 5.74-5.65 (m, 2H), 4.22-4.09 (m, 3H), 4.07-4.00 (m, 1H), 2.87 (ddd, J=12.7, 9.0, 6.8, 1H), 2.78-2.66 (m, 1H), 2.23 (s, 3H), 1.93-1.82 (m, 2H).

$^{13}$C NMR (75 MHz, CDCl$_3$) δ 185.02, 184.63, 145.59, 144.13, 133.53, 133.48, 132.12, 132.03, 126.30, 79.03, 78.89, 78.81, 67.80, 27.45, 23.41, 12.61.

EXAMPLE 42

Effects of the Compound 6 in a Mouse Model of Duchenne Muscle Distrophy (DMD)

The effects of the compound (6) on muscle function were assessed in mdx mice, which are genetically and biochemically homologous to human DMD. Animals of 4 weeks of age were treated for 3 months with the compound (6) at two different doses (30 and 100 mg/kg), which was incorporated into the diet. Control mdx and wild-type mice were fed the same diet without any drug. To determine if treatment with the compound would ameliorate muscle function in mdx mice, we evaluated the whole body tension which is a measure of the total muscle force. Indeed, this assay, well described in the Treat-NMD standard procedures for the pre-clinical studies in DMD, is used to determine the ability of mice to exert tension in a pulling maneuver that is elicited by stroking the tail. It is thought to reflect the maximal acute phasic force of the mouse can achieve to escape a potentially harmful event. Briefly, each mouse was placed at the entry of a polyvinyl chloride tube that had been lined interiorly with an aluminum screen, and the tail of the mouse was connected to a tension transducer. Forward pulling movements were elicited by a standardized stroke of the tail with serrated forceps and the corresponding forward pulling tensions (FPTs) were recorded using a Biopac recording system. Between 15 and 20 FPTs were generally recorded during each session. The whole body tension 5 (WBT5) and WBT10 were obtained by dividing the average of the top 5 or top 10 FPTs, respectively, by the body weight.

As depicted in table 8, mdx mice showed a significant impairment on muscle function compared to wild type animals and this was observed in both WBT5 and WBT10. The compound (6), administered for 3 months in the diet, showed a dose-response trend in improving muscle function reaching a significant effect at the dose of 100 mg/kg. The beneficial effects of the compound (6) were observed not only on WBT5 but also on WBT10, thus demonstrating the efficacy also on muscle resistance.

TABLE 8

| Mouse model of Duchenne Muscle Distrophy (DMD) | | |
|---|---|---|
| Treatment group | WBT5 | WBT10 |
| Wild type mice Control | 7.5 ± 1.4 | 6.6 ± 1.2 |
| Mdx mice control | 2.8 ± 0.7$^{\#\#\#}$ | 2.3 ± 0.4$^{\#\#\#}$ |
| Mdx mice Compound (6) 30 mg/kg/day | 3.6 ± 0.7$^{\#\#\#}$ | 3.0 ± 0.7$^{\#\#\#}$ |
| Mdx mice Compound (6) 100 mg/kg/day | 4.1 ± 0.8$^{\#\#\#}$* | 3.4 ± 0.6$^{\#\#\#}$* |

Table.1 Whole Body Tension (WBT) measured in wild-type and mdx control mice and in mdx mice treated with two different doses of NCX 1443 (30 and 100 mg/kg) incorporated in the diet. Data are presented as mean±standard deviation. For each group, n=8-10 mice. *p<0.05 vs mdx vehicle, $^{\#\#\#}$p<0.001 vs wild-type (wt) mice, 1-way ANOVA followed by Tuckey post-hoc test.

The invention claimed is:

1. A method of treating Sickle cell disease comprising administering a compound of formula (I) to a patient in need thereof:

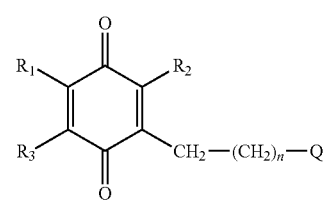

(I)

or steroisomers thereof, wherein

R$_1$ is selected from H, methyl, methoxy;

R$_3$ is selected from H, methyl, methoxy;

or R$_1$ and R$_3$ together form —CH=CH—CH=CH—;

R$_2$ is H, methyl;

n is an integer from 0 to 10;

Q is selected from the group consisting of:
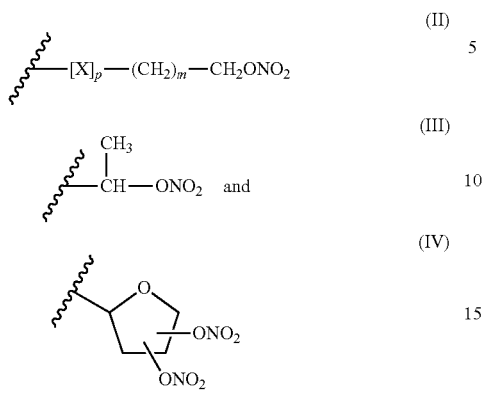
wherein
m is an integer from 0 to 6;
p is an integer from 0 to 1;
X is O, S or is —$CHONO_2$, with the proviso that when X is —$CHONO_2$ then m is 0.
* * * * *